(12) United States Patent
Kuchroo et al.

(10) Patent No.: US 8,329,660 B2
(45) Date of Patent: Dec. 11, 2012

(54) TIM-3 LIGANDS AND METHODS THEREOF

(75) Inventors: Vijay K. Kuchroo, Newton, MA (US); Terry Strom, Brookline, MA (US); Eugene K. Cha, Muttontown, NY (US); Sumone Chakravarti, Oakland, CA (US); Catherine Sabatos, San Francisco, CA (US); Chen Zhu, Brookline, MA (US); Xin Xiao Zheng, Wellesley, MA (US); Alberto Sanchez-Fueyo, Barcelona (ES)

(73) Assignees: The Brigham and Women's Hospital, Inc., Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 495 days.

(21) Appl. No.: 10/958,169

(22) Filed: Oct. 4, 2004

(65) Prior Publication Data

US 2005/0191721 A1 Sep. 1, 2005

Related U.S. Application Data

(60) Provisional application No. 60/508,319, filed on Oct. 3, 2003.

(51) Int. Cl.
*A61K 39/395* (2006.01)
(52) U.S. Cl. .................................................... 514/21.2
(58) Field of Classification Search .................. None
See application file for complete search history.

(56) References Cited

U.S. PATENT DOCUMENTS

| | | | |
|---|---|---|---|
| 6,027,916 A | 2/2000 | Ni et al. | |
| 6,066,322 A | 5/2000 | Levinson | |
| 6,066,498 A | 5/2000 | Levinson | |
| 6,084,083 A | 7/2000 | Levinson | |
| 6,156,887 A | 12/2000 | Levinson | |
| 6,190,909 B1 | 2/2001 | Levinson et al. | |
| 6,204,371 B1 | 3/2001 | Levinson | |
| 6,288,218 B1 | 9/2001 | Levinson | |
| 6,414,117 B1 | 7/2002 | Levinson | |
| 6,455,685 B1 | 9/2002 | Levinson | |
| 6,468,768 B1 | 10/2002 | Ni et al. | |
| 6,562,343 B1 * | 5/2003 | Levinson | 424/139.1 |
| 2003/0069196 A1 | 4/2003 | Levinson et al. | |
| 2003/0124114 A1 | 7/2003 | McIntire et al. | |
| 2004/0005322 A1 | 1/2004 | Kuchroo et al. | |
| 2004/0223971 A1 | 11/2004 | Chang et al. | |
| 2005/0276756 A1 | 12/2005 | Hoo et al. | |

FOREIGN PATENT DOCUMENTS

| | | |
|---|---|---|
| WO | WO-98/15624 | 10/1997 |
| WO | WO 99/35158 | 7/1999 |
| WO | 01/12215 | 2/2001 |
| WO | WO 01/57188 | 8/2001 |
| WO | WO-0155304 | 9/2001 |
| WO | WO-02081517 | 10/2002 |
| WO | WO 03/002722 | 1/2003 |
| WO | WO-03/002722 A2 | 1/2003 |
| WO | WO-03/063792 | 8/2003 |
| WO | WO 03/080673 | 10/2003 |
| WO | WO 2004/060041 | 7/2004 |
| WO | WO 2005/027854 | 3/2005 |

OTHER PUBLICATIONS

Matsumoto et al. Journal of Immunology, 2002, 168:1961-1967.*
Wada et al. Journal of Biological Chemistry, 1997, vol. 272, p. 6078-6086.*
Zhu et al. Nature Immunology, 2005, vol. 6, No. 12, p. 1245-1252.*
Ngo et al., 1994, The Protein Folding Problem and Tertiary Structure Prediction, pp. 492-495.*
Attwood, Science 2000; 290:471-473.*
Skolnick et al. .Trends in Biotech. 2000; 18(1):34-39.*
Metzler et al. Nature Structural Biol. 1997; 4:527-531.*
Janeway et al. , Immunobiology, 2005, $6^{th}$ Ed., p. 1-2.*
Feigelstock D. et al. The human homolog of HAVcr-1 codes for a hepatitis A virus cellular receptor. *J Virol*. 1998;72(8):6821-8.
Khademi M. et al. T Cell Ig- and mucin-domain-containing molecule-3 (TIM-3) and TIM-1 molecules are differentially expressed on human Th1 and Th2 cells and in cerebrospinal fluid-derived mononuclear cells in multiple sclerosis. *J. Immunol.* 2004;172(11):7169-76.
Kikutani H. et al. Semaphorins in interactions between T cells and antigen-presenting cells. *Nat Rev Immunol*. 2003;3(2):159-67.
Sabatos CA. et al. Interaction of Tim-3 and Tim-3 ligand regulates T helper type 1 responses and induction of peripheral tolerance. *Nat Immunol* 4:1102-1110, 2003.
Sanchez-Fueyo, A. et al. The Ig superfamily member Tim-3 inhibits Th1-mediated auto- and allo-immune response and promotes immunological tolerance. *Nat Immunol* 4:1093-1101, 2003.
Genbank Accession No. NP002299, galectin 9 short isoform (human), 2002.
Genbank Accession No. NP033665, galection 9 long isoform (human), 2002.
Genbank Accession No. NP034838. lectin, galactose binding, soluble 9 (mouse), 2002.
McIntire, et al., "Hepatitis A virus link to atopic disease," *Nature*, 425: 576 (2003).
Loza et al., 2005, Clin. Exp. Allergy, vol. 35: 8-17.
De Souza et al., 2005, PNAS, vol. 102: 17113-17118.
Meyers et al., 2005, Trends in Mol. Med. vol. 11: 362-369.
Meyers et al., 2005, Nat. Immunol. vol. 6: 455-464.
Burgess et al., 1990, J. Cell. Biol. vol. 111: 2129-2138.

(Continued)

*Primary Examiner* — Yunsoo Kim
(74) *Attorney, Agent, or Firm* — Nixon Peabody LLP; David S. Resnick; Mark J. FitzGerald

(57) ABSTRACT

The invention relates to isolated polypeptides and nucleic acids encoding polypeptides which comprise a tim-3 IgV domain and a tim-3 intracellular domain, wherein the polypeptides do not comprise a tim-3 mucin domain or a tim-3 transmembrane domain. In addition, the invention relates to methods of modulating immune responses in a subject, comprising administering to the subject a therapeutically effective amount of an agent that modulates tim-3 activity. Immune responses include, but are not limited to, immune tolerance, transplantation tolerance, Th1 responses and Th2 responses.

8 Claims, 33 Drawing Sheets

OTHER PUBLICATIONS

Bailly et al. Shedding of kidney injury molecule-1, a putative adhesion protein involved in renal regeneration. *J Biol Chem.* 2002;277(42):39739-48.

Chae SC. et al. The exon 4 variations of Tim-1 gene are associated with rheumatoid arthritis in a Korean population. *Biochem Biophys Res Commun.* 2004;315(4):971-5.

Chae SC. et al. The association of the exon 4 variations of Tim-1 gene with allergic diseases in a Korean population. *Biochem Biophys Res Commun.* 2003;312(2):346-50.

Chae SC. et al. Molecular variations in the promoter and coding regions of human Tim-1 gene and their association in Koreans with asthma. *Hum Immunol.* 2003; 64(12):1177-82.

Feigelstock D. et al. The human homolog of HAVcr-1 codes for a hepatitis A virus cellular receptor. *J Virol.* 1998;72(8):6621-8.

Ichimura T. et al. Kidney injury molecule-1 (KIM-1), a putative epithelial cell adhesion molecule containing a novel immunoglobulin domain, is up-regulated in renal cells after injury. *J Biol Chem.* 1998;273(7):4135-42.

Kaplan, G. et al. Identification of a surface glycoprotein on African green monkey kidney cells as a receptor for hepatitis A virus. Embo J. 15, 4282-4296 (1996).

Khademi M. et al. T Cell Ig- and mucin-domain-containing molecule-3 (TIM-3) and TIM-1 molecules are differentially expressed on human Th1 and Th2 cells and in cerebrospinal fluid-derived mononuclear cells in multiple sclerosis. *J. Immunol.* 2004;172(11):7169-76.

Kikutani H. et al. Semaphorins in interactions between T cells and antigen-presenting cells. *Nat Rev Immunol.* 2003;3(2):159-67.

Kuchroo, V. et al. The TIM gene family: emerging roles in immunity and disease. Nat Rev Immunol 3, 454-462 (2003).

Kumanogoh A. et al. Immune semaphorins: a new area of semaphorin research. *J Cell Sci.* 2003;116(Pt 17):3463-70.

Kumanogoh A. et al. Class IV semaphorin Sema4A enhances T-cell activation and interacts with Tim-2. *Nature.* 2002; 419(6907):629-33.

McIntire JJ. et al. TIM-1, a novel allergy and asthma susceptibility gene. Springer Semin Immunopathol. 2004;25(3-4):335-48. Epub Oct. 24, 2003.

McIntire, J. et al. Identification of Tapr (an airway hyperreactivity regulatory locus) and the linked Tim gene family. Nat Immunol 2, 1109-1116 (2001).

Monney L. et al. Th1-specific cell surface protein Tim-3 regulates macrophage activation and severity of an autoimmune disease. *Nature.* 2002;415(6871):536-41.

Noguchi E. et al. Insertion/deletion coding polymorphisms in hHAVcr-1 are not associated with atopic asthma in the Japanese population. *Genes Immun.* 2003;4(2):170-3.

Rabinovich GA. et al. Galectins and their ligands: amplifiers, silencers or tuners of the inflammatory response? *Trends Immunol* 23:313-320; 2002.

Rabinovich GA. et al. Role of galectins, in inflammatory and immunomodulatory processes *Biochim Biophys Acta* 1572:274-284, 2002.

Sabatos CA. et al. Interaction of Tim-3 and Tim-3 ligand regulates T helper type 1 responses and induction of peripheral tolerance. *Nat Immunol* 4:1102-1110 2001.

Sanchez-Fueyo, A. et al. The Ig superfamily member Tim-3 inhibits Th1-mediated auto- and allo-immune response and promotes immunological tolerance. *Nat Immunol* 4:1093-1101, 2003.

Shakhov AN. et al. SMUCKLER/TIM4 is a distinct member of TIM family expressed by stromal cells of secondary lymphoid tissues and associated with lymphotoxin signaling. *Eur J Immunol.* 2004;34(2):494-503.

Silberstein E. et al. Neutralization of hepatitis A virus (HAV) by an immunoadhesin containing the cysteine-rich region of HAV cellular receptor-1. *J Virol.* 2001;75(2):717-25.

Thompson, P. et al. The Cys-rich region of hepatitis A virus cellular receptor 1 is required for binding of hepatitis A virus and protective monoclonal antibody 190/4. J Virol 72, 3751-3761 (1998).

Tureci et al. Molecular definition of a novel human galectin which is immunogenic in patients with Hodgkin's disease. *J Biol Chem.* 1997;272(10):6416-22.

Xing, L. et al. Distinct cellular receptor interactions in poliovirus and rhinoviruses. EMBO J 19, 1207-1216 (2000).

Yoshida H. et al. Interleukin-1beta stimulates galectin-9 expression in human astrocytes *Neuroreport* 12:3755-3758, 2001.

Genbank Accession No. NP002299, galectin 9 short isoform (human), 2004.

Genbank Accession No. NP033665, galection 9 long isoform (human), 2004.

Genbank Accession No. NP034838, lectin, galactose binding, soluble 9 (mouse), 2004.

* cited by examiner

Fig. 1B signal peptide

| | |
|---|---|
| fl-TIM-3 | MFSGLTLNCVLLLLQLLLARS LEDGYKVEVGKNAYLPCSYTLPTSG |
| s-TIM-3 | MFSGLTLNCVLLLLQLLLARS LEDGYKVEVGKNAYLPCSYTLPTSG |

IgV domain

| | |
|---|---|
| fl-TIM-3 | TLVPMCWGKGFCPWSQCTNELLRTDERNVTYQKSSRYQLKGDLNKG |
| s-TIM-3 | TLVPMCWGKGFCPWSQCTNELLRTDERNVTYQKSSRYQLKGDLNKG |

| | |
|---|---|
| fl-TIM-3 | DVSLIIKNVTLDDHGTYCCRIQFPGLMNDKKLELKLDIKA AKVTPA |
| s-TIM-3 | DVSLIIKNVTLDDHGTYCCRIQFPGLMNDKKLELKLDIKA------ | mucin domain

| | |
|---|---|
| fl-TIM-3 | QTAHGDSTTASPRTLTTERNGSETQTLVTLHNNNGTKISTWADEIK |
| s-TIM-3 | --------------------------------------------- | transmembrane domain

| | |
|---|---|
| fl-TIM-3 | DSGETIR TAIHIGVGVSAGLTLALIIGVLIL KWYSCKKKKLSSLSL |
| s-TIM-3 | ------- ---------------------- -GYSCKKKKLSSLSL | cytoplasmic domain

| | |
|---|---|
| fl-TIM-3 | ITLANLPPGGLANAGAVRIRSEENIYTIEENVYEVENSNEYYCYVN |
| s-TIM-3 | ITLANLPPGGLANAGAVRIRSEENIYTIEENVYEVENSNEYYCYVN |

| | |
|---|---|
| fl-TIM-3 | SQQPS |
| s-TIM-3 | SQQPS |

Fig. 5

Tim-3-Ig treatment *in vivo* inhibited induction of tolerance

PLP 139-151 (100 mg/ml) re-stimulation *in vitro*

| Tolerance | Treatment | Immunization | Proliferation cpm | IL-2 | IFN-γ pg/ml | IL-4 | IL-10 |
|---|---|---|---|---|---|---|---|
| PBS | hIgG | PLP/CFA | 66,696 | 639 | 1,316 | 0 | 0 |
| PLP | hIgG | PLP/CFA | 21,379† | 0‡ | 0§ | 0 | 0 |
| PBS | Tim-3-Ig | PLP/CFA | 86,303 | 745 | 2,777 | 0 | 0 |
| PLP | Tim-3-Ig | PLP/CFA | 84,235* | 1,345◊ | 1,976˜ | 0 | 0 |

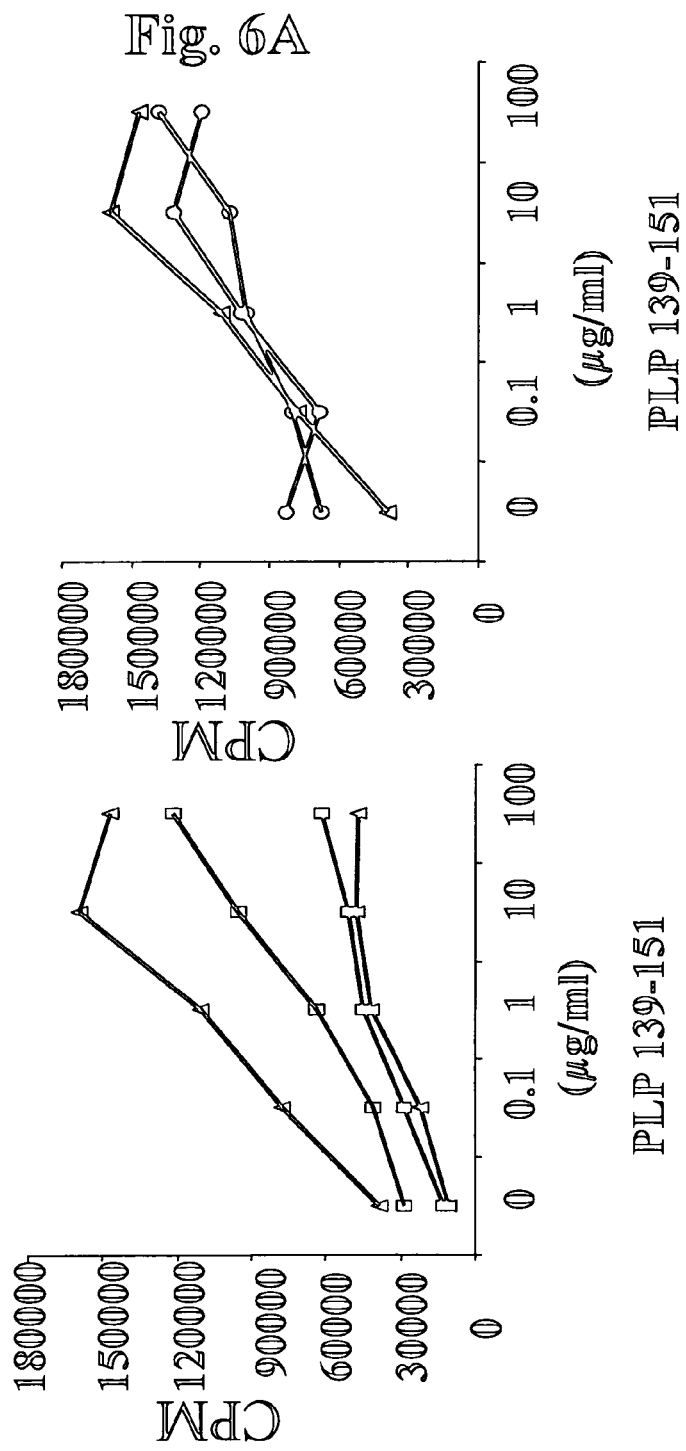

A

B

■ DST plus αCD154 and hIgG1 (*n* = 8)
○ No treatment (*n* = 8; MST =18)
▼ DST plus αCD154 and fl-TIM-3/Ig (*n* = 6; MST =21)

-□- 4x10⁵ CD4+CD25- plus 4x10⁵ CD4+CD25+
(naive donor; $n = 7$; MST = 12)

-△- 4x10⁵ CD4+CD25- plus 4x10⁵ CD4+CD25+
(DST + αCD154 + hIg1 treated donor; $n = 7$; MST = 150)

-▽- 4x10⁵ CD4+CD25- plus 4x10⁵ CD4+CD25+
(DST + αCD154 + fl-TIM-3-Ig treated donor; $n = 7$; MST = 16)

SEQUENCE LISTING

```
<160> NUMBER OF SEQ ID NOS: 19

<210> SEQ ID NO 1
<211> LENGTH: 624
<212> TYPE: DNA
<213> ORGANISM: Homo sapiens

<400> SEQUENCE: 1
atgttttcac atcttccctt tgactgtgtc ctgctgctgc tgctgctact acttacaagg      60
tcctcagaag tggaatacag agcggaggtc ggtcagaatg cctatctgcc ctgcttctac     120
accccagccg ccccagggaa cctcgtgccc gtctgctggg gcaaaggagc ctgtcctgtg     180
tttgaatgtg gcaacgtggt gctcaggact gatgaaaggg atgtgaatta ttggacatcc     240
agatactggc taaatgggga tttccgcaaa ggagatgtgt ccctgaccat agagaatgtg     300
actctagcag acagtgggat ctactgctgc cggatccaaa tcccaggcat aatgaatgat     360
gaaaaattta acctgaagtt ggtcatcaaa ccagggtatt ctcatagcaa agagaagata     420
cagaatttaa gcctcatctc tttggccaac ctccctccct caggattggc aaatgcagta     480
gcagagggaa ttcgctcaga agaaaacatc tataccattg aagagaacgt atatgaagtg     540
gaggagccca atgagtatta ttgctatgtc agcagcaggc agcaaccctc acaacctttg     600
ggttgtcgct ttgcaatgcc atag                                            624

<210> SEQ ID NO 2
<211> LENGTH: 207
<212> TYPE: PRT
<213> ORGANISM: Homo sapiens

<400> SEQUENCE: 2

Met Phe Ser His Leu Pro Phe Asp Cys Val Leu Leu Leu Leu Leu Leu
  1               5                  10                  15

Leu Leu Thr Arg Ser Ser Glu Val Glu Tyr Arg Ala Glu Val Gly Gln
             20                  25                  30

Asn Ala Tyr Leu Pro Cys Phe Tyr Thr Pro Ala Ala Pro Gly Asn Leu
         35                  40                  45

Val Pro Val Cys Trp Gly Lys Gly Ala Cys Pro Val Phe Glu Cys Gly
     50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125
```

```
Ile Lys Pro Gly Tyr Ser His Ser Lys Glu Lys Ile Gln Asn Leu Ser
        130                 135                 140

Leu Ile Ser Leu Ala Asn Leu Pro Pro Ser Gly Leu Ala Asn Ala Val
145                 150                 155                 160

Ala Glu Gly Ile Arg Ser Glu Glu Asn Ile Tyr Thr Ile Glu Asn
                165                 170                 175

Val Tyr Glu Val Glu Glu Pro Asn Glu Tyr Tyr Cys Tyr Val Ser Ser
            180                 185                 190

Arg Gln Gln Pro Ser Gln Pro Leu Gly Cys Arg Phe Ala Met Pro
        195                 200                 205

<210> SEQ ID NO 3
<211> LENGTH: 594
<212> TYPE: DNA
<213> ORGANISM: Mouse

<400> SEQUENCE: 3 atgtttcag gtcttaccct caactgtgtc ctgctgctgc tgcaactact acttgcaagg      60
tcattggaag atggttataa ggttgaggtt ggtaaaaatg cctatctgcc ctgcagttac    120
actctaccta catctgggac acttgtgcct atgtgctggg gcaagggatt ctgtccttgg    180
tcacagtgta ccaatgagtt gctcagaact gatgaaagaa atgtgacata tcagaaatcc    240
agcagatacc agctaaaggg cgatctcaac aaaggagatg tgtctctgat cataaagaat    300
gtgactctgg atgaccatgg gacctactgc tgcaggatac agttccctgg tcttatgaat    360
gataaaaaat tagaactgaa attagacatc aaagcagggt attcctgtaa gaaaaagaag    420
ttatcgagtt tgagccttat tacactggcc aacttgcctc caggagggtt ggcaaatgca    480
ggagcagtca ggattcgctc tgaggaaaat atctacacca tcgaggagaa cgtatatgaa    540
gtggagaatt caaatgagta ctactgctac gtcaacagcc agcagccatc ctga          594

<210> SEQ ID NO 4
<211> LENGTH: 197
<212> TYPE: PRT
<213> ORGANISM: Mouse

<400> SEQUENCE: 4

Met Phe Ser Gly Leu Thr Leu Asn Cys Val Leu Leu Leu Gln Leu
1                   5                   10                  15

Leu Leu Ala Arg Ser Leu Glu Asp Gly Tyr Lys Val Glu Val Gly Lys
                20                  25                  30

Asn Ala Tyr Leu Pro Cys Ser Tyr Thr Leu Pro Thr Ser Gly Thr Leu
            35                  40                  45

Val Pro Met Cys Trp Gly Lys Gly Phe Cys Pro Trp Ser Gln Cys Thr
50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95

Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
        115                 120                 125

Asp Ile Lys Ala Gly Tyr Ser Cys Lys Lys Lys Leu Ser Ser Leu
        130                 135                 140

Ser Leu Ile Thr Leu Ala Asn Leu Pro Pro Gly Gly Leu Ala Asn Ala
145                 150                 155                 160
```

```
Gly Ala Val Arg Ile Arg Ser Glu Glu Asn Ile Tyr Thr Ile Glu Glu
            165                 170                 175
Asn Val Tyr Glu Val Glu Asn Ser Asn Glu Tyr Tyr Cys Tyr Val Asn
        180                 185                 190
Ser Gln Gln Pro Ser
        195

<210> SEQ ID NO 5
<211> LENGTH: 16
<212> TYPE: DNA
<213> ORGANISM: Homo sapiens

<400> SEQUENCE: 5
caaaccaggg tattct                                                    16

<210> SEQ ID NO 6
<211> LENGTH: 16
<212> TYPE: PRT
<213> ORGANISM: Homo sapiens

<400> SEQUENCE: 6

Asn Leu Lys Leu Val Ile Lys Pro Gly Tyr Ser His Ser Lys Glu Lys
1               5                   10                  15

<210> SEQ ID NO 7
<211> LENGTH: 16
<212> TYPE: DNA
<213> ORGANISM: Mouse

<400> SEQUENCE: 7
caaagcaggg tattcc                                                    16

<210> SEQ ID NO 8
<211> LENGTH: 16
<212> TYPE: PRT
<213> ORGANISM: Mouse

<400> SEQUENCE: 8

Glu Leu Lys Leu Asp Ile Lys Ala Gly Tyr Ser Cys Lys Lys Lys Lys
1               5                   10                  15

<210> SEQ ID NO 9
<211> LENGTH: 972
<212> TYPE: DNA
<213> ORGANISM: Homo sapiens

<400> SEQUENCE: 9
atggccttca gcggttccca ggctccctac ctgagtccag ctgtcccctt ttctgggact      60
attcaaggag gtctccagga cggacttcag atcactgtca atgggaccgt tctcagctcc     120
agtggaacca ggtttgctgt gaactttcag actggcttca gtggaaatga cattgccttc     180
cacttcaacc ctcggtttga agatggaggg tacgtggtgt gcaacacgag gcagaacgga     240 agctggggc ccgaggagag gaggacacac atgcctttcc agaagggat gcccttgac        300 ctctgcttcc tggtgcagag ctcagatttc aaggtgatgg tgaacgggat cctcttcgtg     360
cagtacttcc accgcgtgcc cttccaccgt gtggacacca tcttcgtcaa tggctctgtg     420
cagctgtcct acatcagctt ccagcctccc ggcgtgtggc ctgccaaccc ggctcccatt     480
acccagacag tcatccacac agtgcagagc gcccctggac agatgttctc tactcccgcc     540
atcccaccta tgatgtaccc ccaccccgcc tatccgatgc ctttcatcac caccattctg     600
ggagggctgt acccatccaa gtccatcctc ctgtcaggca ctgtcctgcc cagtgctcag     660
```

```
aggttccaca tcaacctgtg ctctgggaac cacatcgcct tccacctgaa cctccgtttt    720
gatgagaatg ctgtggtccg caacacccag atcgacaact cctggggggtc tgaggagcga   780
```
```
agtctgcccc gaaaaatgcc cttcgtccgt ggccagagct tctcagtgtg atcttgtgt     840 ggagctcact gcctcaaggt ggccgtggat ggtcagcacc tgtttgaata ctaccatcgc    900
ctgaggaacc tgcccaccat caacagactg gaagtggggg gcgacatcca gctgacccat    960
gtgcagacat ag                                                        972
```

```
<210> SEQ ID NO 10
<211> LENGTH: 323
<212> TYPE: PRT
<213> ORGANISM: Homo sapiens

<400> SEQUENCE: 10
```

Met Ala Phe Ser Gly Ser Gln Ala Pro Tyr Leu Ser Pro Ala Val Pro
  1               5                  10                  15

Phe Ser Gly Thr Ile Gln Gly Leu Gln Asp Gly Leu Gln Ile Thr
             20                  25                  30

Val Asn Gly Thr Val Leu Ser Ser Gly Thr Arg Phe Ala Val Asn
         35                  40                  45

Phe Gln Thr Gly Phe Ser Gly Asn Asp Ile Ala Phe His Phe Asn Pro
 50                  55                  60

Arg Phe Glu Asp Gly Gly Tyr Val Val Cys Asn Thr Arg Gln Asn Gly
 65                  70                  75                  80

Ser Trp Gly Pro Glu Glu Arg Arg Thr His Met Pro Phe Gln Lys Gly
                 85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Phe Val Asn Gly Ser Val Gln Leu Ser Tyr
130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Phe His Ile
210                 215                 220

Asn Leu Cys Ser Gly Asn His Ile Ala Phe His Leu Asn Leu Arg Phe
225                 230                 235                 240

Asp Glu Asn Ala Val Val Arg Asn Thr Gln Ile Asp Asn Ser Trp Gly
                245                 250                 255

Ser Glu Glu Arg Ser Leu Pro Arg Lys Met Pro Phe Val Arg Gly Gln
            260                 265                 270

Ser Phe Ser Val Trp Ile Leu Cys Gly Ala His Cys Leu Lys Val Ala
        275                 280                 285

Val Asp Gly Gln His Leu Phe Glu Tyr Tyr His Arg Leu Arg Asn Leu
290                 295                 300

Pro Thr Ile Asn Arg Leu Glu Val Gly Gly Asp Ile Gln Leu Thr His
305                 310                 315                 320

Val Gln Thr

<210> SEQ ID NO 11
<211> LENGTH: 906
<212> TYPE: DNA
<213> ORGANISM: Homo sapiens

<400> SEQUENCE: 11

| | | | | | |
|---|---|---|---|---|---|
| atgttttcac | atcttcccttt | tgactgtgtc | ctgctgctgc | tgctgctact | acttacaagg | 60 |
| tcctcagaag | tggaatacag | agcggaggtc | ggtcagaatg | cctatctgcc | ctgcttctac | 120 |
| accccagccg | ccccagggaa | cctcgtgccc | gtctgctggg | gcaaaggagc | ctgtcctgtg | 180 |
| tttgaatgtg | gcaacgtggt | gctcaggact | gatgaaaggg | atgtgaatta | ttggacatcc | 240 |
| agatactggc | taaatgggga | tttccgcaaa | ggagatgtgt | ccctgaccat | agagaatgtg | 300 |
| actctagcag | acagtgggat | ctactgctgc | cggatccaaa | tcccaggcat | aatgaatgat | 360 |
| gaaaaattta | acctgaagtt | ggtcatcaaa | ccagccaagg | tcacccctgc | accgactctg | 420 |
| cagagagact | tcactgcagc | ctttccaagg | atgcttacca | ccaggggaca | tggcccagca | 480 |
| gagacacaga | cactggggag | cctccctgat | ataaatctaa | cacaaatatc | cacattggcc | 540 |
| aatgagttac | gggactctag | attggccaat | gacttacggg | actctggagc | aaccatcaga | 600 |
| ataggcatct | acatcggagc | agggatctgt | gctgggctgg | ctctggctct | tatcttcggc | 660 |
| gctttaattt | tcaatggta | ttctcatagc | aaagagaaga | tacagaattt | aagcctcatc | 720 |
| tctttggcca | acctccctcc | ctcaggattg | gcaaatgcag | tagcagaggg | aattcgctca | 780 |
| gaagaaaaca | tctataccat | tgaagagaac | gtatatgaag | tggaggagcc | caatgagtat | 840 |
| tattgctatg | tcagcagcag | gcagcaaccc | tcacaacctt | tgggttgtcg | ctttgcaatg | 900 |
| ccatag | | | | | | 906 |

<210> SEQ ID NO 12
<211> LENGTH: 846
<212> TYPE: DNA
<213> ORGANISM: Mouse

<400> SEQUENCE: 12

| | | | | | |
|---|---|---|---|---|---|
| atgttttcag | gtcttaccct | caactgtgtc | ctgctgctgc | tgcaactact | acttgcaagg | 60 |
| tcattggaag | atggttataa | ggttgaggtt | ggtaaaaatg | cctatctgcc | ctgcagttac | 120 |
| actctaccta | catctgggac | acttgtgcct | atgtgctggg | gcaagggatt | ctgtccttgg | 180 |
| tcacagtgta | ccaatgagtt | gctcagaact | gatgaaagaa | atgtgacata | tcagaaatcc | 240 |
| agcagatacc | agctaaaggg | cgatctcaac | aaaggagatg | tgtctctgat | cataaagaat | 300 |
| gtgactctgg | atgaccatgg | gacctactgc | tgcaggatac | agttccctgg | tcttatgaat | 360 |
| gataaaaaat | tagaactgaa | attagacatc | aaagcagcca | aggtcactcc | agctcagact | 420 |
| gcccatgggg | actctactac | agcttctcca | agaaccctaa | ccacggagag | aaatggttca | 480 |
| gagacacaga | cactggtgac | cctccataat | aacaatggaa | caaaaatttc | acatgggct | 540 |
| gatgaaatta | aggactctgg | agaaacgatc | agaactgcta | tccacattgg | agtgggagtc | 600 |
| tctgctgggt | tgacccctggc | acttatcatt | ggtgtcttaa | tccttaaatg | gtattccctgt | 660 |
| aagaaaaaga | agttatcgag | tttgagcctt | attacactgg | ccaacttgcc | tccaggaggg | 720 |
| ttggcaaatg | caggagcagt | caggattcgc | tctgaggaaa | atatctacac | catcgaggag | 780 |

-continued

```
aacgtatatg aagtggagaa ttcaaatgag tactactgct acgtcaacag ccagcagcca    840
tcctga                                                               846
```

<210> SEQ ID NO 13
<211> LENGTH: 301
<212> TYPE: PRT
<213> ORGANISM: Homo sapiens

<400> SEQUENCE: 13

```
Met Phe Ser His Leu Pro Phe Asp Cys Val Leu Leu Leu Leu Leu
  1               5                  10                  15

Leu Leu Thr Arg Ser Ser Glu Val Glu Tyr Arg Ala Glu Val Gly Gln
             20                  25                  30

Asn Ala Tyr Leu Pro Cys Phe Tyr Thr Pro Ala Ala Pro Gly Asn Leu
         35                  40                  45

Val Pro Val Cys Trp Gly Lys Gly Ala Cys Pro Val Phe Glu Cys Gly
     50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                 85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
        115                 120                 125

Ile Lys Pro Ala Lys Val Thr Pro Ala Pro Thr Leu Gln Arg Asp Phe
    130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly Ile Tyr Ile Gly Ala Gly
        195                 200                 205

Ile Cys Ala Gly Leu Ala Leu Ala Leu Ile Phe Gly Ala Leu Ile Phe
    210                 215                 220

Lys Trp Tyr Ser His Ser Lys Glu Lys Ile Gln Asn Leu Ser Leu Ile
225                 230                 235                 240

Ser Leu Ala Asn Leu Pro Pro Ser Gly Leu Ala Asn Ala Val Ala Glu
                245                 250                 255

Gly Ile Arg Ser Glu Glu Asn Ile Tyr Thr Ile Glu Glu Asn Val Tyr
            260                 265                 270

Glu Val Glu Glu Pro Asn Glu Tyr Tyr Cys Tyr Val Ser Ser Arg Gln
        275                 280                 285

Gln Pro Ser Gln Pro Leu Gly Cys Arg Phe Ala Met Pro
    290                 295                 300
```

<210> SEQ ID NO 14
<211> LENGTH: 281
<212> TYPE: PRT
<213> ORGANISM: Mouse

<400> SEQUENCE: 14

```
Met Phe Ser Gly Leu Thr Leu Asn Cys Val Leu Leu Leu Gln Leu
  1               5                  10                  15

Leu Leu Ala Arg Ser Leu Glu Asp Gly Tyr Lys Val Glu Val Gly Lys
             20                  25                  30

Asn Ala Tyr Leu Pro Cys Ser Tyr Thr Leu Pro Thr Ser Gly Thr Leu
             35                  40                  45

Val Pro Met Cys Trp Gly Lys Gly Phe Cys Pro Trp Ser Gln Cys Thr
 50                  55                  60

Asn Glu Leu Leu Arg Thr Asp Glu Arg Asn Val Thr Tyr Gln Lys Ser
 65                  70                  75                  80

Ser Arg Tyr Gln Leu Lys Gly Asp Leu Asn Lys Gly Asp Val Ser Leu
                 85                  90                  95

Ile Ile Lys Asn Val Thr Leu Asp Asp His Gly Thr Tyr Cys Cys Arg
                100                 105                 110

Ile Gln Phe Pro Gly Leu Met Asn Asp Lys Lys Leu Glu Leu Lys Leu
                115                 120                 125

Asp Ile Lys Ala Ala Lys Val Thr Pro Ala Gln Thr Ala His Gly Asp
130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
                180                 185                 190

Ala Ile His Ile Gly Val Gly Val Ser Ala Gly Leu Thr Leu Ala Leu
                195                 200                 205

Ile Ile Gly Val Leu Ile Leu Lys Trp Tyr Ser Cys Lys Lys Lys Lys
210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Glu Asn Ile Tyr
                245                 250                 255

Thr Ile Glu Glu Asn Val Tyr Glu Val Glu Asn Ser Asn Glu Tyr Tyr
                260                 265                 270

Cys Tyr Val Asn Ser Gln Gln Pro Ser
                275                 280
```

<210> SEQ ID NO 15
<211> LENGTH: 16
<212> TYPE: RNA
<213> ORGANISM: Artificial Sequence
<220> FEATURE:
<223> OTHER INFORMATION: Oligonucleotide corresponding to splice
      junction of human soluble tim-3

<400> SEQUENCE: 15
caaaccaggg uauucu                                                     16

<210> SEQ ID NO 16
<211> LENGTH: 969
<212> TYPE: DNA
<213> ORGANISM: Mouse

<400> SEQUENCE: 16
atggctctct tcagtgccca gtctccatac attaacccga tcatcccctt tactggacca    60
atccaaggag ggctgcagga gggacttcag gtgaccctcc aggggactac caagagtttt    120

```
gcacaaaggt tgtggtgaa ctttcagaac agcttcaatg gaaatgacat tgccttccac    180 ttcaacccc ggtttgagga aggagggtat gtggtttgca acacgaagca gaacggacag    240
tgggggcctg aggagagaaa gatgcagatg cccttccaga aggggatgcc ctttgagctt    300
tgcttcctgg tgcagaggtc agagttcaag gtgatggtga acaagaaatt ctttgtgcag    360
taccaacacc gcgtaccta ccacctcgtg gacaccatcg ctgtctccgg ctgcttgaag    420
ctgtccttta tcaccttcca gactcaggac tttgtcctg cccaccaggc acccatggct    480
caaactacca tccatatggt tcacagcacc cctggacaga tgttctctac tcctggaatc    540
cctcctgtgg tgtaccccac cccagcctat accataccttt ctacaccccc cattccaaat    600
gggctttacc cgtccaagtc catcatgata tcaggcaatg tcttgccaga tgctacgagg    660
ttccatatca accttcgctg tggaggtgac attgctttcc acctgaaccc ccgtttcaat    720
gagaatgctg ttgtccgaaa cactcagatc aacaactcct gggggcagga agagcgaagt    780
ctgcttggga ggatgccctt cagtcgaggc cagagcttct cggtgtggat catatgcgaa    840
ggtcactgct tcaaggtggc tgtgaatggt caacacatgt gtgaatatta ccaccgcctg    900
aagaacttgc aggatatcaa cactctagaa gtggcgggtg atatccagct gacccacgtg    960
cagacatag                                                           969

<210> SEQ ID NO 17
<211> LENGTH: 322
<212> TYPE: PRT
<213> ORGANISM: Mouse

<400> SEQUENCE: 17

Met Ala Leu Phe Ser Ala Gln Ser Pro Tyr Ile Asn Pro Ile Ile Pro
1               5                   10                  15

Phe Thr Gly Pro Ile Gln Gly Gly Leu Gln Glu Gly Leu Gln Val Thr
            20                  25                  30

Leu Gln Gly Thr Thr Lys Ser Phe Ala Gln Arg Phe Val Val Asn Phe
        35                  40                  45

Gln Asn Ser Phe Asn Gly Asn Asp Ile Ala Phe His Phe Asn Pro Arg
    50                  55                  60

Phe Glu Glu Gly Gly Tyr Val Val Cys Asn Thr Lys Gln Asn Gly Gln
65                  70                  75                  80

Trp Gly Pro Glu Glu Arg Lys Met Gln Met Pro Phe Gln Lys Gly Met
                85                  90                  95

Pro Phe Glu Leu Cys Phe Leu Val Gln Arg Ser Glu Phe Lys Val Met
            100                 105                 110

Val Asn Lys Lys Phe Phe Val Gln Tyr Gln His Arg Val Pro Tyr His
        115                 120                 125

Leu Val Asp Thr Ile Ala Val Ser Gly Cys Leu Lys Leu Ser Phe Ile
    130                 135                 140

Thr Phe Gln Thr Gln Asp Phe Arg Pro Ala His Gln Ala Pro Met Ala
145                 150                 155                 160

Gln Thr Thr Ile His Met Val His Ser Thr Pro Gly Gln Met Phe Ser
                165                 170                 175

Thr Pro Gly Ile Pro Pro Val Val Tyr Pro Thr Pro Ala Tyr Thr Ile
            180                 185                 190

Pro Phe Tyr Thr Pro Ile Pro Asn Gly Leu Tyr Pro Ser Lys Ser Ile
        195                 200                 205

Met Ile Ser Gly Asn Val Leu Pro Asp Ala Thr Arg Phe His Ile Asn
    210                 215                 220
```

```
Leu Arg Cys Gly Gly Asp Ile Ala Phe His Leu Asn Pro Arg Phe Asn
225                 230                 235                 240

Glu Asn Ala Val Val Arg Asn Thr Gln Ile Asn Asn Ser Trp Gly Gln
            245                 250                 255

Glu Glu Arg Ser Leu Leu Gly Arg Met Pro Phe Ser Arg Gly Gln Ser
        260                 265                 270

Phe Ser Val Trp Ile Ile Cys Glu Gly His Cys Phe Lys Val Ala Val
            275                 280                 285

Asn Gly Gln His Met Cys Glu Tyr Tyr His Arg Leu Lys Asn Leu Gln
290                 295                 300

Asp Ile Asn Thr Leu Glu Val Ala Gly Asp Ile Gln Leu Thr His Val
305                 310                 315                 320

Gln Thr

<210> SEQ ID NO 18
<211> LENGTH: 353
<212> TYPE: PRT
<213> ORGANISM: Mouse

<400> SEQUENCE: 18

Met Ala Leu Phe Ser Ala Gln Ser Pro Tyr Ile Asn Pro Ile Ile Pro
1               5                   10                  15

Phe Thr Gly Pro Ile Gln Gly Gly Leu Gln Glu Gly Leu Gln Val Thr
            20                  25                  30

Leu Gln Gly Thr Thr Lys Ser Phe Ala Gln Arg Phe Val Val Asn Phe
        35                  40                  45

Gln Asn Ser Phe Asn Gly Asn Asp Ile Ala Phe His Phe Asn Pro Arg
50                  55                  60

Phe Glu Glu Gly Gly Tyr Val Val Cys Asn Thr Lys Gln Asn Gly Gln
65                  70                  75                  80

Trp Gly Pro Glu Glu Arg Lys Met Gln Met Pro Phe Gln Lys Gly Met
            85                  90                  95

Pro Phe Glu Leu Cys Phe Leu Val Gln Arg Ser Glu Phe Lys Val Met
            100                 105                 110

Val Asn Lys Lys Phe Phe Val Gln Tyr Gln His Arg Val Pro Tyr His
            115                 120                 125

Leu Val Asp Thr Ile Ala Val Ser Gly Cys Leu Lys Leu Ser Phe Ile
130                 135                 140

Thr Phe Gln Asn Ser Ala Ala Pro Val Gln His Val Phe Ser Thr Leu
145                 150                 155                 160

Gln Phe Ser Gln Pro Val Gln Phe Pro Arg Thr Pro Lys Gly Arg Lys
            165                 170                 175

Gln Lys Thr Gln Asn Phe Arg Pro Ala His Gln Ala Pro Met Ala Gln
            180                 185                 190

Thr Thr Ile His Met Val His Ser Thr Pro Gly Gln Met Phe Ser Thr
            195                 200                 205

Pro Gly Ile Pro Pro Val Val Tyr Pro Thr Pro Ala Tyr Thr Ile Pro
210                 215                 220

Phe Tyr Thr Pro Ile Pro Asn Gly Leu Tyr Pro Ser Lys Ser Ile Met
225                 230                 235                 240

Ile Ser Gly Asn Val Leu Pro Asp Ala Thr Arg Phe His Ile Asn Leu
            245                 250                 255

Arg Cys Gly Gly Asp Ile Ala Phe His Leu Asn Pro Arg Phe Asn Glu
            260                 265                 270
```

```
Asn Ala Val Val Arg Asn Thr Gln Ile Asn Asn Ser Trp Gly Gln Glu
        275                 280                 285

Glu Arg Ser Leu Leu Gly Arg Met Pro Phe Ser Arg Gly Gln Ser Phe
290                 295                 300

Ser Val Trp Ile Ile Cys Glu Gly His Cys Phe Lys Val Ala Val Asn
305                 310                 315                 320

Gly Gln His Met Cys Glu Tyr Tyr His Arg Leu Lys Asn Leu Gln Asp
                325                 330                 335

Ile Asn Thr Leu Glu Val Ala Gly Asp Ile Gln Leu Thr His Val Gln
                340                 345                 350

Thr

<210> SEQ ID NO 19
<211> LENGTH: 355
<212> TYPE: PRT
<213> ORGANISM: Homo sapiens

<400> SEQUENCE: 19

Met Ala Phe Ser Gly Ser Gln Ala Pro Tyr Leu Ser Pro Ala Val Pro
1               5                   10                  15

Phe Ser Gly Thr Ile Gln Gly Gly Leu Gln Asp Gly Leu Gln Ile Thr
                20                  25                  30

Val Asn Gly Thr Val Leu Ser Ser Ser Gly Thr Arg Phe Ala Val Asn
                35                  40                  45

Phe Gln Thr Gly Phe Ser Gly Asn Asp Ile Ala Phe His Phe Asn Pro
            50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
    130                 135                 140

Ile Ser Phe Gln Asn Pro Arg Thr Val Pro Val Gln Pro Ala Phe Ser
145                 150                 155                 160

Thr Val Pro Phe Ser Gln Pro Val Cys Phe Pro Pro Arg Pro Arg Gly
                165                 170                 175

Arg Arg Gln Lys Pro Pro Gly Val Trp Pro Ala Asn Pro Ala Pro Ile
            180                 185                 190

Thr Gln Thr Val Ile His Thr Val Gln Ser Ala Pro Gly Gln Met Phe
        195                 200                 205

Ser Thr Pro Ala Ile Pro Pro Met Met Tyr Pro His Pro Ala Tyr Pro
    210                 215                 220

Met Pro Phe Ile Thr Thr Ile Leu Gly Gly Leu Tyr Pro Ser Lys Ser
225                 230                 235                 240

Ile Leu Leu Ser Gly Thr Val Leu Pro Ser Ala Gln Arg Phe His Ile
                245                 250                 255

Asn Leu Cys Ser Gly Asn His Ile Ala Phe His Leu Asn Pro Arg Phe
            260                 265                 270

Asp Glu Asn Ala Val Val Arg Asn Thr Gln Ile Asp Asn Ser Trp Gly
        275                 280                 285
```

-continued

```
Ser Glu Glu Arg Ser Leu Pro Arg Lys Met Pro Phe Val Arg Gly Gln
    290                 295                 300

Ser Phe Ser Val Trp Ile Leu Cys Glu Ala His Cys Leu Lys Val Ala
305                 310                 315                 320

Val Asp Gly Gln His Leu Phe Glu Tyr Tyr His Arg Leu Arg Asn Leu
                325                 330                 335

Pro Thr Ile Asn Arg Leu Glu Val Gly Gly Asp Ile Gln Leu Thr His
            340                 345                 350

Val Gln Thr
        355
```

TIM-3 LIGANDS AND METHODS THEREOF

CROSS-REFERENCE TO RELATED APPLICATIONS

This application claims the benefit of the filing date of U.S. Application No. 60/508,319, filed Oct. 3, 2003, entitled "TIM-3 LIGANDS AND METHODS THEREOF." The entire teachings of the referenced application are incorporated by reference herein.

GOVERNMENT FUNDING

Work described herein was funded by grant numbers 1RO1NS045937-01, 2R01NS35685-06, 2R37NS30843-11, 1RO1AI44880-03, 2P01AI39671-07, 1PO1NS38037-04 and 1F31GM20927-01 from the National Institutes of Health. Accordingly, the United States government has certain rights in the invention.

BACKGROUND OF THE INVENTION

Upon stimulation by antigen, naïve $CD4^+$ T helper cells develop into two main effector pathways, Th1 and Th2 cells, defined by their cytokine profiles (Mosmann et al. *J Immunol* 136, 2348-2357 (1986), Mosmann et al. *Immunol Today* 19, 138-146 (1996), Abbas, et al. *Nature* 383, 787-793 (1996)).

Th1 cells produce cytokines (interferon (IFN-γ, interleukin (IL)-2, tumor-necrosis factor TNF-α and lymphotoxin) that are most frequently associated with cell-mediated immune responses against intracellular pathogens. The pathological consequences of an inappropriate Th1 response are delayed type hypersensitivity (DTH) reactions (Sher, et al. *Annu Rev Immunol.* 10, 385-409 (1992)), induction of organ-specific autoimmune disease (Liblau, et al. *Immunol Today* 16, 34-38 (1995)), rheumatoid arthritis, inflammatory bowel disease (IBD), type I diabetes multiple sclerosis, and allograft rejection.

Th2 cells produce cytokines (IL-4, IL-10 and IL-13) necessary for the clearance of extracellular helminthic infections, and inappropriate Th2 cell activation promotes the onset of atopic and allergic diseases (Abbas, et al. *Nature* 383, 787-793 (1996), Sher, et al. *Annu Rev Immunol.* 10, 385-409 (1992)), such as allergic asthma.

In addition to their distinct roles in disease, the two T helper subsets also cross-regulate each other's expansion and functions. Thus, preferential induction of Th2 cells inhibits autoimmune diseases (Nicholson, L., et al. *Immunity* 3, 397-405 (1995), Kuchroo, et al. *Cell* 80, 707-718 (1995)), while predominant induction of Th1 cells can regulate asthma, atopy and allergies (Lack, et al. *J Immunol* 152, 2546-2554 (1994); Hofstra, et al. *J Immunol* 161, 5054-5060 (1998)).

Applicants have recently identified a novel cell surface protein, Tim-3, which is expressed on Th1 but not Th2 cells. Tim-3 (T cell Immunoglobulin and Mucin domain containing molecule) is a type I membrane protein of 281 amino acids whose extracellular domain comprises of an IgV-like domain followed by a mucin-like region. The human orthologue of Tim-3 shares 63% amino acid identity with murine Tim-3. Tim-3 is polymorphic and, along with other Tim family members, has been linked to murine asthma (McIntire, J. et al. *Nat Immunol* 2, 1109-1116 (2001)). In addition, the Tim gene family region is syntenic with a major asthma susceptibility locus in humans (McIntire, J. et al. *Nat Immunol* 2, 1109-1116 (2001)). These studies underscore the importance of Tim-3 and the Tim gene family in regulation of immune-mediated diseases.

In vivo during an ongoing immune response, administration of anti-Tim-3-antibody increased macrophage activation and expansion (Monney, L. et al. *Nature* 415, 536-541 (2002). Anti-Tim-3 antibody treatment also exacerbated the autoimmune disease experimental autoimmune encephalomyelitis (EAE), significantly increasing mortality and causing enhanced demyelination and infiltration of activated macrophages to the central nervous system (CNS).

Accordingly, a need remains to identify agents which modulate tim-3 function and thus modulate immune responses. Some aspects of the present invention provide such agents, methods to identify such agents, and methods of modulating immune responses using such agents.

SUMMARY OF THE INVENTION

The invention provides novel polypeptides, nucleic acids and compositions, including those useful in modulating immune responses. The invention further provides methods of modulating immune responses in a subject in need thereof, and methods of identifying agents which may be used to modulate immune responses.

The invention provides an isolated polypeptide comprising a tim-3 IgV domain and a tim-3 intracellular domain, wherein the polypeptide does not comprise a tim-3 mucin domain or a tim-3 transmembrane domain. The invention also provides the nucleic acids which encode such polypeptides.

The invention also provides an isolated nucleic acid which hybridizes under high stringency conditions to a nucleic acid encoding soluble tim-3 but which does not hydridize under high stringency conditions to a nucleic acid encoding full-length tim-3. Such nucleic acid is useful, among other things, to modulate immune responses.

Furthermore, the invention provides a pharmaceutical package comprising (i) a polypeptide which comprises the IgV domain of tim-3; and (ii) instructions for administering the composition to a subject for treating a hyperplastic condition.

The invention additionally provides an isolated antibody or fragment thereof which binds to a polypeptide having an amino acid sequence set forth in SEQ ID NO: 2 but which does not bind to a polypeptide having the amino acid sequence set forth in SEQ ID NO: 13. Likewise, the invention provides an isolated antibody or fragment thereof which binds to a polypeptide having an amino acid sequence set forth in SEQ ID NO: 4 but which does not bind to a polypeptide having the amino acid sequence set forth in SEQ ID NO: 14.

The invention provides methods of modulating immune responses in a subject, such as immune tolerance in a subject, comprising administering to the subject a therapeutically effective amount of an agent that modulates tim-3 activity. The invention also provides methods for modulating immune responses, such as Th1 and Th2 responses, in a subject.

The invention further provides methods of identifying agents which modulate immune responses, and methods of identifying agents which modulate the binding interaction between tim-3 and its ligands, such as galectin-9.

The invention further provides agents for the manufacture of medicaments to treat any of the disorders described herein. Any methods disclosed herein for treating or preventing a disorder by administering an agent to a subject may be applied to the use of the agent in the manufacture of a medicament to treat that disorder. For example, in one specific embodiment, a tim-3IgV-HSA fusion protein may be used in the manufacture of a medicament for the treatment of Th2-mediated disorder, whereas a pegylated galectin-9 polypeptide may be used in the manufacture of a medicament for the treatment of a Th1-mediated disorder.

BRIEF DESCRIPTION OF THE DRAWINGS

FIG. 5 shows that Tim-3-Ig treatment in vivo inhibited induction of tolerance. SJL/J mice were immunized with PLP 139-151/CFA and concurrently given intraperitoneal injections of 500 mg soluble PLP 139-151 (or PBS as a control vehicle) to induce tolerance. Mice were injected intraperitoneally every other day from day 0-8 with 100 mg ex-Tim-3-Ig or hIgG as control. Mice were sacrificed on day 10, and lymph nodes were taken and cells ($2\times10^5$/well) cultured in vitro with increasing concentrations of PLP 139-151 peptide (data shown for 100 mg/ml PLP 139-151). Proliferation was measured in triplicate wells after 48 h by $^3$H-thymidine incorporation. Supernatants were taken from the in vitro cultures at 48 h, and cytokine ELISAs for IL-2, IL-4, IL-10 and IFN-g were performed. P values were obtained by student's t test. Legend: † $P<0.01$ when non-tolerized (PBS) hIgG group compared with tolerized (PLP) hIgG group. ¥ $P<0.01$ when tolerized (PLP) hIgG group compared with tolerized (PLP) Tim-3-Ig group. ‡ $P<0.01$ when non-tolerized (PBS) hIgG group compared with tolerized (PLP) hIgG group. ◇ $P<0.05$ when tolerized (PLP) hIgG group compared with tolerized (PLP) Tim-3-Ig group. § $P<0.5$ when non-tolerized (PBS) hIgG group compared with tolerized (PLP) hIgG group. $P<0.1$ when tolerized (PLP) hIgG group compared with tolerized (PLP) Tim-3-Ig group.

Figure 1A:
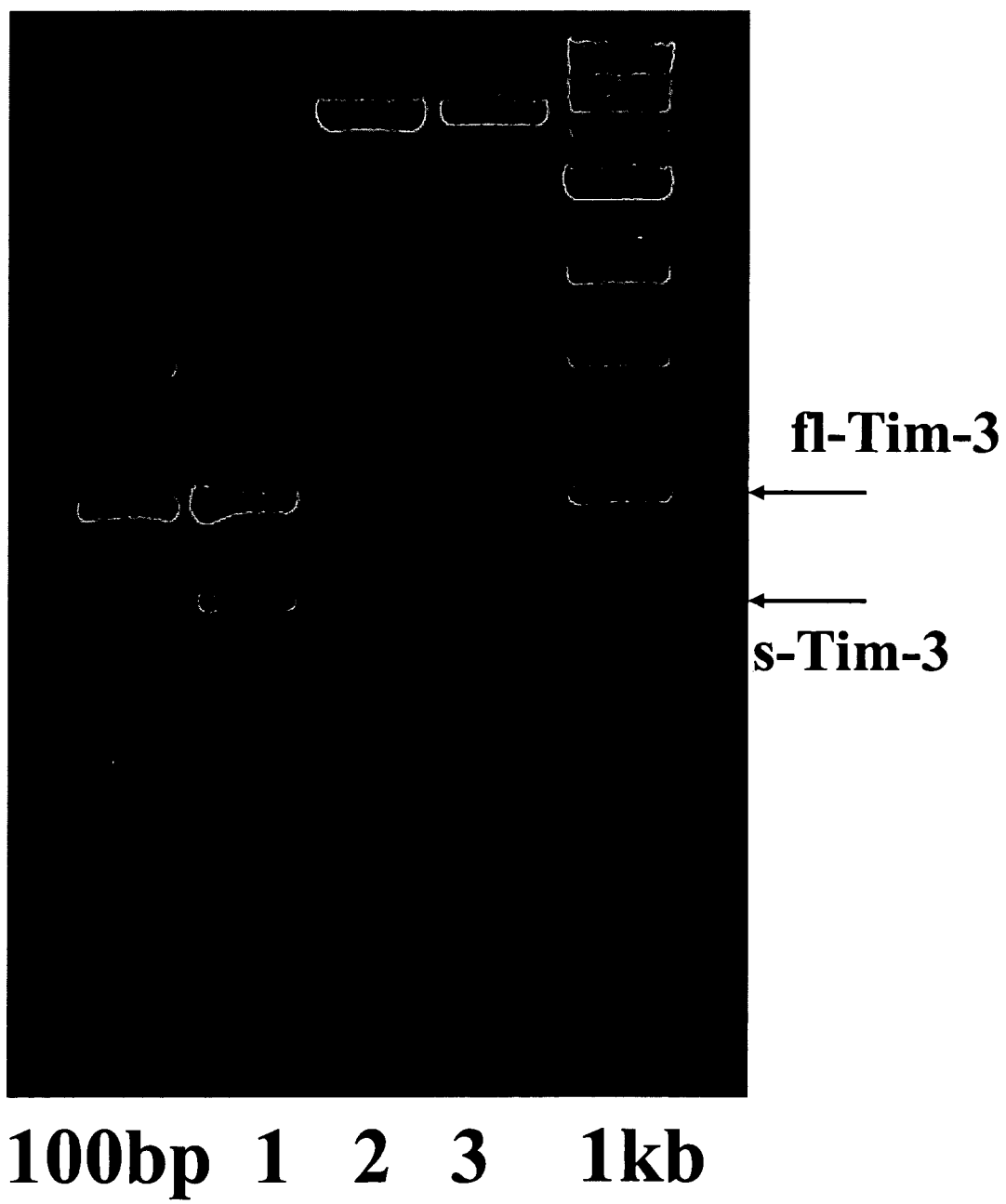
FIG. 1 shows the identification of alternatively spliced soluble form of Tim-3. (a) Full-length and alternatively spliced forms of Tim-3 were amplified from cDNA generated from concanavalin A-stimulated splenocytes. Primers were designed in the 5' and 3' UTR of the Tim-3 gene and subjected to RT-PCR. Products were resolved on a 1.2% agarose gel and visualized using ethidium bromide (lane 1). Amplicons of 800 bp and 1 kb were cloned into the pEF6 vector (lanes 2 & 3). In order to confirm the cloning, plasmid DNA was digested with the SmaI restriction endonuclease (New England Biolabs). Reactions were terminated with loading dye and run on a 1.2% agarose gel and visualized with ethidium bromide (lanes 2 and 3). Clones containing inserts of 1 kb or 800 bp were sequenced. Lane 1, con-A activated splenocytes cDNA amplified by PCR with Tim-3-F and Tim-3-R primer; Lane 2, 1 kb cloned product, fl-Tim-3; Lane 3, 800 bp cloned product, s-Tim-3. (b) The predicted amino acid translation of the nucleotide sequence from the 1 kb amplicon conformed to the full-length form of Tim-3 (fl-Tim-3) consisting of signal peptide, IgV, mucin, transmembrane and cytoplasmic domains. Alignment of the amino acid translation of the nucleotide sequence from the 800 bp amplicon with fl-Tim-3 demonstrated a novel isoform (s-Tim-3) containing only the signal peptide, IgV and cytoplasmic domains. (c) Schematic representation of Tim-3 gene structure, and the alternatively spliced transcripts corresponding to fl-Tim-3 and s-Tim-3. The murine Tim-3 gene consists of 7 exons. The fl-Tim-3 transcript is comprised of all 7 exons. In contrast, the s-Tim-3 transcript is comprised of only exon 1, exon 2, exon 6 and exon 7. Coding region signal peptide, IgV, mucin, transmembrane (tm) and cytoplasmic domains of the transcript are shown.

DETAILED DESCRIPTION OF THE INVENTION (i) Overview

The present invention relates to reagents, compositions and methods for modulating the activation of Th1 cells, and for modulating immune responses, including but not limited to immune tolerance and transplantation tolerance.

The invention derives in part from the discovery of a novel splice isoform of tim-3, in mice and humans, encoding a soluble form of tim-3 comprising the IgV domain and the intracellular domain of tim-3, but lacking the mucin and the transmembrane domain. The invention provides isolated nucleic acids encoding the tim-3 soluble isoform or fragments thereof. The invention additionally provides fusion proteins which comprise soluble tim-3 and another polypeptide, such as the IgFc domain of immunoglobulins. Furthermore, the invention provides reagents which modulate the expression and/or function of the soluble tim-3 protein but not that of full-length tim-3.

The invention also derives in part from the discovery that blocking the activation of tim-3 by a ligand, results in an increase in Th1 cell activation, including but not limited to, Th1 cell proliferation and production of the cytokines IL-2 and IFN-γ. Furthermore, the invention derives from the discovery that tim-3 activity, such as a tim-3 interaction with a ligand, is required to establish immune tolerance and transplantation tolerance in a mouse model. In addition, the invention also derives from the discovery that galectin-9 is a tim-3 ligand. Galectin-9 is a member of galectin family which is ubiquitously expressed on a variety of cell types and which binds β-galactoside. Two forms of galectin-9 have been described in humans, a long and a short form. The human short isoform lacks 31 amino acids that are located between the N-terminal carbohydrate-binding domain and the link peptide in the long isoform (residues 149-180 of the human long isoform). The human and mouse short galectin-9 amino acid sequences are listed in SEQ ID NO: 10 and 17 respectively, while their corresponding DNA coding sequences are listed as SEQ ID NO: 9 and 16. The mouse and human long galectin-9 amino acid sequences are listed in SEQ ID NO: 18 and 19 respectively.

In the human short galectin-9 isoform, the N- and C-terminal carbohydrate recognition domains (CRD) stretch from 16-146 and from 195-322, respectively. these are joined by a linker peptide stretching from 149-174 (See Genbank Accession No. NP_002299). The two CRDs in the human long isoform stretch from residues 16-146 and 227-354, respectively.

The Galectin-9 amino acid and DNA coding sequences are also described in U.S. Pat. Nos. 6,468,768 and 6,027,916, hereby incorporated by reference. The invention thus provides methods for modulating immune responses, such as increasing or decreasing Th1 and/or Th2 responses, and also provides methods for increasing or decreasing immune tolerance and transplantation tolerance.

One aspect of the invention provides an isolated polypeptide comprising a tim-3 IgV domain and a tim-3 intracellular domain, wherein the polypeptide does not comprise a tim-3 mucin domain or a tim-3 transmembrane domain. In specific embodiments, the polypeptide is a mammalian polypeptide, such as a human or a mouse polypeptide. In one embodiment, the tim-3 IgV domain comprises amino acids 22-131 of SEQ ID NO: 13 or 22-132 of SEQ ID NO: 14. In one embodiment, the tim-3 intracellular domain comprises amino acids 226-301 of SEQ ID NO: 13 or amino acids 217-281 of SEQ ID NO: 14. In some embodiments, the isolated polypeptide further comprises the Fc domain of an immunoglobulin or other carrier protein.

The invention further provides compositions comprising the isolated polypeptide described herein. In one embodiment, the compositions further comprise a pharmaceutically acceptable carrier. The invention also provides nucleic acids encoding the polypeptides described herein. The invention also provides an isolated nucleic acid which hybridizes under high stringency conditions to a nucleic acid encoding soluble tim-3 but which does not hydridize under high stringency conditions to a nucleic acid encoding full-length tim-3, such as a nucleic acid comprising the sequence set forth in SEQ ID NO: 5.

Another aspect of the invention provides pharmaceutical packages. A specific aspect provides a pharmaceutical package comprising (i) a polypeptide which comprises the IgV domain of tim-3; and (ii) instructions for administering the composition to a subject for treating a hyperplastic condition or for treating a Th2-mediated condition. In a specific embodiment, the hyperplastic condition is renal cell cancer, Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, testicular cancer, Hodgkin's lymphoma, gastrointestinal cancer, or stomach cancer.

In a specific embodiment, the pharmaceutical package comprising (i) a polypeptide which comprises a galectin-9 polypeptide; and (ii) instructions for administering the composition to a subject for treating an autoimmune disorder.

The invention further provides immunological reagents. In specific aspect provides an isolated antibody or fragment thereof which binds to a polypeptide having an amino acid sequence set forth in SEQ ID NO: 2 but which does not bind to a polypeptide having the amino acid sequence set forth in SEQ ID NO: 13, or that binds to a polypeptide having an amino acid sequence set forth in SEQ ID NO: 4 but which does not bind to a polypeptide having the amino acid sequence set forth in SEQ ID NO: 14, such as an antibody that binds to a polypeptide comprising an amino acid sequence set forth in SEQ ID NO: 6 or 8. In preferred embodiments, the antibody is a monoclonal antibody. The invention further provides hybridoma cell lines which secretes said monoclonal antibodies.

On aspect of the invention provides methods of modulating immune responses in a subject. One aspect of the invention provides a method of modulating an immune response in a subject in need thereof, the method comprising administering to the subject a therapeutically effective amount of an agent that modulates tim-3 activity. In one preferred embodiment, modulating an immune response comprises increasing a Th1 response or decreasing a Th2 response and wherein the agent decreases tim-3 activity.

In one embodiment of the methods described herein for increasing a Th1 response or decreasing a Th2 response by decreasing tim-3 activity, the subject is afflicted with a hyperplastic condition or with a Th2-mediated disorder, such as asthma, an allergy, allergic rhinitis, gastrointestinal allergy, food allergy, eosinophilia, conjunctivitis or glomerulonephritis. In another specific embodiment, the agent inhibits expression of soluble tim-3. The agent that decreases tim-3 activity may be an antibody or a fragment thereof, such as an antibody that binds to tim-3, such as one that binds to the extracellular domain of tim-3, such as to amino acids 30-128 of SEQ ID NO: 13.

In one embodiment of the methods described herein for increasing a Th1 response or decreasing a Th2 response by decreasing tim-3 activity, the agent reduces the binding of galectin-9 to tim-3. In a specific embodiment, the agent comprises a polypeptide comprising (i) amino acids 30-128 of SEQ ID NO: 13; or (iii) an amino acid sequence that is at least 90% identical to amino acids 30-128 of SEQ ID NO: 13. In some embodiments, the polypeptide agents are modified to increase their in vivo stability, such as by pegylation or by fusion to a plasma protein, such as human serum albumin or an Fc domain of an immunoglobulin. In a specific embodiment, the agent comprises a polypeptide comprising the IgV domain of tim-3, the intracellular domain of tim-3, and the Fc domain of an immunoglobulin, but does not contain comprise the mucin domain of tim-3 or the transmembrane domain of tim-3. In a specific embodiment, the agent decreases the expression level of a tim-3 polypeptide or a galectin-9 polypeptide. In a specific embodiment, the agent is an double stranded RNA antisense oligonucleotide. In a specific embodiment, the agent inhibits binding of full-length tim-3 to galectin-9, such as one that inhibits binding of (i) a polypeptide comprising amino acids 30-128 of SEQ ID NO: 13; to (ii) galectin-9 (e.g. SED ID NO: 10 or in SED ID NO: 19). In another embodiment, the agent that reduces tim-3/galectin-9 binding comprises a carbohydrate, such as lactose, β-galactoside, a glycosylated polypeptide, pectin or modified pectin.

In one preferred embodiment of the methods for modulating immune responses in a subject, modulating an immune response comprises decreasing a Th1 response or increasing a Th2 response, and wherein the agent increases tim-3 activity. In a specific embodiment, the subject is afflicted with an autoimmune disease, with host versus graft disease (HVGD), or the subject is an organ transplant recipient.

In one embodiment of the methods described herein for decreasing a Th1 response or increasing a Th2 response by increasing tim-3 activity, the agent is an antibody, an antibody fragment, or a polypeptide. In a specific embodiment, the antibody is a bispecific antibody specific for tim-3 and galectin-9. In another specific embodiment, the binding of the agent to tim-3 increases the phosphorylation of the intracellular domain of tim-3. In another specific embodiment, the agent is a tim-3 ligand, such as a recombinant version of a naturally occurring ligand. In another specific embodiment, the binding of the tim-3 ligand to full-length tim-3 increases the phosphorylation of the intracellular domain of tim-3. In another specific embodiment, the tim-3 ligand comprises a galectin-9 polypeptide. In another specific embodiment, the agent is a polypeptide comprising at least one of the two carbohydrate recognition domains (CRD) of galectin-9. In another specific embodiment, the polypeptide comprises two CRD domains of galectin-9. In another specific embodiment, the agent comprises a polypeptide comprising an amino acid sequence which is at least 80%, 90% or 95% identical to the amino acid sequence set forth in SEQ ID NO: 10 or SEQ ID NO: 18.

One aspect of the invention provides methods of identifying agents that modulates the binding between a tim-3 polypeptide and a galectin-9 polypeptide. One specific aspect provides a method of identifying an agent that modulates the binding between a tim-3 polypeptide and a galectin-9 polypeptide, the method comprising: (a) contacting the tim-3 polypeptide and the galectin-9 polypeptide in the presence of a test agent; and (b) determining the effect of the test agent on the binding of the tim-3 polypeptide and the galectin-9 polypeptide; thereby identifying a agent that modulates the binding between a tim-3 polypeptide and a galectin-9 polypeptide.

Another aspects provides a method of identifying an agent that modulates an immune response, such as a method comprising (a) contacting the tim-3 polypeptide and the galectin-9 polypeptide in the presence of a test agent; and (b) determining the effect of the test agent on the binding of the tim-3 polypeptide and the galectin-9 polypeptide. In some embodiments, step (b) comprises comparing formation of a tim-3/galectin-9 complex in the presence of the test agent with an appropriate control. An appropriate control may comprise the formation of a complex between the first polypeptide and the second polypeptide in the absence of the test agent. The agent may increases or decrease the binding between tim-3 and galectin-9, and may comprise a small compound, an antibody or a polypeptide. In some embodiments of the methods for identifying an agent that modulates an immune response, the immune response is a Th1 immune response or a Th2 immune response.

The methods for identifying an agent that modulates an immune response or to identify agents that modulates the binding between a tim-3 polypeptide and a galectin-9 polypeptide may be carried out in vitro or in vivo. In a specific embodiment, the tim-3 polypeptide or the galectin-9 polypeptide or both are expressed in a cell. In a specific embodiment, detecting the formation of the complex comprises detecting the expression of a reporter gene, wherein the expression of the reporter gene is dependent on the formation of the complex. In another specific embodiment, the tim-3 polypeptide or the galectin-9 polypeptide or both are labeled with a fluorescent molecule. In another specific embodiment, the galectin-9 polypeptide in the foregoing methods comprises (i) amino acids 1-323 of SEQ ID NO: 10; or (ii) amino acids 1-355 of SEQ ID NO: 19; or (iii) an amino acid sequence that is at least 90% identical to amino acids 1-323 of SEQ ID NO: 10; (iii) an amino acid sequence that is at least 90% identical to amino acids 1-355 of SEQ ID NO: 19. In another specific embodiment, the tim-3 polypeptide of the foregoing methods comprises (i) amino acids 30-128 of SEQ ID NO: 13; or (ii) an amino acid sequence that is at least 90% identical to amino acids 30-128 of SEQ ID NO: 13.

The invention further provides a method of conducting a drug discovery business comprising: (a) identifying compounds that affect the binding between tim-3 and galectin-9; (b) conducting therapeutic profiling of compounds identified in step (a), or further analogs thereof, for efficacy and toxicity in animals; and (c) formulating a pharmaceutical preparation including one or more compounds identified in step (b) as having an acceptable therapeutic profile. The invention further provides a method of conducting a drug discovery business comprising: (a) identifying compounds that affect the binding between tim-3 and galectin-9; (b) optionally conducting therapeutic profiling of compounds identified in step (a), or further analogs thereof, for efficacy and toxicity in animals; and (c) licensing, to a third party, the rights for further drug development and/or sales for compounds identified in step (a), or analogs thereof. A specific embodiment further comprises collecting royalties based on sales of said compounds identified in step (a) or analogs thereof.

The invention further provides method of increasing tim-3 activity, comprising contacting a cell which expresses soluble tim-3 with an amount of a double stranded RNA sufficient to decrease the expression of soluble tim-3, wherein the double stranded RNA does not inhibit the expression of full-length tim-3 in the cell, thereby increasing tim-3 activity. In a specific embodiment, the double stranded RNA hybridizes under high stringency conditions to a nucleic acid comprising SEQ ID NO: 1 but does not hybridize under high stringency conditions to a nucleic acid comprising SEQ ID NO: 11. In another specific embodiment, the double stranded RNA comprises the nucleic acid sequence set forth in SEQ ID NO: 15. In another specific embodiment, the double stranded RNA is an siRNA or a hairpin RNA. In another specific embodiment, the contacting is effected by administering the double stranded RNA to a subject.

The invention further provides a method of detecting soluble tim-3 gene expression comprising detecting the presence of a nucleic acid encoding soluble tim-3, wherein the detection of a nucleic acid encoding the soluble tim-3 indicates soluble tim-3 gene expression.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (D. M. Weir and C. C. Blackwell, eds., 1986); *Manipulating the Mouse Embryo,* (Cold Spring Harbor Laboratory Press, Cold Spring Harbor, N.Y., 1986). The contents of these reference is hereby incorporated by reference in their entirety.

(2) Definitions

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The terms "polypeptide" and "protein" are used interchangeably herein. The term "preventing" is art-recognized, and when used in relation to a condition, such as a local recurrence (e.g., pain), a disease such as cancer, a syndrome complex such as heart failure or any other medical condition, is well understood in the art, and includes administering, prior to onset of the condition, a composition that reduces the frequency of, reduces the severity of, or delays the onset of symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the frequency of, reducing the severity of, or alternatively delaying, pain sensations experienced by subjects in a treated population versus an untreated control population.

The term "effective amount" as used herein is defined as an amount effective, at dosages and for periods of time necessary to achieve the desired result. The effective amount of a compound of the invention may vary according to factors such as the disease state, age, sex, and weight of the animal. Dosage regimens may be adjusted to provide the optimum therapeutic response. For example, several divided doses may be administered daily or the dose may be proportionally reduced as indicated by the exigencies of the therapeutic situation.

A "subject" as used herein refers to any vertebrate animal, preferably a mammal, and more preferably a human. Examples of subjects include humans, non-human primates, rodents, guinea pigs, rabbits, sheep, pigs, goats, cows, horses, dogs, cats, birds, and fish.

A "variant" of a protein of interest, as used herein, refers to an amino acid sequence that is altered by one or more amino acids. The variant may have "conservative" changes, wherein a substituted amino acid has similar structural or chemical properties, (e.g., replacement of leucine with isoleucine). More rarely, a variant may have "nonconservative" changes (e.g., replacement of a glycine with a tryptophan). Similar minor variations may also include amino acid deletions or insertions, or both. Guidance in determining which amino acid residues may be substituted, inserted, or deleted without abolishing biological or immunological activity may be found using computer programs well known in the art, for example, DNASTAR® sequence analysis software.

As used herein, a "Th1-associated disorder" is a disease or condition associated with aberrant, e.g., increased Th1 cell activity (e.g., increased Th1 cell responses) or number compared to a reference, e.g., a normal control. Examples of Th1-associated disorders include, e.g., autoimmune disorders (e.g., multiple sclerosis, rheumatoid arthritis, type I diabetes and Crohn's disease.

As used herein, a "Th2-associated disorder" is a disease or condition associated with aberrant, e.g., increased Th2 cell activity (e.g., increased Th2 cell responses) or number compared to a reference, e.g., a normal control. Examples of Th2 disorders include, e.g., asthma, allergy, and disorders associated with antibody components (e.g., rheumatoid arthritis).

The term "analog" as used herein includes, but is not limited, to amino acid sequences containing one or more amino acid substitutions, insertions, and/or deletions from a reference sequence. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics. Amino acid insertions may consist of single amino acid residues or sequential amino acids ranging from 2 to 15 amino acids in length. Deletions may consist of the removal of one or more amino acids, or discrete portions from the amino acid sequence. The deleted amino acids may or may not be contiguous.

The term "recombinant" is used herein to mean any nucleic acid comprising sequences which are not adjacent in nature. A recombinant nucleic acid may be generated in vitro, for example by using the methods of molecular biology, or in vivo, for example by insertion of a nucleic acid at a novel chromosomal location by homologous or non-homologous recombination.

The term "agonist" refers to an agent that mimics or up-regulates (e.g., potentiates or supplements) the bioactivity of a protein, e.g., polypeptide X. An agonist may be a wild-type protein or derivative thereof having at least one bioactivity of the wild-type protein. An agonist may also be a compound that upregulates expression of a gene or which increases at least one bioactivity of a protein. An agonist may also be a compound which increases the interaction of a polypeptide with another molecule, e.g., a target peptide or nucleic acid.

The term "antagonist" refers to an agent that downregulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that downregulates expression of a gene or which reduces the amount of expressed protein present.

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like. For example, certain compounds discovered by the methods of the present invention may be administered in a sufficient amount to produce a reasonable benefit/risk ratio applicable to such treatment.

The term "subject in need of treatment for a disorder" is a subject diagnosed with that disorder or suspected of having that disorder.

Other technical terms used herein have their ordinary meaning in the art that they are used, as exemplified by a variety of technical dictionaries, such as the McGraw-Hill Dictionary of Chemical Terms and the Stedman's Medical Dictionary.

(3) Nucleic Acids

In certain aspects, the invention provides isolated and/or recombinant nucleic acids encoding human soluble tim-3 polypeptides or fragments thereof, such as, for example, SEQ ID NO: 1 and 5. One aspect of the invention provides an isolated nucleic acid comprising the nucleotide sequence set forth in SEQ ID NO: 1. SEQ ID NO: 1 is the DNA coding sequence of the human soluble tim-3 isoform. Human soluble tim-3 comprises the IgV domain (residues 22-131 of SEQ ID NO: 13) fused to the intracellular domain (residues 226-301 of SEQ ID NO: 13) of the human full-length tim-3. In one embodiment, the soluble human tim-3 nucleic acid provided by the present invention additionally encodes the signal sequence of full length tim-3 (amino acid residues 1-21 of SEQ ID NO: 13) at the N-terminus of the translated polypeptide. Another aspect of the invention provides an isolated nucleic acid encoding a human soluble tim-3 polypeptide comprising the amino acid sequence set forth in SEQ ID NO: 2.

Similarly, another aspect of the invention provides isolated and/or recombinant nucleic acids encoding mouse soluble tim-3 polypeptides or fragments thereof, such as, for example, SEQ ID NO: 3 and 7. One aspect of the invention provides an isolated nucleic acid comprising the nucleotide sequence set forth in SEQ ID NO: 3. SEQ ID NO: 3 is the DNA coding sequence of the mouse soluble tim-3 isoform. Mouse soluble tim-3 contains the IgV domain (residues 22-132 of SEQ ID NO: 14) fused to the intracellular domain (residues 217-281 of SEQ ID NO: 14) of the mouse full-length tim-3. In one embodiment, the mouse soluble tim-3 nucleic acids provided by the present invention additionally encode the signal sequence of full length tim-3 (amino acid residues 1-21 of SEQ ID NO: 14) at the N-terminus of the translated polypeptide. Another aspect of the invention provides an isolated nucleic acid encoding a mouse soluble tim-3 polypeptide comprising the amino acid sequence set forth in SEQ ID NO: 4.

Nucleic acids of the invention are further understood to include nucleic acids that comprise variants of SEQ ID NO: 1, 3, 5, and 7. Variant nucleotide sequences include sequences that differ by one or more nucleotides such as by substitutions, additions or deletions, such as allelic variants; and will, therefore, include coding sequences that differ from the nucleotide sequence of the coding sequence designated in SEQ ID NO: 1, 3, 5, and 7, e.g. due to the degeneracy of the genetic code. For example, nucleic acids encoding soluble tim-3 polypeptides may be nucleic acids comprising a sequence that is at least 90%, 95%, 99% or 100% identical to the sequence of SEQ ID NO: 1 and 3, or a sequence that encodes the polypeptide of SEQ ID NO: 2 and 4.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one preferred embodiment, the percent identity between two amino acid sequences is determined using the Needleman and Wunsch (J Mol. Biol. (48):444-453 (1970)) algorithm which has been incorporated into the GAP program in the GCG software package (available at the GCG web site), using either a Blossom 62 matrix or a PAM250 matrix.

In yet another embodiment, the percent identity between two nucleotide sequences is determined using the GAP program in the GCG software package (Devereux, J., et al., Nucleic Acids Res. 12(1):387 (1984)) (available at the GCG web site), using a NWSgapdna-CMP matrix. In another embodiment, the percent identity between two amino acid or nucleotide sequences is determined using the algorithm of E. Myers and W. Miller (CABIOS, 4:11-17 (1989)) which has been incorporated into the ALIGN program (version 2.0).

In other embodiments, variants will also include sequences that hybridize under highly stringent conditions to a coding sequence of a nucleic acid sequence designated in SEQ ID NO: 1 and 3. In one embodiment, the variant nucleotide sequences encode a soluble tim-3 polypeptide which lacks a mucin and a transmembrane domain. In another embodiment, the variant nucleotide sequences encode a soluble tim-3 polypeptide capable of binding tim-3 ligands, such as but not limited to galectin-9.

One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from SEQ ID NO: 1 and 3 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. One skilled in the art will appreciate that these variations in one or more nucleotides of the nucleic acids encoding a particular protein may exist among individuals of a given species due to natural allelic variation. Any and all such nucleotide variations and resulting amino acid polymorphisms are within the scope of this invention.

The invention also provides nucleic acids which hybridize under high stringency conditions to nucleic acids encoding soluble tim-3, and which do not encode the tim-3 transmembrane or the tim-3 mucin domain. In one embodiment, these nucleic acids encode at least the IgV domain of tim-3. These nucleic acids may encode soluble tim-3 proteins having mutations, deletions or insertions within the IgV or intracellular domains. In one embodiment, these nucleic acids encode polypeptides capable of binding to tim-3 ligands, such as galectin-9. In one embodiment, these nucleic acids encode fusion proteins comprising soluble tim-3, with or without mutations, and one or more domains from another protein(s), such as serum albumin or the Fc domain of an immunoglobulin.

The invention also provides nucleic acids which hybridize under high stringency or under physiological conditions to nucleic acids encoding soluble tim-3 but which do not hybridize under high stringency or under physiological conditions to nucleic acids encoding full-length tim-3. In one embodiment, the invention provides an isolated nucleic acid which hybridizes under high stringency conditions to a nucleic acid set forth in SEQ ID NO: 1 (encoding human soluble tim-3) but not to a nucleic acid set forth in SEQ ID NO 11 (encoding full-length human tim-3). In another embodiment, the invention provides an isolated nucleic acid which hybridizes under high stringency conditions to a nucleic acid set forth in SEQ ID NO: 3 (encoding mouse soluble tim-3) but not to a nucleic acid set forth in SEQ ID NO 12 (encoding full-length mouse tim-3). In a preferred embodiment, such isolated nucleic acids span the novel splice junction found in the soluble tim-3 cDNA that joins the IgV and intracellular domain-coding sequences of human and mouse tim-3. In another preferred embodiment, the nucleic acids have the nucleotide sequence set forth in SEQ ID NO: 5 and 7. These nucleic acids can be used in the methods described herein to detect nucleic acids encoding soluble tim-3, in detecting the presence of nucleic acids encoding tim-3 in a Th1 cell.

In certain aspects, nucleic acids encoding soluble tim-3 polypeptides and variants thereof may be used to increase soluble tim-3 expression in an organism or cell by delivery of the nucleic acid, such as by direct delivery. A nucleic acid therapy construct of the present invention can be delivered, for example, as an expression plasmid which, when transcribed in the cell, produces RNA which encodes a soluble tim-3 polypeptide.

The invention also provides methods of detecting soluble tim-3 gene expression comprising detecting the presence of a nucleic acid encoding soluble tim-3, wherein the detection of a nucleic acid encoding the soluble tim-3 indicates soluble tim-3 gene expression. In a preferred embodiment, the nucleic acid is an mRNA. Detection of an mRNA encoding soluble tim-3 can be done using methods commonly known in the art for the detection of mRNA molecules, including northern blots, PCR-amplification of reverse transcribed mRNA, or DNA microarrays. In another embodiment, soluble tim-3 gene expression is detected using an antibody, preferably on antibody that binds to soluble tim-3 but not to full-length tim-3.

(4) RNA Interference, Ribozymes and Antisense

In certain aspects, the invention relates to RNAi, ribozyme, antisense and other nucleic acid-related methods and compositions for manipulating (typically decreasing the gene expression) full-length tim-3, soluble tim-3 or tim-3 ligands. In one aspect of the invention, the methods and compositions are specific to only one form of tim-3, either the full-length or the soluble form. In another aspect of the invention, the tim-3 ligand that is manipulated is galectin-9.

Certain embodiments of the invention make use of materials and methods for effecting knockdown of one form of tim-3 or of its ligands, such as galectin-9, by means of RNA interference (RNAi). RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of in some instances as few as 21 to 22 base pairs in length. Furthermore, RNAi may be effected by introduction or expression of relatively short homologous dsR-NAs. Indeed the use of relatively short homologous dsRNAs may have certain advantages as discussed below.

Mammalian cells have at least two pathways that are affected by double-stranded RNA (dsRNA). In the RNAi (sequence-specific) pathway, the initiating dsRNA is first broken into short interfering (si) RNAs, as described above. The siRNAs have sense and antisense strands of about 21 nucleotides that form approximately 19 nucleotide si RNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length. The nonspecific effects occur because dsRNA activates two enzymes: PKR, which in its active form phosphorylates the translation initiation factor eIF2 to shut down all protein synthesis, and 2',5' oligoadenylate synthetase (2',5'-AS), which synthesizes a molecule that activates RNAse L, a nonspecific enzyme that targets all mRNAs. The nonspecific pathway may represents a host response to stress or viral infection, and, in general, the effects of the nonspecific pathway are preferably minimized under preferred methods of the present invention. Significantly, longer dsRNAs appear to be required to induce the nonspecific pathway and, accordingly, dsRNAs shorter than about 30 bases pairs are preferred to effect gene repression by RNAi (see Hunter et al. (1975) J Biol Chem 250: 409-17; Manche et al. (1992) Mol Cell Biol 12: 5239-48; Minks et al. (1979) J Biol Chem 254: 10180-3; and Elbashir et al. (2001) Nature 411: 494-8).

RNAi has been shown to be effective in reducing or eliminating the expression of a gene in a number of different organisms including *Caenorhabditis elegans* (see e.g. Fire et al. (1998) Nature 391: 806-11), mouse eggs and embryos (Wianny et al. (2000) Nature Cell Biol 2: 70-5; Svoboda et al. (2000) Development 127: 4147-56), and cultured RAT-1 fibroblasts (Bahramina et al. (1999) Mol Cell Biol 19: 274-83), and appears to be an anciently evolved pathway available in eukaryotic plants and animals (Sharp (2001) Genes Dev. 15: 485-90). RNAi has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass (2001) Nature 411: 428-9). In mammalian cells, siRNAs are effective at concentrations that are several orders of magnitude below the concentrations typically used in antisense experiments (Elbashir et al. (2001) Nature 411: 494-8).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides of the invention may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siR-NAs in the cell culture medium and within transfected cells (see Elbashi et al. (2001) Nature 411: 494-8). Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art (e.g. Expedite RNA phophoramidites and thymidine phosphoramidite (Proligo, Germany). Synthetic oligonucleotides are preferably deprotected and gel-purified using methods known in the art (see e.g. Elbashir et al. (2001) Genes Dev. 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence.

If tim-3 or galectin-9 is the target of the double stranded RNA, any of the above RNA species will be designed to include a portion of nucleic acid sequence represented in a tim-3 nucleic acid or a galectin-9 nucleic acid, such as, for example, a nucleic acid that hybridizes, under stringent and/or physiological conditions, to any of SEQ ID NO: 1, 3, 9, 10, 11 or 12 or complements thereof. If the goal is to reduce the activity of full-length tim-3, a double stranded RNA reagent that can specifically downregulate the expression of full-length tim-3 but not soluble tim-3 is preferred. Thus, the RNA reagent can decrease the level of full-length tim-3, while soluble tim-3 can titrate tim-3 ligands, such as galectin-9, to prevent their interaction with full-length tim-3. In this embodiment, the RNA species can be designed to include regions of the mRNA which encode the mucin or transmembrane domains, which are present in full-length tim-3 but absent in soluble tim-3.

A related aspect of the invention provides a method of increasing tim-3 activity by inhibiting expression of soluble tim-3, comprising contacting a cell which expresses soluble tim-3 with an amount of a double stranded RNA sufficient to inhibit the expression of soluble tim-3, wherein the double stranded RNA does not inhibit expression of full-length tim-3. In one embodiment, the double stranded RNA hybridizes under high stringency conditions to a nucleic acid comprising SEQ ID NO: 1 but does not hybridize under the same conditions to a nucleic acid comprising SEQ ID NO: 11. In another embodiment, the double stranded RNA hybridizes under physiological conditions to a nucleic acid comprising SEQ ID NO: 1 but does not hybridize under the same conditions to a nucleic acid comprising SEQ ID NO: 11. In a preferred embodiment, one strand of the double stranded RNA comprises the nucleic acid sequence set forth in SEQ ID NO: 15. The methods of the present invention can be performed in isolated cells expressing tim-3 or in a subject, preferably a human.

When the target is galectin-9, the RNA species may include a portion of nucleic acid sequence represented in a galectin-9 nucleic acid, such as, for example, a nucleic acid that hybridizes under stringent and/or physiological conditions to SEQ ID NO: 9 or to a complement thereof.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference. Messenger RNA (mRNA) is generally thought of as a linear molecule which contains the information for directing protein synthesis within the sequence of ribonucleotides, however studies have revealed a number of secondary and tertiary structures that exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see e.g. Jaeger et al. (1989) Proc. Natl. Acad. Sci. USA 86:7706 (1989); and Turner et al. (1988) Annu. Rev. Biophys. Biophys. Chem. 17:167). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerhead ribozyme compositions of the invention.

The dsRNA oligonucleotides may be introduced into the cell by transfection with an heterologous target gene using carrier compositions such as liposomes, which are known in the art—e.g. LIPOFECTAMINE™2000 transfection reagent (Life Technologies) as described by the manufacturer for adherent cell lines. Transfection of dsRNA oligonucleotides for targeting endogenous genes may be carried out using OLIGOFECTAMINE™ transfection reagent (Life Technologies). Transfection efficiency may be checked using fluorescence microscopy for mammalian cell lines after co-transfection of hGFP-encoding pAD3 (Kehlenback et al. (1998) J Cell Biol 141: 863-74). The effectiveness of the RNAi may be assessed by any of a number of assays following introduction of the dsRNAs. These include Western blot analysis using antibodies which recognize the tim-3 polypeptides, including the soluble and/or full-length forms, or tim-3 ligands, such as galectin-9, following sufficient time for turnover of the endogenous pool after new protein synthesis is repressed, reverse transcriptase polymerase chain reaction and Northern blot analysis to determine the level of existing target mRNA, such as full-length tim-3, soluble tim-3 or galectin-9 mRNA.

Further compositions, methods and applications of RNAi technology are provided in U.S. Pat. Nos. 6,278,039, 5,723,750 and 5,244,805, which are incorporated herein by reference.

Ribozyme molecules designed to catalytically cleave tim-3 or galectin-9 mRNA transcripts can also be used to prevent translation of subject tim-3 or galectin mRNAs (see, e.g., PCT International Publication WO90/11364, published Oct. 4, 1990; Sarver et al. (1990) Science 247:1222-1225 and U.S. Pat. No. 5,093,246). Ribozymes are enzymatic RNA molecules capable of catalyzing the specific cleavage of RNA. (For a review, see Rossi (1994) Current Biology 4: 469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to a tim-3 or a galectin-9 mRNA, and the well known catalytic sequence responsible for mRNA cleavage or a functionally equivalent sequence (see, e.g., U.S. Pat. No. 5,093,246, which is incorporated herein by reference in its entirety).

While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach (1988) Nature 334:585-591; and see PCT Appln. No. WO89/05852, the contents of which are incorporated herein by reference). Hammerhead ribozyme sequences can be embedded in a stable RNA such as a transfer RNA (tRNA) to increase cleavage efficiency in vivo (Perriman et al. (1995) Proc. Natl. Acad. Sci. USA, 92: 6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase III-mediated expression of tRNA fusion ribozymes are well known in the art (see Kawasaki et al. (1998) Nature 393: 284-9; Kuwabara et al. (1998) Nature Biotechnol. 16: 961-5; and Kuwabara et al. (1998) Mol. Cell 2: 617-27; Koseki et al. (1999) J Virol 73: 1868-77; Kuwabara et al. (1999) Proc Natl Acad Sci USA 96: 1886-91; Tanabe et al. (2000) Nature 406: 473-4). There are typically a number of potential hammerhead ribozyme cleavage sites within a given target cDNA sequence. Preferably the ribozyme is engineered so that the cleavage recognition site is located near the 5' end of the target mRNA- to increase efficiency and minimize the intracellular accumulation of non-functional mRNA transcripts. Furthermore, the use of any cleavage recognition site located in the target sequence encoding different portions of the C-terminal amino acid domains of, for example, long and short forms of target would allow the selective targeting of one or the other form of the target, and thus, have a selective effect on one form of the target gene product.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA. The tim-3 target mRNA include any of SEQ ID NO: 1, 3, 5 or 7. Galectin mRNA sequences include SEQ ID NO: 9.

In addition, ribozymes possess highly specific endoribonuclease activity, which autocatalytically cleaves the target sense mRNA. The present invention extends to ribozymes which hybridize to a sense mRNA encoding a tim-3 or galectin-9 protein such as a therapeutic drug target candidate gene, thereby hybridizing to the sense mRNA and cleaving it, such that it is no longer capable of being translated to synthesize a functional polypeptide product.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324: 429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

In certain embodiments, a ribozyme may be designed by first identifying a sequence portion sufficient to cause effective knockdown by RNAi. The same sequence portion may then be incorporated into a ribozyme. In this aspect of the invention, the gene-targeting portions of the ribozyme or RNAi are substantially the same sequence of at least 5 and preferably 6, 7, 8, 9, 10, 11, 12, 13, 14, 15, 16, 17, 18, 19 or 20 or more contiguous nucleotides of a tim-3 or galectin-9 nucleic acid.

In a long target RNA chain, significant numbers of target sites are not accessible to the ribozyme because they are hidden within secondary or tertiary structures (Birikh et al. (1997) Eur J Biochem 245: 1-16). To overcome the problem of target RNA accessibility, computer generated predictions of secondary structure are typically used to identify targets that are most likely to be single-stranded or have an "open" configuration (see Jaeger et al. (1989) Methods Enzymol 183: 281-306). Other approaches utilize a systematic approach to predicting secondary structure which involves assessing a huge number of candidate hybridizing oligonucleotides molecules (see Milner et al. (1997) Nat Biotechnol 15: 537-41; and Patzel and Sczakiel (1998) Nat Biotechnol 16: 64-8). Additionally, U.S. Pat. No. 6,251,588, the contents of which are hereby incorporated herein, describes methods for evaluating oligonucleotide probe sequences so as to predict the potential for hybridization to a target nucleic acid sequence. The method of the invention provides for the use of such methods to select preferred segments of a target mRNA sequence that are predicted to be single-stranded and, further, for the opportunistic utilization of the same or substantially identical target mRNA sequence, preferably comprising about 10-20 consecutive nucleotides of the target mRNA, in the design of both the RNAi oligonucleotides and ribozymes of the invention.

(5) Polypeptides

In certain aspects, the present disclosure makes available isolated and/or purified forms of the soluble tim-3 polypeptides, which are isolated from, or are otherwise substantially free of, other proteins which might normally be associated with the protein or a particular complex including the protein. In certain embodiments, a soluble tim-3 polypeptide is a polypeptide that comprises an amino acid sequence that is at least 90%, 95%, 97%, 99% or 100% identical to the amino acid sequence of SEQ ID NO: 2, 4, 6 or 8. The amino acid identity between two polypeptides can be determined by first aligning the two polypeptide sequences using an alignment algorithm, such as one based on the PAM250 matrix.

In certain embodiments, a soluble tim-3 polypeptide is a polypeptide comprising a portion of an amino acid sequence that is at least 90%, 95%, 97%, 99% or 100% identical to any of SEQ ID NO: 2, 4, 6 and 8, and preferably wherein said portion is a functional portion, such as a portion that is sufficient to modulate activation of Th1 cells or that is able to bind to a tim-3 ligand. In one embodiment, the portion comprises the IgV domain of tim-3. In some embodiments, the soluble tim-3 polypeptides contain conservative amino acid substitutions. In certain embodiments a soluble tim-3 polypeptide is a polypeptide obtained when a nucleic acid comprising a nucleic acid sequence at least 90%, 95%, 97%, 99% or 100% identical to a nucleic acid sequence of SEQ ID NO: 1, 3, 5 and 7 is expressed in cell. In certain embodiments a soluble tim-3 polypeptide is purified or partially purified.

In some embodiments, the IgV domain of soluble tim-3 comprises amino acids 22-131 of SEQ ID NO: 13. In other embodiments, it comprises amino acids 22-132 of SEQ ID NO: 14. In one embodiment, the intracellular domain of the soluble tim-3 polypeptides provided by the invention comprises amino acids 226-301 of SEQ ID NO: 13, while in another embodiment it comprises amino acids 217-281 of SEQ ID NO: 14.

The invention further encompasses fusion proteins comprising a soluble tim-3 polypeptide and a heterologous protein. In one embodiment, the soluble tim-3 protein comprises the IgV domain but lacks the mucin, transmembrane, and intracellular domains. In certain embodiments, fusion proteins comprising a soluble tim-3 polypeptide and an immunoglobulin element are provided. In one embodiment, the invention provides a polypeptide comprising the IgV domain of tim-3, the intracellular domain of tim-3, and the Fc domain of an immunoglobulin, wherein the protein does not contain the mucin domain of tim-3 or the transmembrane domain of tim-3. The tim-3 polypeptide can be mouse or human. An exemplary immunoglobulin element is a constant region like the Fc domain of a human IgG1 heavy chain (Browning et al., J. Immunol., 154, pp. 33-46 (1995)). Soluble receptor-IgG fusion proteins are common immunological reagents and methods for their construction are known in the art (see e.g., U.S. Pat. Nos. 5,225,538, 5,766,883 and 5,876,969), all of which are incorporated by reference. In some embodiments, soluble peptides of the present invention are fused to Fc variants.

In a related embodiment, the modified proteins of the invention comprise tim-3 and galectin-9 fusion proteins with an Fc region of an immunoglobulin. As is known, each immunoglobulin heavy chain constant region comprises four or five domains. The domains are named sequentially as follows: CH1-hinge-CH2-CH3(-CH4). The DNA sequences of the heavy chain domains have cross-homology among the immunoglobulin classes, e.g., the CH2 domain of IgG is homologous to the CH2 domain of IgA and IgD, and to the CH3 domain of IgM and IgE. As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain.

In one embodiment, the class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc γ or the homologous domains in any of IgA, IgD, IgE, or IgM.

Furthermore, it is contemplated that substitution or deletion of amino acids within the immunoglobulin heavy chain constant regions may be useful in the practice of the invention. One example would be to introduce amino acid substitutions in the upper CH2 region to create a Fc variant with reduced affinity for Fc receptors (Cole et al. (1997) J. IMMUNOL. 159:3613). One of ordinary skill in the art can prepare such constructs using well known molecular biology techniques.

In a further embodiment, the fusion proteins comprise a soluble tim-3 polypeptide and a second heterologous polypeptide to increase the in vivo stability of the fusion protein, or to modulate its biological activity or localization, or to facilitate purification of the fusion protein. Other exemplary heterologous proteins that can be used to generate tim-3 soluble fusion proteins include, but not limited to, glutathione-S-transferase (GST), an enzymatic activity such as alkaline phosphatase (AP), or an epitope tag such as hemagluttin (HA).

Preferably, stable plasma proteins, which typically have a half-life greater than 20 hours in the circulation, are used to construct fusions proteins with tim-3 or galectin-9. Such plasma proteins include but are not limited to: immunoglobulins, serum albumin, lipoproteins, apolipoproteins and transferrin. Sequences that can target the soluble tim-3 or galectin-9 molecules to a particular cell or tissue type may also be attached to the soluble tim-3 to create a specifically-localized soluble tim-3 fusion protein.

In one preferred embodiment, the invention provides tim-3 or galectin-9 fusions to albumin. As used herein, "albumin" refers collectively to albumin protein or amino acid sequence, or an albumin fragment or variant, having one or more functional activities (e.g., biological activities) of albumin. In particular, "albumin" refers to human albumin or fragments thereof (see EP 201 239, EP 322 094 WO 97/24445, WO95/23857) especially the mature form of human albumin, or albumin from other vertebrates o In particular, the albumin fusion proteins of the invention may include naturally occurring polymorphic variants of human albumin and fragments of human albumin (See WO95/23857), for example those fragments disclosed in EP 322 094 (namely HA (Pn), where n is 369 to 419). The albumin may be derived from any vertebrate, especially any mammal, for example human, cow, sheep, or pig. Non-mammalian albumins include, but are not limited to, hen and salmon. The albumin portion of the albumin fusion protein may be from a different animal than the tim-3 or galectin-9 protein.

In some embodiments, the albumin protein portion of an albumin fusion protein corresponds to a fragment of serum albumin. Fragments of serum albumin polypeptides include polypeptides having one or more residues deleted from the amino terminus or from the C-terminus. Generally speaking, an HA fragment or variant will be at least 100 amino acids long, preferably at least 150 amino acids long. The HA variant may consist of or alternatively comprise at least one whole domain of HA. Domains, of human albumin are described in U.S. Patent Publication No. 2004/0171123.

In certain embodiments, the invention includes nucleic acids encoding soluble tim-3 polypeptides In further embodiments, this invention also pertains to a host cell comprising soluble tim-3 polypeptides and related derivatives. The host cell may be any prokaryotic or eukaryotic cell. For example, a polypeptide of the present invention may be expressed in bacterial cells such as *E. coli*, insect cells (e.g., using a baculovirus expression system), yeast, or mammalian cells. In one embodiment, the soluble tim-3 polypeptide is made and secreted by a mammalian cell, and the soluble tim-3 polypeptide is purified from the culture medium. Other suitable host cells are known to those skilled in the art. Accordingly, some embodiments of the present invention further pertain to methods of producing the soluble tim-3 polypeptides.

It is also possible to modify the structure of the subject tim-3 polypeptides for such purposes as enhancing therapeutic or prophylactic efficacy, or stability (e.g., ex vivo shelf life and resistance to proteolytic degradation in vivo). Such modified polypeptides, when designed to retain at least one activity of the naturally-occurring form of the protein, are considered functional equivalents of the tim-3polypeptides described in more detail herein. Such modified polypeptides can be produced, for instance, by amino acid substitution, deletion, or addition.

For instance, it is reasonable to expect, for example, that an isolated replacement of a leucine with an isoleucine or valine, an aspartate with a glutamate, a threonine with a serine, or a similar replacement of an amino acid with a structurally related amino acid (i.e. conservative mutations) will not have a major effect on the biological activity of the resulting molecule. Conservative replacements are those that take place within a family of amino acids that are related in their side chains. Genetically encoded amino acids are can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W.H. Freeman and Co., 1981). Whether a change in the amino acid sequence of a polypeptide results in a functional homolog can be readily determined by assessing the ability of the variant polypeptide to produce a response in cells in a fashion similar to the wild-type protein. For instance, such variant forms of a tim-3 polypeptide can be assessed, e.g., for their ability to modulate the secretion of cytokines by Th1 cells, or their ability to bind to a tim-3 ligands, such as galectin-9. Polypeptides in which more than one replacement has taken place can readily be tested in the same manner.

In certain aspects, functional variants or modified forms of the subject soluble tim-3 and galectin-9 polypeptides include fusion proteins having at least a portion of the soluble polypeptide and one or more fusion domains. Well known examples of such fusion domains include, but are not limited to, polyhistidine, Glu-Glu, glutathione S transferase (GST), thioredoxin, protein A, protein G, and an immunoglobulin heavy chain constant region (Fc), maltose binding protein (MBP), which are particularly useful for isolation of the fusion proteins by affinity chromatography. For the purpose of affinity purification, relevant matrices for affinity chromatography, such as glutathione-, amylase-, and nickel- or cobalt-conjugated resins are used. Another fusion domain well known in the art is green fluorescent protein (GFP). Fusion domains also include "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation.

Some of the tim-3 or galectin-9 polypeptides provided by the invention, or used in the methods of the present invention, may further comprise post-translational modifications. Exemplary post-translational protein modification include phosphorylation, acetylation, methylation, ADP-ribosylation, ubiquitination, glycosylation, carbonylation, sumoylation, biotinylation or addition of a polypeptide side chain or of a hydrophobic group. As a result, the modified soluble polypeptides may contain non-amino acid elements, such as lipids, poly- or mono-saccharide, and phosphates.

In one specific embodiment of the present invention, modified forms of the subject tim-3 and galectin-9 soluble polypeptides comprise linking the subject soluble polypeptides to nonproteinaceous polymers. In one specific embodiment, the polymer is polyethylene glycol ("PEG"), polypropylene glycol, or polyoxyalkylenes, in the manner as set forth in U.S. Pat. Nos. 4,640,835; 4,496,689; 4,301,144; 4,670,417; 4,791,192 or 4,179,337.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented by the formula: $X-O(CH_2CH_2O)_{n-1}CH_2CH_2OH$ (1), where n is 20 to 2300 and X is H or a terminal modification, e.g., a $C_{1-4}$ alkyl. In one embodiment, the PEG of the invention terminates on one end with hydroxy or methoxy, i.e., X is H or $CH_3$ ("methoxy PEG"). A PEG can contain further chemical groups which are necessary for binding reactions; which results from the chemical synthesis of the molecule; or which is a spacer for optimal distance of parts of the molecule. In addition, such a PEG can consist of one or more PEG side-chains which are linked together. PEGs with more than one PEG chain are called multiarmed or branched PEGs. Branched PEGs can be prepared, for example, by the addition of polyethylene oxide to various polyols, including glycerol, pentaerythriol, and sorbitol. For example, a four-armed branched PEG can be prepared from pentaerythriol and ethylene oxide. Branched PEG are described in, for example, EP-A 0 473 084 and U.S. Pat. No. 5,932,462. One form of PEGs includes two PEG side-chains (PEG2) linked via the primary amino groups of a lysine (Monfardini, C., et al., Bioconjugate Chem. 6 (1995) 62-69).

PEG conjugation to peptides or proteins generally involves the activation of PEG and coupling of the activated PEG-intermediates directly to target proteins/peptides or to a linker, which is subsequently activated and coupled to target proteins/peptides (see Abuchowski, A. et al, J. Biol. Chem., 252, 3571 (1977) and J. Biol. Chem., 252, 3582 (1977), Zalipsky, et al., and Harris et. al., in: Poly(ethylene glycol) Chemistry: Biotechnical and Biomedical Applications; (J. M. Harris ed.) Plenum Press: New York, 1992; Chap. 21 and 22).

One skilled in the art can select a suitable molecular mass for PEG, e.g., based on how the pegylated tim-3 or galectin-9 polypeptide will be used therapeutically, the desired dosage, circulation time, resistance to proteolysis, immunogenicity, and other considerations. For a discussion of PEG and its use to enhance the properties of proteins, see N. V. Katre, Advanced Drug Delivery Reviews 10: 91-114 (1993).

In one embodiment of the invention, PEG molecules may be activated to react with amino groups on tim-3 or galectin-9 polypeptides, such as with lysines (Bencham C. O. et al., Anal. Biochem., 131, 25 (1983); Veronese, F. M. et al., Appl. Biochem., 11, 141 (1985).; Zalipsky, S. et al., Polymeric Drugs and Drug Delivery Systems, adrs 9-110 ACS Symposium Series 469 (1999); Zalipsky, S. et al., Europ. Polym. J., 19, 1177-1183 (1983); Delgado, C. et al., Biotechnology and Applied Biochemistry, 12, 119-128 (1990)). In another embodiment, PEG molecules may be coupled to sulfhydryl groups on tim-3 or galectin-9 (Sartore, L., et al., Appl. Biochem. Biotechnol., 27, 45 (1991); Morpurgo et al., Biocon. Chem., 7, 363-368 (1996); Goodson et al., Bio/Technology (1990) 8, 343; U.S. Pat. No. 5,766,897). U.S. Pat. Nos. 6,610, 281 and 5,766,897 describes exemplary reactive PEG species that may be coupled to sulfhydryl groups. In some embodiments, the pegylated tim-3 or galectin-9 proteins comprise a PEG molecule covalently attached to the alpha amino group of the N-terminal amino acid. Site specific N-terminal reductive amination is described in Pepinsky et al., (2001) JPET, 297,1059, and U.S. Pat. No. 5,824,784. The use of a PEG-aldehyde for the reductive amination of a protein utilizing other available nucleophilic amino groups is described in U.S. Pat. No. 4,002,531, in Wieder et al., (1979) J. Biol. Chem. 254,12579, and in Chamow et al., (1994) Bioconjugate Chem. 5, 133.

(6) Immunological Reagents

The invention additionally provides immunological reagents capable of binding to tim-3 polypeptides, including mouse and human polypeptides, and in preferred embodiments, immunological reagents that bind to soluble tim-3 but not to full-length tim-3.

One aspect of the invention provides an isolated antibody or fragment thereof which binds to a polypeptide having an amino acid sequence set forth in SEQ ID NO: 2 but which does not bind to a polypeptide having the amino acid sequence set forth in SEQ ID NO: 13. SEQ ID NO: 2 is the human soluble tim-3 protein while SEQ ID NO: 13 is the human full-length tim-3 protein. Accordingly, such antibodies would bind to soluble human tim-3 but not to full-length human tim-3.

Another aspect of the invention provides an isolated antibody or fragment thereof which binds to a polypeptide having an amino acid sequence set forth in SEQ ID NO: 4 but which does not bind to a polypeptide having the amino acid sequence set forth in SEQ ID NO: 14. SEQ ID NO: 4 is the mouse soluble tim-3 protein while SEQ ID NO: 14 is the mouse full-length tim-3 protein. Accordingly, such antibodies would bind to soluble mouse tim-3 but not to full-length mouse tim-3.

Generating specific antisera that binds to soluble tim-3 but not to full-length tim-3 can be achieved, for example, by generating immunogens to a peptide having an amino acid sequence contained in the soluble tim-3 protein which is absent from the full-length protein. Such a peptide may span the junction of the IgV domain and intracellular domains of soluble tim-3. This junction is not present in the full-length tim-3 sequence, where the mucin and transmembrane domains are inserted between the IgV and intracellular domains. In one embodiment, the 16 amino acid human soluble tim-3 peptide according to SEQ ID NO: 6 is used as an immunogen to generate such antibodies. To generate the equivalent antibodies to mouse tim-3, the peptide according to SEQ ID NO: 8 can be used. One skilled in the art can manipulate this peptide by extending at either the C- or N-terminus or both with additional residues, or by shortening as desired to increase immunogenicity or solubility. In addition, cysteine groups or other residues can be added to the peptide to conjugate to a carrier or confer additional desirable properties.

Similarly, peptides that bind to full-length tim-3, but not to soluble tim-3, can be generated using peptides whose sequences are found in the full-length but not in the soluble form of tim-3. For instance, such peptides can correspond to the sequences of the tim-3 transmembrane domain, or more preferably, to sequences of the tim-3 mucin domain. Alternatively, these peptides may contain sequences that span the junction between the IgV domain and the mucin domain of full-length tim-3, or between the transmembrane domain and the intracellular domains also of full-length tim-3.

Chickens, mammals, such as a mouse, a hamster, a goat, a guinea pig or a rabbit, can be immunized with an immunogenic form of the any of the peptides variants described (e.g., an antigenic fragment which is capable of eliciting an antibody response). Techniques for conferring immunogenicity on a protein or peptide include conjugation to carriers or other techniques well known in the art. For instance, a peptidyl portion of one of the subject proteins can be administered in the presence of adjuvant. The progress of immunization can be monitored by detection of antibody titers in plasma or serum. Standard ELISA or other immunoassays can be used with the immunogen as antigen to assess the levels of antibodies.

Following immunization, antisera can be obtained and, if desired, polyclonal antibodies against the target protein can be further isolated from the serum. To produce monoclonal antibodies, antibody producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, Nature, 256: 495-497, 1975), as well as the human B cell hybridoma technique (Kozbar et al., Immunology Today, 4: 72, 1983), and the EBV-hybridoma technique to produce human monoclonal antibodies (Cole et al., Monoclonal Antibodies and Cancer Therapy, Alan R. Liss, Inc. pp. 77-96, 1985). Hybridoma cells can be screened immunochemically for production of antibodies specifically reactive to the tim-3 peptide and the monoclonal antibodies isolated. Accordingly, another aspect of the invention provides hybridoma cell lines which produce the antibodies described herein.

The antibodies can then be tested for their binding specificity to full-length tim-3 and soluble tim-3. For example, antibodies generated against the peptide according to SEQ ID NO: 6, which corresponds to the IgV-Intracellular domain junction of human soluble tim-3, can be tested for their ability to bind to either form of tim-3 by immobilizing the tim-3 polypeptide on a membrane and performing a western blot with the antibodies. One skilled in the art may employ any routine method to determine if antibodies bind to a protein.

In other embodiments, monoclonal antibodies can be generated against the entire tim-3 soluble protein, and then screened for whether or not they bind to the full-length tim-3 protein, in order to identify antibodies specific to only soluble tim-3.

The term antibody as used herein is intended to include fragments which are also specifically reactive with a protein described herein or a complex comprising such protein. Antibodies can be fragmented using conventional techniques and the fragments screened in the same manner as described above for whole antibodies. For example, $F(ab')_2$ fragments can be generated by treating antibody with pepsin. The resulting $F(ab')_2$ fragment can be treated to reduce disulfide bridges to produce Fab' fragments. The antibody of the present invention is further intended to include bispecific and chimeric molecules, as well as single chain (scFv) antibodies.

The subject antibodies include trimeric antibodies and humanized antibodies, which can be prepared as described, e.g., in U.S. Pat. No. 5,585,089. Also within the scope of the invention are single chain antibodies. All of these modified forms of antibodies as well as fragments of antibodies are intended to be included in the term "antibody".

(7) Identification of Tim-3/Galectin-9 Immunomodulatory Agents

Another aspect of the invention provides methods for identifying agents which modulate immunomodulatory responses, such as, for example, identifying agents which modulate the interaction between tim-3 and galectin-9. In one aspect, the invention provides methods for identifying agents which block the binding of tim-3 to tim-3 ligands, such as to galectin-9. Agents which block this interaction would be predicted to prevent activation of tim-3, leading to increased Th1 responses and/or reduced Th2 responses. In another aspect, the invention provides methods for identifying agents which promote the binding of tim-3 to tim-3 ligands, such as to galectin-9, or which mimic the ligand binding to tim-3. Such would be predicted to promote activation of tim-3, leading to decreased Th1 responses and/or increased Th2 responses. Accordingly, agents identified using the methods described herein may be used to modulate $T_H1$ and $T_H2$ responses in a subject in need thereof.

In one aspect, the identification of a tim-3/galectin-9 complex in the present invention facilitates rational design of agonists and antagonists based on the structural features of the tim-3 and galectin-9 proteins, which can be determined using X-ray crystallography, neuron diffraction, nuclear magnetic resonance spectrometry, and other techniques. Methods for rational drug design are well known in the art (see Chemical and Structural Approaches to Rational Drug Design, David B Weiner, William V. Williams, CRC Press (1994); Rational Drug Design: Novel Methodology and Practical Applications, Vol. 719, Abby L. Parrill (Editor), American Chemical Society (1999); Structure-based Ligand Design, Klaus Gubernator, Wiley, John & Sons, Incorporated (1998)). A related aspect of the invention provides reconstituted protein preparations comprising a tim-3 polypeptide and/or a galectin-9 polypeptide. In a specific embodiment, at least 1% of the protein in the reconstituted compositions is a tim-3 polypeptide and a galectin-9 polypeptide, or more preferably at least 2%, 3%, 4%, 5%, 10%, 20%, 30%, 40% or 50%. In a one embodiment, the proteins in the reconstituted compositions are recombinant proteins.

Another aspect of the invention provides methods for screening agents that promote or block the formation of a complex between tim-3 and galectin-9. Such methods may be performed in vitro or in a cell, and they may be performed using full-length proteins or fragments thereof, such as soluble fragments (i.e. those lacking a transmembrane domain), of one or both of the proteins. In some embodiments of the methods described herein, soluble protein comprising the IgV, and optionally the mucin domain, of tim-3 are used. A variety of other reagents may be included in the screening assay. These include reagents like salts, neutral proteins, e.g. albumin, detergents, etc. that are used to facilitate optimal protein-protein binding and/or reduce non-specific or background interactions. Reagents that improve the efficiency of the assay, such as protease inhibitors, nuclease inhibitors, anti-microbial agents, etc. may also be used. The mixture of components are added in any order that provides for the requisite binding. Incubations are performed at any suitable temperature, typically between 4° C. and 40° C. Incubation periods are selected for optimum activity, but may also be optimized to facilitate rapid high-throughput screening. Typically between 0.1 and 1 hours will be sufficient for in vitro assays.

The methods for the identification of agents of the present invention are well suited for screening libraries of compounds in multi-well plates (e.g., 96-well plates), with a different test compound or group of test compounds in each well. In particular, the methods may be employed with combinatorial libraries. These methods may be "miniaturized" in an assay system through any acceptable method of miniaturization, including but not limited to multi-well plates, such as 24, 48, 96 or 384-wells per plate, micro-chips or slides. The assay may be reduced in size to be conducted on a micro-chip support, advantageously involving smaller amounts of reagents and other materials. Any miniaturization of the process which is conducive to high-throughput screening is within the scope of the invention.

One specific aspect of the invention provides methods for identifying therapeutic agents that modulate Th1 function. Accordingly, one aspect of the invention provides a method for assessing the ability of an agent to modulate Th1 activation, comprising: 1) combining: a tim-3 polypeptide or fragment thereof, a galectin-9 polypeptide or fragment thereof, and an agent, under conditions wherein the tim-3 and galectin-9 polypeptides physically interact in the absence of the agent, 2) determining if the agent interferes with the interaction, and optionally, 3) for an agent that interferes with the interaction, further assessing its ability to promote the activation of Th1 cells.

Another specific aspect of the invention provides a method of identifying an agent that modulates the binding between a tim-3 polypeptide and a galectin-9 polypeptide comprising: (a) contacting the tim-3 polypeptide and the galectin-9 polypeptide in the presence of a test agent; and (b) determining the effect of the test agent on the binding of the tim-3 polypeptide and the galectin-9 polypeptide; thereby identifying a agent that modulates the binding between a tim-3 polypeptide and a galectin-9 polypeptide.

A related specific aspect of the invention provides a method of identifying an agent that modulates an immune response, the method comprising (a) contacting the tim-3 polypeptide and the galectin-9 polypeptide in the presence of a test agent; and (b) determining the effect of the test agent on the binding of the tim-3 polypeptide and the galectin-9 polypeptide; thereby identifying an agent that modulates an immune response.

In one embodiment of the methods described herein for detecting the interaction between a tim-3 polypeptide and a galectin-9 polypeptide, the galectin-9 polypeptide comprises (i) amino acids 1-323 of SEQ ID NO: 10; r(ii) amino acids 1-355 of SEQ ID NO: 19; or (iii) an amino acid sequence that is at least 90% identical to amino acids 1-323 of SEQ ID NO: 10; (iii) an amino acid sequence that is at least 90% identical to amino acids 1-355 of SEQ ID NO: 19. In another embodiment, the tim-3 polypeptide comprises (i) amino acids 30-128 of SEQ ID NO: 13; or (iii) an amino acid sequence that is at least 90% identical to amino acids 30-128 of SEQ ID NO: 13.

In some aspect of the invention the agents are identified through in vitro assays. A variety of assay formats will suffice and, in light of the present disclosure, those not expressly described herein will nevertheless be comprehended by one of ordinary skill in the art. Assay formats which approximate such conditions as formation of protein complexes, enzymatic activity, may be generated in many different forms, and include assays based on cell-free systems, e.g. purified proteins or cell lysates, as well as cell-based assays which utilize intact cells. Simple binding assays can also be used to detect agents which bind to tim-3 or galectin-9. Such binding assays may also identify agents that act by disrupting the interaction between a tim-3 polypeptide and a galectin-9 polypeptide.

Agents to be tested can be produced, for example, by bacteria, yeast or other organisms (e.g. natural products), produced chemically (e.g. small molecules, including peptidomimetics), or produced recombinantly. Because tim-3 and galectin-9 are transmembrane proteins, preferred embodiments of the assays and methods described to identify agents which modulate complex formation between tim-3 and galectin-9 employ soluble forms of these proteins rather than full-length protein. Soluble forms include those lacking the transmembrane domain and/or those comprising the IgV domain or fragments thereof which retain their ability to bind their cognate binding partners.

In many drug screening programs which test libraries of compounds and natural extracts, high throughput assays are desirable in order to maximize the number of compounds surveyed in a given period of time. Assays of the present invention which are performed in cell-free systems, which may be developed with purified or semi-purified proteins or with lysates, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with other proteins or changes in enzymatic properties of the molecular target.

In preferred in vitro embodiments of the present assay, a reconstituted tim-3/galectin-9 complex comprises a reconstituted mixture of at least semi-purified proteins. By semi-purified, it is meant that the proteins utilized in the reconstituted mixture have been previously separated from other cellular or viral proteins. For instance, in contrast to cell lysates, the proteins involved in tim-3/galectin-9 complex formation are present in the mixture to at least 50% purity relative to all other proteins in the mixture, and more preferably are present at 90-95% purity. In certain embodiments of the subject method, the reconstituted protein mixture is derived by mixing highly purified proteins such that the reconstituted mixture substantially lacks other proteins (such as of cellular or viral origin) which might interfere with or otherwise alter the ability to measure tim-3/galectin-9 complex assembly and/or disassembly.

Assaying tim-3/galectin-9 complexes, in the presence and absence of a candidate agent, can be accomplished in any vessel suitable for containing the reactants. Examples include microtitre plates, test tubes, and micro-centrifuge tubes. In a screening assay, the effect of a test agent may be assessed by, for example, assessing the effect of the test agent on kinetics, steady-state and/or endpoint of the reaction.

In one embodiment of the present invention, drug screening assays can be generated which detect inhibitory agents on the basis of their ability to interfere with assembly or stability of the tim-3/galectin-9 complex. In an exemplary binding assay, the compound of interest is contacted with a mixture comprising a tim-3/galectin-9 complex. Detection and quantification of tim-3/galectin-9 complexes provides a means for determining the compound's efficacy at inhibiting (or potentiating) interaction between the two polypeptides. The efficacy of the compound can be assessed by generating dose response curves from data obtained using various concentrations of the test compound. Moreover, a control assay can also be performed to provide a baseline for comparison. In the control assay, the formation of complexes is quantitated in the absence of the test compound.

Complex formation may be detected by a variety of techniques. For instance, modulation in the formation of complexes can be quantitated using, for example, detectably labeled proteins (e.g. radiolabeled, fluorescently labeled, or enzymatically labeled), by immunoassay, or by chromatographic detection. Surface plasmon resonance systems, such as those available from Biacore© International AB (Uppsala, Sweden), may also be used to detect protein-protein interaction.

The proteins and peptides described herein may be immobilized. Often, it will be desirable to immobilize the peptides and polypeptides to facilitate separation of complexes from uncomplexed forms of one of the proteins, as well as to accommodate automation of the assay. The peptides and polypeptides can be immobilized on any solid matrix, such as a plate, a bead or a filter. The peptide or polypeptide can be immobilized on a matrix which contains reactive groups that bind to the polypeptide. Alternatively or in combination, reactive groups such as cysteines in the protein can react and bind to the matrix. In another embodiment, the polypeptide may be expressed as a fusion protein with another polypeptide which has a high binding affinity to the matrix, such as a fusion protein to streptavidin which binds biotin with high affinity.

In an illustrative embodiment, a fusion protein can be provided which adds a domain that permits the protein to be bound to an insoluble matrix. For example, a GST-TIM-3-IgV-domain fusion protein, which comprises the IgV domain of tim-3 fused to glutathione transferase, can be adsorbed onto glutathione sepharose beads (Sigma Chemical, St. Louis, Mo.) or glutathione derivatized microtitre plates, which are then combined with galectin-9 or a fragment thereof, e.g. an $^{35}$S-labeled polypeptide, and the test compound and incubated under conditions conducive to complex formation. Following incubation, the beads are washed to remove any unbound interacting protein, and the matrix bead-bound radiolabel determined directly (e.g. beads placed in scintillant), or in the supernatant after the complexes are dissociated, e.g. when microtitre plate is used. Alternatively, after washing away unbound protein, the complexes can be dissociated from the matrix, separated by SDS-PAGE gel, and the level of interacting polypeptide found in the matrix-bound fraction quantitated from the gel using standard electrophoretic techniques.

It will be understood that various modifications of the above-described assay are included within the scope of the present invention. For example, the roles of the proteins can be switched—that is, the galectin-9 protein may be immobilized to the solid support and a solution containing the tim-3 protein may be contacted with the bound galectin-9 protein. Additionally, the immobilized protein or the free protein may be exposed to a test compound prior to the binding assay, and the effects of this pre-exposure may be assessed relative to controls. Compounds identified in this manner also inhibit the binding of the tim-3 to galectin-9 or vice versa. Alternatively, the test compound may be added subsequent to the mixing of tim-3 and galectin-9. A compound effective to reduce the level of binding in such an assay displaces tim-3 protein from the galectin-9 protein or vice versa.

In addition to Western blots, other, more rapid, detection schemes, such as multi-well ELISA-type approaches, may be employed. For example, a partially-purified (e.g., by the GST methods above) tim-3 protein may be attached to the bottoms of wells in a multi-well plate (e.g., 96-well plate) by introducing a solution containing the protein into the plate and allowing the protein to bind to the plastic. The excess protein-containing solution is then washed out, and a blocking solution (containing, for example, bovine serum albumin (BSA)) is introduced to block non-specific binding sites. The plate is then washed several more times and a solution containing an galectin-9 protein and, in the case of experimental (vs. control) wells, a test compound added. Different wells may contain different test compound, different concentrations of the same test substance, different tim-3 proteins or galectin-9 protein, or different concentrations of tim-3 protein or galectin-9 protein. Further, it will be understood that various modifications to this detection scheme may be made. For example, the wells of a multi-well plate may be coated with a polypeptide containing the galectin-9 protein, rather than the tim-3 protein, and binding interactions assayed upon addition of a free tim-3 protein. The wells may also be pre-coated with compound(s) that enhance attachment of the protein to be immobilized and/or decrease the level of non-specific binding. For example, the wells may be derivatized to contain glutathione and may be pre-coated with BSA, to promote attachment of the immobilized protein in a known orientation with the binding site(s) exposed.

Detection methods useful in such assays include antibody-based methods (i.e., an antibody directed against the "free" protein), direct detection of a reporter moiety incorporated into the "free" protein (such as a fluorescent label), and proximity energy transfer methods (such as a radioactive "free" protein resulting in fluorescence or scintillation of molecules incorporated into the immobilized protein or the solid support).

Yet another variation of the methods of the present invention for identifying a compound capable of affecting binding of a tim-3 protein to a galectin-9 protein is through the use of affinity biosensor methods. Such methods may be based on the piezoelectric effect, electrochemistry, or optical methods, such as ellipsometry, optical wave guidance, and surface plasmon resonance (SPR). SPR is particular advantageous for monitoring molecular interactions in real-time, enabling a sensitive and comprehensive analysis of the effects of test compounds on the binding interactions between two proteins than the methods discussed above. This advantage is somewhat offset, however, by the lower throughput of the technique (as compared with multi-well plate-based methods).

As hereinbefore mentioned, a test compound can be said to have an effect on the binding between a tim-3 protein and a galectin-9 protein if the compound has any effect on the binding of tim-3 to the galectin-9 protein (i.e., if the compound increases or decreases the binding), and the effect exceeds a threshold value (which is set to a desired level by the practitioner of the invention as described above; e.g., several-fold increase or several-fold decrease in binding). Preferably the effect on binding is a significant effect. The term "significant" as used herein, specifically in terms of a "significant effect", refers to a difference in a quantifiable parameter between two groups being compared that is statistically-significant using standard statistical tests. In some embodiments of the methods described herein, step (b) comprises comparing formation of a tim-3/galectin-9 complex in the presence of the test agent with an appropriate control. In some embodiments, the appropriate control comprises the formation of a complex between the first polypeptide and the second polypeptide in the absence of the agent or compound being tested.

Therefore, in an embodiment of the present invention, there is provided a method of screening for compounds that affect the binding between a tim-3 protein and a galectin-9 protein comprising: (a) contacting the tim-3 protein and the galectin-9 protein in the presence of a test compound; (b) determining the effect of the test compound on the binding of the tim-3 protein and the galectin-9 protein; and (c) identifying the compound as effective if its measured effect on the extent of binding is above a threshold level.

The term "affect the binding between a tim-3 protein and a galectin-9 protein" means the test compound produces a difference in the binding between the tim-3 protein and the galectin-9 protein in its presence as compared to the binding between the tim-3 protein and the galectin-9 protein in its absence (control). Preferably this difference in binding is a significant difference. In a specific embodiment, a significant difference comprises at least a 10%, 20%, 30%, 40%, 50%, 75%, 100%, 150%, 200% or 500% increase or decrease in binding. The compound may inhibit or enhance the binding, or in terms of the affect on tim-3, act as an antagonist, an agonist or act as a compound which enhances the effects of other agonists or antagonists. The type of measurement used to quantify the effect of a test compound on the binding between a tim-3 protein and a galectin-9 protein will depend on the type of assay and detection methods used and this can be readily determined by a person having skill in the art. For example, when using a biological screen that employs Western blotting as the means for detection, the binding can be measured using densitometry. The densitometry values may be normalized and a threshold level may be set based on the amount of variation in the signal between a series of control samples (i.e. without test compound). The smaller the variation, the smaller the effect of a test compound that can be reliably detected.

In still further embodiments of the present assays, the tim-3/galectin-9 complex is generated in whole cells, taking advantage of cell culture techniques to support the subject assay. For example, as described below, the tim-3/galectin-9 complex can be constituted in a eukaryotic cell culture system, such as a mammalian cell or a yeast cell. Other cells know to one skilled in the art may be used. Advantages to generating the subject assay in a whole cell include the ability to detect inhibitors which are functional in an environment more closely approximating that which therapeutic use of the inhibitor would require, including the ability of the agent to gain entry into the cell. Furthermore, certain of the in vivo embodiments of the assay, such as examples given below, are amenable to high through-put analysis of test agents. The components of the tim-3/galectin-9 complex can be endogenous to the cell selected to support the assay. Alternatively, some or all of the components can be derived from exogenous sources. For instance, fusion proteins can be introduced into the cell by recombinant techniques (such as through the use of an expression vector), as well as by microinjecting the fusion protein itself or mRNA encoding the fusion protein.

In yet another embodiment, the tim-3 and galectin-9 polypeptides can be used to generate an interaction trap assay (see also, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696), for subsequently detecting agents which disrupt binding of the proteins to one and other.

The yeast two-hybrid protein interaction assay may also be employed to identify compounds that affect the binding of a tim-3 protein to a galectin-9 protein. The assay is based on the finding that most eukaryotic transcription activators are modular, i.e., that the activators typically contain activation domains that activate transcription, and DNA binding domains that localize the activator to the appropriate region of a DNA molecule.

In a two hybrid system, a first fusion protein contains one of a pair of interacting proteins fused to a DNA binding domain, and a second fusion protein contains the other of a pair of interacting proteins fused to a transcription activation domain. The two fusion proteins are independently expressed in the same cell, and interaction between the "interacting protein" portions of the fusions reconstitute the function of the transcription activation factor, which is detected by activation of transcription of a reporter gene. At least two different cell-based two hybrid protein-protein interaction assay systems have been used to assess binding interactions and/or to identify interacting proteins. Both employ a pair of fusion hybrid proteins, where one of the pair contains a first of two "interacting" proteins fused to a transcription activation domain of a transcription activating factor, and the other of the pair contains a second of two "interacting" proteins fused to a DNA binding domain of a transcription activating factor.

In another embodiment, one of the proteins is expressed on a cell, such as on the cell surface, whereas the other protein is a native or a recombinant protein that is purified or partially purified and contacted with the cell, such as to allow formation of a complex.

In some embodiments, the agents identified as modulating the binding interaction between tim-3 and galectin-9 may be further evaluated for functional effects, such as their effect on the induction of a Th1/Th2 response by T cells in vitro or in vivo, such as by using the assays described in the experimental section. In some embodiments, animal models of disease conditions are further used to characterize the agents identified using the methods described herein, such as Experimental Autoimmune Encephalomyelitis models, KKAy mice as model of type 2 diabetes mellitus and Fabry disease models (alphaGAL knock-out). See also Bedell et al., Genes Dev. 1997 Jan. 1; 11(1):11-43 for additional mouse models of human disease which may be used.

The test agent or test compound can be any agent or compound which one wishes to test including, but not limited to, proteins (including antibodies), peptides, nucleic acids (including RNA, DNA, antisense oligonucleotide, peptide nucleic acids), carbohydrates, organic compounds, inorganic compounds, natural products, library extracts, bodily fluids and other samples that one wishes to test for affecting the binding between a tim-3 and galectin-9 polypeptide. In particular the test compound may be a peptide mimetic of a tim-3 protein or a fragment thereof. In some embodiments the test agent is purified or partially purified agent, whereas in other embodiments it is not purified.

Test agents encompass numerous chemical classes, though typically they are organic molecules, preferably small organic compounds having a molecular weight of more than 50 and less than about 2,500 Daltons. test agents comprise functional groups necessary for structural interaction with proteins, particularly hydrogen bonding, and typically include at least an amine, carbonyl, hydroxyl or carboxyl group, preferably at least two of the functional chemical groups. The test agents often comprise cyclical carbon or heterocyclic structures and/or aromatic or polyaromatic structures substituted with one or more of the above functional groups. test agents are also found among biomolecules including, but not limited to: peptides, saccharides, fatty acids, steroids, purines, pyrimidines, derivatives, structural analogs or combinations thereof.

Test agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Libraries of small organic/peptide may be generated using combinatorial techniques such as those described in Blondelle et al. (1995) Trends Anal. Chem. 14:83; the Affymax U.S. Pat. Nos. 5,359,115 and 5,362,899; the Ellman U.S. Pat. No. 5,288,514; the Still et al. PCT publication WO 94/08051; Chen et al. (1994) JACS 116:2661; Kerr et al. (1993) JACS 115:252; PCT publications WO92/10092, WO93/09668 and WO91/07087; and the Lerner et al. PCT publication WO93/20242.

Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In other embodiments, the test agents are peptidomimetics of tim-3, galectin-9 or fragments thereof. Peptidomimetics are compounds based on, or derived from, peptides and proteins. Peptidomimetics that may be used in the present invention typically can be obtained by structural modification of a known analog peptide sequence using unnatural amino acids, conformational restraints, isosteric replacement, and the like. The subject peptidomimetics constitute the continuum of structural space between peptides and non-peptide synthetic structures; analog peptidomimetics may be useful, therefore, in delineating pharmacophores and in helping to translate peptides into nonpeptide compounds with the activity of the parent analog peptides.

Moreover, as is apparent from the present disclosure, mimetopes of the subject tim-3 and galectin-9 sequences can be provided. Such peptidomimetics can have such attributes as being non-hydrolyzable (e.g., increased stability against proteases or other physiological conditions which degrade the corresponding peptide), increased specificity and/or potency, and increased cell permeability for intracellular localization of the peptidomimetic. For illustrative purposes, peptide analogs of the present invention can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in *Peptides: Chemistry and Biology*, G. R. Marshall ed., ESCOM Publisher: Leiden, Netherlands, 1988, p 123), C-7 mimics (Huffman et al. in *Peptides: Chemistry and Biology*, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in *Peptides: Structure and Function* (Proceedings of the 9th American Peptide Symposium) Pierce Chemical Co. Rockland, Ill., 1985), α-turn dipeptide cores (Nagai et al. (1985) *Tetrahedron Lett* 26:647; and Sato et al. (1986) *J Chem Soc Perkin Trans* 1:1231), α-aminoalcohols (Gordon et al. (1985) *Biochem Biophys Res Commun* 126:419; and Dann et al. (1986) *Biochem Biophys Res Commun* 134:71), diaminoketones (Natarajan et al. (1984) *Biochem Biophys Res Commun* 124:141), and methyleneamino-modifed (Roark et al. in *Peptides: Chemistry and Biology*, G. R. Marshall ed., ESCOM Publisher: Leiden, Netherlands, 1988, p 134). Also, see generally, Session III: Analytic and synthetic methods, in *Peptides: Chemistry and Biology*, G. R. Marshall ed., ESCOM Publisher: Leiden, Netherlands, 1988).

In addition to a variety of sidechain replacements that can be carried out to generate the subject analog peptidomimetics, the present invention specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides.

In some embodiments, the test agents are preselected for their ability to bind to a tim-3 or a galectin-9 protein prior to determining if they can affect the binding between a tim-3 or a galectin-9 polypeptide. In one embodiment, test agent may first be selected for its ability to bind a tim-3 or a galectin-9 polypeptide. The test agent may be preselected by screening a library of test agents, such as a peptide library or a phage display library.

(8) Compositions, Formulations and Packaging

A further aspect of the invention provides compositions comprising the nucleic acids, polypeptides or agents described herein. In one embodiment, the compositions are pharmaceutical compositions. Pharmaceutical compositions for use in accordance with the present invention may be formulated in conventional manner using one or more physiologically acceptable carriers or excipients. Thus, the compounds and their physiologically acceptable salts and solvates may be formulated for administration by, for example, by aerosol, intravenous, oral or topical route. The administration may comprise intralesional, intraperitoneal, subcutaneous, intramuscular or intravenous injection; infusion; liposome-mediated delivery; topical, intrathecal, gingival pocket, per rectum, intrabronchial, nasal, transmucosal, intestinal, oral, ocular or otic delivery.

An exemplary composition of the invention comprises an RNAi mixed with a delivery system, such as a liposome system, and optionally including an acceptable excipient. In a preferred embodiment, the composition is formulated for injection.

Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. in addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

For therapies involving the administration of nucleic acids, the oligomers of the invention can be formulated for a variety of modes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, intranodal, and subcutaneous for injection, the oligomers of the invention can be formulated in liquid solutions, preferably in physiologically compatible buffers such as Hank's solution or Ringer's solution. In addition, the oligomers may be formulated in solid form and redissolved or suspended immediately prior to use. Lyophilized forms are also included.

Systemic administration can also be by transmucosal or transdermal means, or the compounds can be administered orally. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For oral administration, the oligomers are formulated into conventional oral administration forms such as capsules, tablets, and tonics. For topical administration, the oligomers of the invention are formulated into ointments, salves, gels, or creams as generally known in the art.

Toxicity and therapeutic efficacy of the agents and compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic induces are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

In one embodiment of the methods described herein, the effective amount of the agent is between about 1 mg and about 50 mg per kg body weight of the subject. In one embodiment, the effective amount of the agent is between about 2 mg and about 40 mg per kg body weight of the subject. In one embodiment, the effective amount of the agent is between about 3 mg and about 30 mg per kg body weight of the subject. In one embodiment, the effective amount of the agent is between about 4 mg and about 20 mg per kg body weight of the subject. In one embodiment, the effective amount of the agent is between about 5 mg and about 10 mg per kg body weight of the subject.

In one embodiment of the methods described herein, the agent is administered at least once per day. In one embodiment, the agent is administered daily. In one embodiment, the agent is administered every other day. In one embodiment, the agent is administered every 6 to 8 days. In one embodiment, the agent is administered weekly.

As for the amount of the compound and/or agent for administration to the subject, one skilled in the art would know how to determine the appropriate amount. As used herein, a dose or amount would be one in sufficient quantities to either inhibit the disorder, treat the disorder, treat the subject or prevent the subject from becoming afflicted with the disorder. This amount may be considered an effective amount. A person of ordinary skill in the art can perform simple titration experiments to determine what amount is required to treat the subject. The dose of the composition of the invention will vary depending on the subject and upon the particular route of administration used. In one embodiment, the dosage can range from about 0.1 to about 100,000 ug/kg body weight of the subject. Based upon the composition, the dose can be delivered continuously, such as by continuous pump, or at periodic intervals. For example, on one or more separate occasions. Desired time intervals of multiple doses of a particular composition can be determined without undue experimentation by one skilled in the art.

The effective amount may be based upon, among other things, the size of the compound, the biodegradability of the compound, the bioactivity of the compound and the bioavailability of the compound. If the compound does not degrade quickly, is bioavailable and highly active, a smaller amount will be required to be effective. The effective amount will be known to one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount. In one embodiment of the above methods, the effective amount of the compound comprises from about 1.0 ng/kg to about 100 mg/kg body weight of the subject. In another embodiment of the above methods, the effective amount of the compound comprises from about 100 ng/kg to about 50 mg/kg body weight of the subject. In another embodiment of the above methods, the effective amount of the compound comprises from about 1 ug/kg to about 10 mg/kg body weight of the subject. In another embodiment of the above methods, the effective amount of the compound comprises from about 100 ug/kg to about 1 mg/kg body weight of the subject.

As for when the compound, compositions and/or agent is to be administered, one skilled in the art can determine when to administer such compound and/or agent. The administration may be constant for a certain period of time or periodic and at specific intervals. The compound may be delivered hourly, daily, weekly, monthly, yearly (e.g. in a time release form) or as a one time delivery. The delivery may be continuous delivery for a period of time, e.g. intravenous delivery. In one embodiment of the methods described herein, the agent is administered at least once per day. In one embodiment of the methods described herein, the agent is administered daily. In one embodiment of the methods described herein, the agent is administered every other day. In one embodiment of the methods described herein, the agent is administered every 6 to 8 days. In one embodiment of the methods described herein, the agent is administered weekly.

Another aspect of the invention provides a pharmaceutical package comprising (i) a polypeptide which comprises the IgV domain of tim-3; and (ii) instructions for administering the composition to a subject afflicted with a hyperplastic condition selected from the group comprising of renal cell cancer, Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, testicular cancer, gastrointestinal cancer and stomach cancer.

(9) Methods of Regulating Immune Responses

One aspect of the invention provides methods of modulating immune responses, such as but not limited to, modulating Th1 or Th2 responses, immune tolerance and transplantation tolerance. The term modulating as used herein refers to increasing or decreasing. The methods of regulating immune responses of the present application are based, in part, on the discovery that titrating tim-3 ligands, using a fusion protein comprising soluble tim-3, Th1 responses are enhanced, the establishment of peripheral tolerance is abrogated, and transplantation tolerance is decreased. By contrast, the administration of galectin-9 to mammals, discovered by applicants as a tim-3 ligand, results in reduced Th1 responses.

Another aspect of the invention provides a method of reducing immune tolerance, increasing Th1-mediated immune responses, and/or decreasing Th2-mediated immune responses in a subject in need thereof, the method comprising administering to the subject a therapeutically effective amount of an agent that decreases the expression or activity of tim-3, galectin-9 or both i.e. a tim-3 or galectin-9 antagonist, or that decreases the binding of tim-3 to galectin-9.

Reducing immune tolerance and increasing Th1-mediated responses, by decreasing tim-3 activity, is beneficial in cancer immunotherapy. The immune system can develop tolerance against tumor antigens, thus allowing tumors to evade immune surveillance. In one aspect of the invention, an agent which decreases tim-3 activity is administered to a subject afflicted with a hyperplastic condition.

The terms "cancer" and "tumor" are used interchangeably, both terms referring to a hyperplastic condition. In one embodiments, the cancer is selected from the group consisting of Kaposi's sarcoma, chronic leukemia, prostate cancer, breast cancer, sarcoma, pancreatic cancer, leukemia, ovarian carcinoma, rectal cancer, throat cancer, melanoma, colon cancer, bladder cancer, lymphoma, mastocytoma, lung cancer, mammary adenocarcinoma, pharyngeal squamous cell carcinoma, and gastrointestinal or stomach cancer. In another embodiment, the cancer is selected for the group consisting of basal cell carcinoma, biliary tract cancer; bladder cancer; bone cancer; brain and CNS cancer; breast cancer; cervical cancer; choriocarcinoma; colon and rectum cancer; connective tissue cancer; cancer of the digestive system; endometrial cancer; esophageal cancer; eye cancer; cancer of the head and neck; gastric cancer; intra-epithelial neoplasm; kidney cancer; larynx cancer; leukemia; liver cancer; lung cancer (e.g., small cell and non-small cell); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; sarcoma; skin cancer; stomach cancer; testicular cancer; thyroid cancer; uterine cancer; cancer of the urinary system, as well as other carcinomas and sarcomas.

In another embodiment, the agents used to increase Th1 activation by inhibiting tim-3 activity are used to enhance the immune response of a subject to a vaccine. In one particular, embodiment, and agent which inhibits tim-3 activity, such as a polypeptide comprising a tim-3 IgV domain or an antibody that inhibits the formation of a complex between full-length tim-3 and a tim-3 ligand, is administered with the vaccine to enhance the immune response towards the vaccine. Vaccines include, but are not limited to, those intended to prevent viral or bacterial infections. In other embodiments, the agent is administered prior to the vaccination, while in other embodiments the agent is administered after the vaccine is administered to the subject.

In yet another aspect, the invention features a method of decreasing, inhibiting, suppressing, ameliorating, or delaying a Th2-associated response (e.g., an allergic or an asthmatic response), in a subject in need thereof, the method comprising administering to a subject an agent that decreases expression or activity of tim-3, galectin-9 or both i.e. administering a tim-3 or a galectin-9 antagonist, or an agent that decreases the binding of galectin-9 to tim-3.

A "Th2-mediated disorder" as used herein refers to a disease that is associated with the development of a Th2 immune response. A "Th2 immune response" as used herein refers to the induction of at least one Th2-cytokine or a Th2-antibody. In preferred embodiments more than one Th2-cytokine or Th2-antibody is induced. Thus a Th2-mediated disease is a disease associated with the induction of a Th2 response and refers to the partial or complete induction of at least one Th2-cytokine or Th2-antibody or an increase in the levels of at least one Th2-cytokine or Th2-antibody. These disorders are known in the art and include for instance, but are not limited to, atopic conditions, such as asthma and allergy, including allergic rhinitis, gastrointestinal allergies, including food allergies, eosinophilia, conjunctivitis, glomerulonephritis, certain pathogen susceptibilities such as helminthic (e.g., leishmaniasis) and certain viral infections, including human immunodeficiency virus (HIV), and certain bacterial infections, including tuberculosis and lepromatous leprosy. In a preferred embodiment, the Th2-associated response is asthma or an allergy.

Asthma, as defined herein, is reversible airflow limitation in an individual over a period of time. Asthma is characterized by the presence of cells such as eosinophils, mast cells, basophils, and $CD25^+$ T lymphocytes in the airway walls. There is a close interaction between these cells, because of the activity of cytokines which have a variety of communication and biological effector properties. Chemokines attract cells to the site of inflammation and cytokines activate them, resulting in inflammation and damage to the mucosa. With chronicity of the process, secondary changes occur, such as thickening of basement membranes and fibrosis. The disease is characterized by increased airway hyper-responsiveness to a variety of stimuli, and airway inflammation. A patient diagnosed as asthmatic will generally have multiple indications over time, including wheezing, asthmatic attacks, and a positive response to methacholine challenge, i.e., a PC20 on methacholine challenge of less than about 4 mg/ml. Guidelines for diagnosis may be found, for example, in the National Asthma Education Program Expert Panel Guidelines for Diagnosis and Management of Asthma, National Institutes of Health, 1991, Pub. No. 91-3042.

As used herein, "allergy" shall refer to acquired hypersensitivity to a substance (allergen). Allergic conditions include eczema, allergic rhinitis or coryza, hay fever, bronchial asthma, urticaria (hives) and food allergies, and other atopic conditions. A "subject having an allergy" is a subject that has or is at risk of developing an allergic reaction in response to an allergen. An "allergen" refers to a substance that can induce an allergic or asthmatic response in a susceptible subject. The list of allergens is enormous and can include pollens, insect venoms, animal dander, dust, fungal spores and drugs (e.g., penicillin).

Allergens of interest include antigens found in food, such as strawberries, peanuts, milk proteins, egg whites, etc. Other allergens of interest include various airborne antigens, such as grass pollens, animal danders, house mite feces, etc. Molecularly cloned allergens include *Dermatophagoides pteryonyssinus* (Der P1); Lol pl-V from rye grass pollen; a number of insect venoms, including venom from jumper ant *Myrmecia pilosula; Apis mellifera* bee venom phospholipase A2 ($PLA_2$ and antigen 5S; phospholipases from the yellow jacket *Vespula maculifrons* and white faced hornet *Dolichovespula maculata*; a large number of pollen proteins, including birch pollen, ragweed pollen, Parol (the major allergen of *Parietaria officinalis*) and the cross-reactive allergen Parjl (from *Parietaria judaica*), and other atmospheric pollens including *Olea europaea, Artemisia* sp., gramineae, etc. Other allergens of interest are those responsible for allergic dermatitis caused by blood sucking arthropods, e.g. Diptera, including mosquitos (*Anopheles* sp., *Aedes* sp., *Culiseta* sp.,

*Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order *Siphonaptera*, including the genera *Xenopsylla, Pulex* and *Ctenocephalides felis*. The specific allergen may be a polysaccharide, fatty acid moiety, protein, etc.

One specific aspect of the invention provides a method of preventing or reducing the likelihood of being afflicted with an atopic disease in a subject, the method comprising administering to the subject a therapeutically effective amount of a polypeptide, said polypeptide comprising (i) SEQ ID NO: 10; (ii) SEQ ID NO: 18; (iii) an amino acid sequence that is at least 90% identical or similar to SEQ ID NO: 10; or (iv) an amino acid sequence that is at least 90% identical or similar to SEQ ID NO: 18.

According to the present invention, agents which modulate tim-3 or galectin-9 activity, or modulate complex formation between tim-3 and galectin-9, may be used in combination with other compositions and procedures for the modulation of an immune responses or for treatment of a disorder or conditions. For example, a tumor may be treated conventionally with surgery, radiation or chemotherapy. Agents which decreases tim-3 activity, such as a soluble tim-3-IgFc fusion protein, may be subsequently administered to the patient to extend the dormancy of micrometastases and to stabilize any residual primary tumor.

In some embodiments, the agents which decrease tim-3 activity preferentially inhibit expression of soluble tim-3 relative to expression of full-length tim-3. In some embodiments, the agent which blocks tim-3 binding to galectin-9 is an antibody, or an antibody fragment such as an antibody fragment which retains high affinity binding to its antigen. Such an antibody may block tim-3/galectin-9 binding by binding either to galectin-9 or to tim-3, and in particular the extracellular domain of tim-3. In a specific embodiment, the agent is an antibody or antibody fragment that binds to a polypeptide comprising amino acids 30-128 of SEQ ID NO: 13.

Monoclonal antibodies can be generated, by one skilled in the art, which bind the tim-3 extracellular domain, and those antibodies can be further tested for their ability to block binding of a tim-3 ligand, such as galectin-9, to full-length tim-3 using the methods provided by the instant invention. The preferred antibodies would block the binding interactions between full-length tim-3 and its ligands without themselves acting as an activator of full-length tim-3 activity. Using the assays described in the experimental procedures for example, one skilled in the art can determine if a candidate antibody is an activator of tim-3 activity, such as by administering the antibody to an immunized mouse and testing for in vitro proliferation and cytokine production by Th1 cells isolated for the spleen of the mouse. Preferred antibodies for decreasing immune tolerance would both block binding of tim-3 ligands to tim-3 and not induce activation of tim-3 i.e. not suppress Th1 cell proliferation and cytokine release.

In one embodiment, the agent used to inhibit tim-3 function comprises an antibody. In one embodiment, the antibody binds to the IgV domain of tim-3 (amino acids 30-128 of SEQ ID NO: 13) and blocks binding of tim-3 ligands to full-length tim-3. In one embodiment, the tim-3 ligand is galectin-9. Accordingly, in another embodiment, the antibody binds to galectin-9. Upon binding, the antibody may prevent the physical interaction between galectin-9 and full-length tim-3.

In another embodiment, the agent which blocks binding of full-length tim-3 to galectin-9 in the subject comprises a recombinant tim-3 polypeptide that competes with the endogenous tim-3 for binding to galectin-9. In a specific embodiment, the agent comprises a polypeptide comprising (i) amino acids 30-128 of SEQ ID NO: 13; or (iii) an amino acid sequence that is at least 90% identical to amino acids 30-128 of SEQ ID NO: 13. In a specific embodiment, the polypeptide agent is pegylated and/or is a fusion protein with human serum albumin or with the Fc domain of an immunoglobulin. In another embodiment, the agent used in the methods to activate Th1 cells or to decrease immune tolerance in a subject comprises a soluble tim-3 polypeptide with an amino acid sequence according to SEQ ID NO: 2. In a preferred embodiment, the agent comprises the IgV domain of tim-3 (amino acids 30-128 of SEQ ID NO: 11). In yet another embodiment, the soluble tim-3 polypeptide comprises the IgV domain of tim-3, optionally the intracellular domain of tim-3, and the Fc domain of an immunoglobulin, but does not contain the mucin domain of tim-3 or the transmembrane domain of tim-3. In a preferred embodiment, these polypeptides bind galectin-9. Variants of these polypeptides, such as those which increase binding of tim-3 ligands, can also be used.

In some embodiments, the agent which decreases tim-3 activity inhibits binding of (i) a polypeptide comprising amino acids 30-128 of SEQ ID NO: 13; to (ii) galectin-9, such as the long or short forms of galectin-9.

Applicants have discovered that lactose inhibits binding of galectin-9 to tim-3. Accordingly, in one embodiment, the agent which inhibits binding of full-length tim-3 to galectin-9 comprises a carbohydrate, such as lactose or pectin/modified pectin. Modified pectins are described in U.S. Patent Pub. Nos. 2003/0004132 and 2002/0187959.

In another embodiment, the agent used in the methods described herein to activate promote Th1 responses and/or to inhibit Th2 responses decrease the expression level of full-length tim-3 polypeptide or of a tim-3 ligand, such as galectin-9 polypeptide. In one embodiments, the agent is a double stranded RNA species provided by the present invention, including those directed at full-length tim-3 or to a tim-3 ligand, such as galectin-9.

In a preferred embodiment, the agent used in the methods described herein to activate promote Th1 responses and/or to inhibit Th2 responses, or the agent used to inhibit tim-3 function, is a small organic molecule, e.g., other than a peptide or oligonucleotide, having a molecular weight of less than about 2,000 Daltons, which blocks the binding of tim-3 to its ligands, such as to galectin-9. Such agents can be identified, for example, using the methods provided by the invention. In another embodiment, the agent which inhibits tim-3 function is a peptide or peptide derivative which structurally mimics the portion of galectin-9 that binds tim-3. Such a peptide may act as an antagonistic competitor by preventing functional interactions between tim-3 and its ligand(s). In one embodiment, the ligand is galectin-9.

According to the present invention, agents which decrease the activity of tim-3, such as by reducing its expression level or reducing the formation of a tim-3/ligand complex, may be used in combination with other compositions and procedures for the treatment of hyperplastic conditions. For example, a tumor may be treated conventionally with surgery, radiation or chemotherapy, and double stranded RNA, antibodies or small molecule inhibitors against tim-3 or against tim-3 ligands, such as galectin-9, may be subsequently administered to the patient to extend the dormancy of micrometastases and to stabilize any residual primary tumor.

Another aspect of the invention provides a method of treating or preventing or reducing the likelihood of being afflicted with a Th1-mediated disorder in a subject in need of such treatment, the method comprising administering to the subject a therapeutically effective amount of an agent that increases expression or activity of tim-3, galectin-9 or both, or that increases the binding of tim-3 to galectin-9.

The invention also features a method of decreasing, inhibiting, suppressing, ameliorating, or delaying a Th1-mediated immune response, in a subject in need thereof, comprising administering to the subject a tim-3 or a galectin-9 agonist, e.g., a tim-3 or a galectin-9 agonist as described herein, in an amount sufficient to decrease, inhibit, suppress, ameliorate, or delay said Th1-mediated immune response in said subject.

In contrast to a Th2-mediated disorder, a "Th1-mediated disorder" as used herein refers to a disease that is associated with the development of a Th1 immune response. A "Th1 immune response" as used herein refers to the induction of at least one Th1-cytokine or a Th1-antibody. In preferred embodiments more than one Th1-cytokine or Th1-antibody is induced. Thus a Th1-mediated disease is a disease associated with the induction of a Th1 response and refers to the partial or complete induction of at least one Th1-cytokine or Th1-antibody or an increase in the levels of at least one Th1-cytokine or Th1-antibody. These disorders are known in the art and include for instance, but are not limited to, autoimmune (especially organ-specific) disease, psoriasis, Th1 inflammatory disorders, infection with extracellular parasites (e.g., response to helminths), solid organ allograft rejection (e.g., acute kidney allograft rejection), symptoms associated with hepatitis B (HBV) infection (e.g., HBV acute phase or recovery phase), chronic hepatitis C(HCV) infection, insulin-dependent diabetes mellitus (IDDM), multiple sclerosis (MS), subacute lymphocytic thyroiditis ("silent thyroiditis"), Crohn's disease, primary biliary cirrhosis, primary sclerosing cholangitis, sarcoidosis, atherosclerosis, acute graft-versus-host disease (GvHD), glomerulonephritis, anti-glomerular basement membrane disease, Wegener's granulomatosis, inflammatory myopathies, Sjogren's syndrome, Behget's syndrome, rheumatoid arthritis, Lyme arthritis, and unexplained recurrent abortion.

In some embodiments the Th1-mediated disorder is selected from the group consisting of atherosclerosis, infection with extracellular parasites, symptoms associated with hepatitis B (HBV) infection (e.g., HBV acute phase or recovery phase), chronic hepatitis C(HCV) infection, silent thyroiditis, primary biliary cirrhosis, primary sclerosing cholangitis, glomerulonephritis, anti-glomerular basement membrane disease, Wegener's granulomatosis, inflammatory myopathies, Sjogren's syndrome, Behcet's syndrome, rheumatoid arthritis, and unexplained recurrent abortion.

The methods described herein for decreasing Th1-mediated immune responses may be particularly beneficial to treat autoimmune diseases in a subject. In one embodiment, the methods of the present invention for reducing a Th1 response in a subject are directed at subjects afflicted with, or at high risk of developing an autoimmune disease. "Autoimmune disease" is a class of diseases in which a subject's own antibodies react with host tissue or in which immune effector T cells are autoreactive to endogenous self-peptides and cause destruction of tissue. Thus an immune response is mounted against a subject's own antigens, referred to as self-antigens.

A "self-antigen" as used herein refers to an antigen of a normal host tissue. Normal host tissue does not include cancer cells. Thus an immune response mounted against a self-antigen, in the context of an autoimmune disease, is an undesirable immune response and contributes to destruction and damage of normal tissue, whereas an immune response mounted against a cancer antigen is a desirable immune response and contributes to destruction of the tumor or cancer.

Autoimmune diseases include but are not limited to rheumatoid arthritis, Crohn's disease, multiple sclerosis, systemic lupus erythematosus (SLE), autoimmune encephalomyelitis, myasthenia gravis (MG), Hashimoto's thyroiditis, Goodpasture's syndrome, pemphigus (e.g., pemphigus vulgaris), Grave's disease, autoimmune hemolytic anemia, autoimmune thrombocytopenic purpura, scleroderma with anti-collagen antibodies, mixed connective tissue disease, polymyositis, pernicious anemia, idiopathic Addison's disease, autoimmune-associated infertility, glomerulonephritis (e.g., crescentic glomerulonephritis, proliferative glomerulonephritis), bullous pemphigoid, Sjogren's syndrome, insulin resistance, and autoimmune diabetes mellitus (type 1 diabetes mellitus; insulin-dependent diabetes mellitus). Recently autoimmune disease has been recognized also to encompass atherosclerosis and Alzheimer's disease. In one specific embodiment, the autoimmune disease is selected from the group consisting of multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis and myasthenia gravis. In another embodiment, the Th1-mediated disorder is host versus graft disease (HVGD). In a related embodiment, the subject is an organ or tissue transplant recipient.

Yet another aspect of the invention provides a method for increasing transplantation tolerance in a subject, comprising administering to the subject a therapeutically effective amount of an agent that increases tim-3 or galectin-9 function, expression, or binding of tim-3 to galectin-9. In one specific embodiment, the subject is a recipient of an allogenic transplant. The transplant can be any organ or tissue transplant, including but not limited to heart, kidney, liver, skin, pancreas, bone marrow, skin or cartilage. Transplantation tolerance, as used herein, refers to a lack of rejection of the donor organ by the recipient's immune system. Furthermore, the agents can be used for preventing or reducing the likelihood of being afflicted with rejection of tissue or cell transplants.

As used herein, the terms "agent" and "compound" include both protein and non-protein moieties. An agent can be any chemical (element, molecule, compound, drug), made synthetically, made by recombinant techniques or isolated from a natural source. For example, agents can be peptides, polypeptides, antibodies or antibody fragments, peptoids, sugars, hormones, or nucleic acid molecules (such as antisense or RNAi nucleic acid molecules). In addition, agents can be small molecules or molecules of greater complexity made by combinatorial chemistry, for example, and compiled into libraries. These libraries can comprise, for example, alcohols, alkyl halides, amines, amides, esters, aldehydes, ethers and other classes of organic compounds. Agents can also be natural or genetically engineered products isolated from lysates or growth media of cells—bacterial, animal or plant.

In one embodiment, the agent which increases tim-3 activity, such as those used to promote a Th2 response and/or inhibit a Th1 response, promotes the binding of full-length tim-3 to a ligand. In a preferred embodiment, the tim-3 ligand is galectin-9. The agent may be a polypeptide, which may itself bind to tim-3 or may itself bind to a tim-3 ligand, such as galectin-9, and increase the binding interaction between tim-3 and the ligand.

In one embodiment of the methods described herein, the agent which increases tim-3 activity is a tim-3 ligand. An example of such a ligand is galectin-9. Accordingly, in some embodiments said agent comprises a galectin-9 polypeptide. In another embodiment, said agent comprises a polypeptide comprising at least one of the two carbohydrate recognition domains (CRD) of galectin-9 i.e. at least the N-terminal or the C-terminal, or both.

In another embodiment, the agent which increases tim-3 activity comprises a polypeptide comprising an amino acid sequence which is at least 80% identical to the amino acid sequence set forth in SEQ ID NO: 10 or SEQ ID NO: 18. In other embodiments, the sequence is 85%, 90%, 95%, 96%, 97%, 98%, 99% or 100% identical to the amino acid sequence set forth in SEQ ID NO: 10 or SEQ ID NO: 18. In a specific embodiment, the polypeptide comprises an amino acid sequence which is at least 80%, 90% or 95% identical to the amino acid sequence of at least one CRD of human galectin-9.

In other embodiments, the agent which increases tim-3 activity is a peptide mimetic or a small molecule which can function as galectin-9 in activating the tim-3 receptor. The peptide or small molecule may structurally resemble the surface of galectin-9 that binds tim-3, such that the peptide or small molecule can activate tim-3 upon binding it, leading to increased tim-3 activity and activation of Th1 cells, which includes increased cell proliferation and secretion of cytokines. In a specific embodiment, the agent which increases tim-3 activity promotes the tyrosine phosphorylation of the intracellular domain of tim-3.

In another embodiment, the agent which increases tim-3 activity in the methods described herein in as an antibody or fragment thereof. Antibodies can be generated which bind to tim-3 and mimic the binding of a ligand, resulting in intracellular signaling. Upon generating an antibody that binds to the extracellular domain of tim-3, a skilled artisan may test whether the antibody activates tim-3, which would lead to a suppression of Th1 cell proliferation, reduced cytokine release, and increased tolerance. The methods described in the experimental procedure could be used to determine if an antibody binding activates full-length tim-3. In a specific embodiment, the antibody which increases tim-3 activity is a bispecific antibody specific for tim-3 and galectin-9.

In yet another embodiment, the agent which increases tim-3 activity reduces the expression or function of soluble tim-3, but does not directly affect that of full-length tim-3. In one embodiment, the agent is a double stranded RNA species which specifically inhibits the expression of soluble tim-3, such as the one comprising the nucleotide sequence according to SEQ ID NO: 15. Such double stranded RNA may be administered as a double-stranded hairpin RNA. In another embodiment, the agent which increases tim-3 activity is an antibody that specifically binds to soluble tim-3 but not to full-length tim-3, such as those provided by the invention.

Description of Sequence Listings

SEQ ID NO: 1 is the coding sequence of human soluble tim-3 isoform
SEQ ID NO: 2 is human soluble tim-3 protein
SEQ ID NO: 3 is the coding sequence of mouse soluble tim-3 isoform
SEQ ID NO: 4 is mouse soluble tim-3 protein
SEQ ID NO: 5 is a 16 nucleotide DNA fragment identical to the novel splice junction of human soluble tim-3 cDNA
SEQ ID NO: 6 is a 16 amino acid peptide identical to the novel IgV domain/Intracellular domain junction of human soluble tim-3 protein
SEQ ID NO: 7 is a 16 bp DNA fragment identical to the novel splice junction of mouse soluble tim-3 cDNA
SEQ ID NO: 8 is a 16 amino acid peptide identical to the novel IgV domain/intracellular domain junction of mouse soluble tim-3 protein
SEQ ID NO: 9 is the coding sequence of human galectin-9, short form.
SEQ ID NO: 10 is the amino acid sequence of human galectin-9, short form.
SEQ ID NO: 11 is the coding sequence of full-length human tim-3.
SEQ ID NO: 12 is the coding sequence of full-length mouse tim-3.
SEQ ID NO: 13 is the amino acid sequence of full-length human tim-3.
SEQ ID NO: 14 is the amino acid sequence of full-length mouse tim-3.
SEQ ID NO: 15 is a 16 nucleotide RNA sequence corresponding to the novel splice junction of human soluble tim-3.
SEQ ID NO: 16 is the coding sequence of mouse galectin-9.
SEQ ID NO: 17 is the amino acid sequence of mouse galectin-9.
SEQ ID NO: 18 is the amino acid sequence of mouse galectin-9, long form. (see also Genbank Accession No. NP_034838)
SEQ ID NO: 19 is the amino acid sequence of human galectin-9, long form. (see also Genbank Accession No. NP_033665)

EXEMPLIFICATION

The invention now being generally described, it will be more readily understood by reference to the following examples which are included merely for purposes of illustration of certain aspects and embodiments of the present invention, and are not intended to limit the invention.

The examples are divided into two series, each series having its own description of the methods used in the examples.

First Series of Experiments

A. METHODOLOGY

Cloning of s-Tim-3

Splenocytes were activated with 1 μg/mL concanavalin A (Sigma, St. Louis, Mo.). 48 hours post-activation, cells were harvested and RNA extracted using TRIzol reagent (Invitrogen) as per manufacturers' instructions. RNA was reverse transcribed using Superscript II reverse transcription kit (Invitrogen, Los Angeles, Calif.). Tim-3 primers, with SmaI restriction overhangs, were designed in the 5' (TIM-3-F: 5' GCCCGGGAGGAGCTAAAGCTATCCCTACACA3') and 3' (TIM3-R: 5' GCCCGGGCCAATGAGGTTGCCAAGTGACATA 3') UTR of the Tim-3 gene, for the amplification of both fl-Tim-3 and s-Tim-3. Reactions were carried out in a DNA Thermal cycler (Perkin-Elmer, Chicago, Ill.) for 35 cycles with denaturation at 95° C. for 1 min, annealing at 55° C. for 30 sec and extension at 72° C. for 90 sec per cycle. Reactions were completed with a final 10 min extension at 72° C. All products were resolved on a 1.2% agarose gel and visualized using ethidium bromide.

T Cell Sort and Tim-3-Ligand Staining

Whole spleen and lymph node cells were harvested from naïve C57BL/6 mice (Jackson Laboratories, Bar Harbor, Me.), and CD4+ T cells were column purified (R&D Systems, Minneapolis, Minn.). CD4+ T cells were stained with mAbs to CD25, CD62L, CD45RB, CD44 and CD54 (Pharmingen, San Diego, Calif.). Cells were stained with biotinylated ex-Tim-3-Ig, s-Tim-3-Ig or hIgG, and streptavidin-PE was used as the secondary detection reagent for detection in flow cytometry.

AE7, a pigeon cytochrome c specific, I-$E^k$-restricted Th1 clone[34,35] and LR1F1, a PLP 139-151 altered peptide Q144 (HSLGKQLGHPDKF) specific, I-$A^s$ restricted Th2 clone[36] were maintained in DMEM supplemented with 0.1 mM non-essential amino acids, sodium pyruvate (1 mM), L-glutamine (2 mM), MEM essential vitamin mixture (1×), penicillin (100 U/ml), streptomycin (100 U/ml), gentamicin (0.1 mg/ml), 10% heat-inactivated fetal bovine serum (BioWhittaker, Incorporated, Walkersville, Md.), asparagine (0.1 mM), folic acid (0.1 mg/ml) and 2-mercaptoethanol ($5 \times 10^{-5}$ M) (Sigma, St. Louis, Mo.), 0.6% T cell growth factor (T-Stim, Collaborative Biomedical Research, Bedford, Mass.) and 0.06% recombinant IL-2. Cells were maintained in a rest/stimulation protocol (stimulation media is complete medium without T-Stim and r-IL-2) as described[6,34], and stained for s-Tim-3-Ig binding.

Proliferation Assays

Female SJL/J mice (6-12 weeks old) (Jackson Laboratory, Bar Harbor, Me.) were injected subcutaneously (s.c.) in each flank with 50 μg PLP 139-151 peptide (HSLGKWLGHP-DKF) (Quality Controlled Biochemicals, Boston, Mass.) emulsified in complete Freund's adjuvant (CFA) (Difco, Kansas City, Mo.). Mice were injected intraperitoneally every other day (beginning the same day as immunization, day 0, and continuing through day 8) with either 100 μg ex-Tim-3-Ig or s-Tim-3-Ig, or 100 μg control hIgG or 100 μl PBS. Mice were sacrificed on day 10, and spleens were removed. Cells were plated at $5 \times 10^5$ cells/well in round bottom 96 well plates (Falcon, Becton Dickinson, Los Angeles, Calif.) with PLP 139-151 added at 0-100 μg/ml for 48 hrs, and plates were pulsed with 1 μCi $^3$[H]-thymidine/per well for 16-18 hrs. The incorporated radiolabeled thymidine was measured utilizing a Beta Plate scintillation counter (Perkin Elmer Wallac Inc, Atlanta, Ga.). The data are presented as mean cpm in triplicate wells.

For cell separation experiments, $CD11b^+$ and $B220^+$ cells were purified through positive selection by MACS Sort magnetic beads (Miltenyi Biotech, Auburn, Calif.), and $CD3^+$ T cells were purified by negative selection columns after depletion of $CD11b^+$ and $B220^+$ cells (R&D Systems, Minneapolis, Minn.). $CD3^+$ T cells were plated at $10^5$ cells/well, and $CD11b^+$ and $B220^+$ cells were plated at $2 \times 10^5$ cells/well.

For tolerance induction experiments, SJL mice were immunized s.c. with 50 μg PLP 139-151/CFA and concurrently given an intraperitoneal injection of 500 μg soluble PLP 139-151 to induce tolerance. Spleen cells were plated at $5 \times 10^5$ cells/well and lymph node cells at $2 \times 10^5$ cells/well.

Cytokine ELISAs

Cytokine production was measured for IL-2, IL-4, IL-10, IFN-γ and TNF-α by quantitative capture ELISA. Briefly, purified rat mAb to mouse IL-2 (clone JES-1A12), IL-4 (clone BVD4-1D11), IL-10 (clone JES5-2A5), IFN-γ (clone R4-6A2) and TNF-α (clone G281-2626) were obtained from Pharmingen (San Diego, Calif.) and used to coat ELISA plates (Immulon 4, Dynatech Laboratories, Chantilly, Va.). Recombinant mouse cytokines from Pharmingen were used to construct standard curves, and biotinylated rat mAbs to mouse IL-2 (clone JES6-5H4), IL-4 (clone BVD6-24G2), IL-10 (clone SXC-1), IFN-γ (clone XMG1.2) and TNF-α (clone MP6-XT3) were used as the second antibody. Plates were developed with TMB microwell peroxidase substrate (Kirkegaard and Perry Laboratories, Gaithersburg, Md.) and read after the addition of stop solution at 450 nm using a Benchmark microplate reader (Bio-Rad Laboratories, Hercules, Calif.).

BrdU Incorporation

Spleens were taken from PLP 139-151/CFA immunized, Tim-3-Ig or hIgG treated mice at day 10, and $5 \times 10^5$ to $1 \times 10^6$ whole spleen cells (96 well, round bottom plates) were incubated for 48 h at 37° C., 10% $CO_2$ with 5-10 μM 5-bromodeoxyuridine (Sigma, St. Louis, Mo.). After 48 h, cells were stained with mAb to CD3-CyC, CD25-PE, and CD69-PE (Pharmingen, San Diego, Calif.). Cells were subsequently fixed and permeabilized (Cytoperm, Pharmingen, San Diego, Calif.), and treated with DNAse I (Sigma, St. Louis, Mo.). Cells were then stained with FITC-conjugated mAb to BrdU (or mouse IgG1 as isotype control) and analyzed by FACS (Becton Dickinson, Los Angeles, Calif.).

B. EXAMPLES OF FIRST SERIES OF EXPERIMENTS

Example 1

Identification of Soluble Tim-3 Containing the Extracellular Immunoglobulin Domain but Lacking the Mucin Domain of Full-Length Tim-3

Figure 1C:
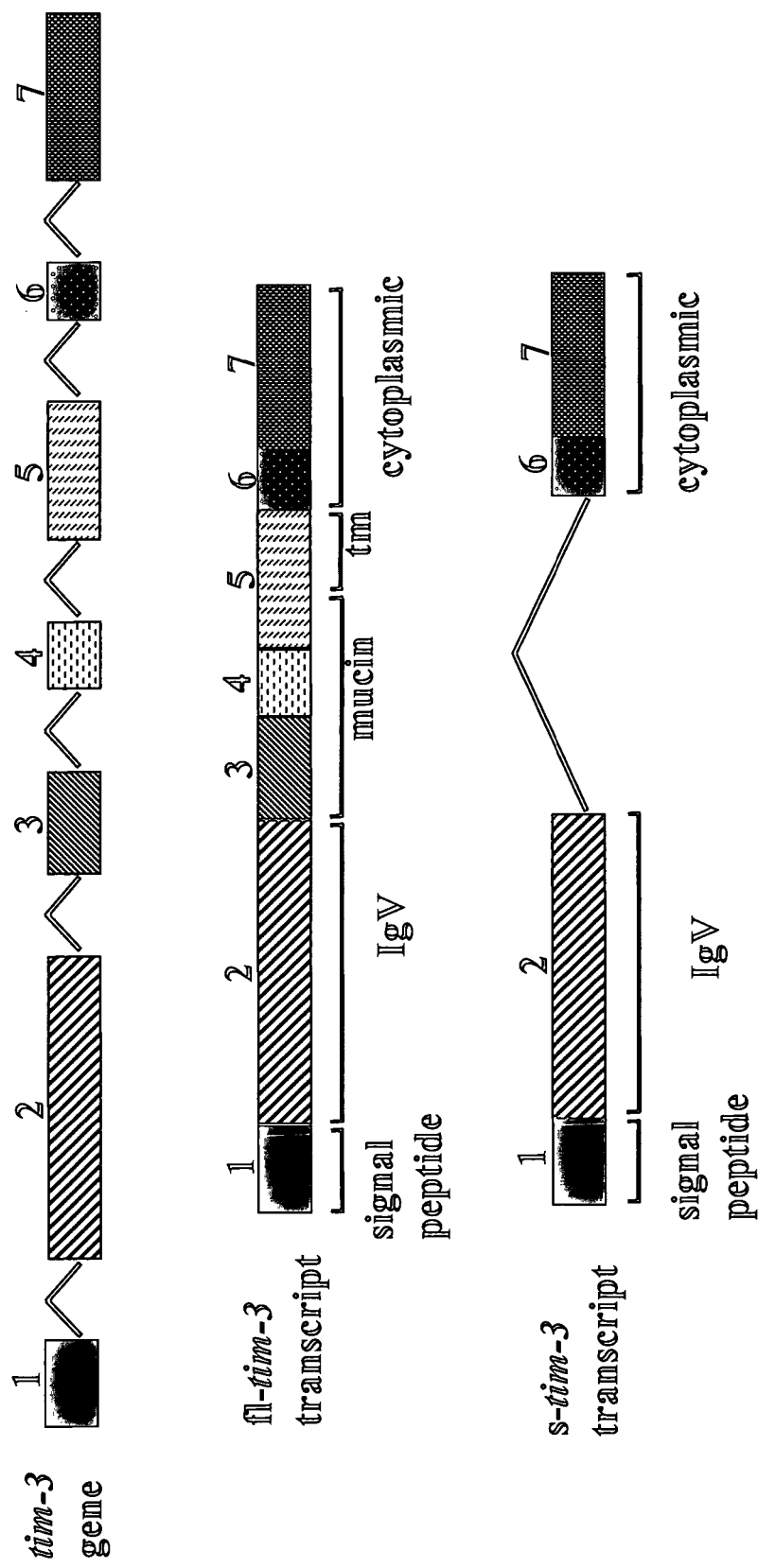

Primers were designed in the 5' and 3' untranslated regions (UTRs) of the murine Tim-3 gene and were used to amplify Tim-3 from cDNA generated from concanavalin A (con-A) activated splenocytes by PCR. In addition to the full-length form of Tim-3 of approximately 1 kb, another amplicon 800 bp in size was identified (FIG. 1A, lane 1). The predicted amino acid translation of the 1 kb amplicon demonstrated an open reading frame (ORF) consistent with the full-length, membrane-anchored form of Tim-3 (fl-Tim-3), containing signal peptide, IgV, mucin, transmembrane and cytoplasmic domains (FIG. 1B). Analysis of the ORF from the 800 bp product demonstrated the presence of a novel isoform of Tim-3 which contained only the signal peptide, IgV and cytoplasmic domains, and lacked the mucin domain and transmembrane region (FIG. 1B, 1C). The absence of the mucin and transmembrane domains was consistent with the splicing of exons 3, 4 and 5 from the murine Tim-3 gene (FIG. 1C). These data suggest that the product encoded by the 800 bp amplicon is an alternatively spliced, soluble form of Tim-3 (s-Tim-3), containing the IgV portion of the extracellular domain of murine TIM-3 fused to the cytoplasmic domain.

Example 2

Construction of Soluble Tim-3-Ig Fusion Proteins

To identify potential Tim-3-Ligand(s) and their functional in vivo interactions with TIM-3, soluble fusion proteins were designed for both the full-length and soluble forms of Tim-3 (21). The cDNA encoding the entire extracellular portion of mouse Tim-3 but without transmembrane and cytoplasmic tail, was fused to cDNA encoding a human IgG1 Fc tail to form full-length Tim-3-Ig fusion protein (ex-Tim-3-Ig). In light of the existence of a secreted form of Tim-3 containing only the IgV portion of the extracellular domain (FIG. 1A, 1B), a second fusion protein was constructed composed of cDNA encoding the IgV portion of mouse Tim-3 fused with cDNA encoding the human IgG1 Fc tail to form soluble Tim-3-Ig fusion protein (s-Tim-3-Ig). These constructs were stably transfected into NS.1 B cells, and the proteins were purified from the supernatants(21).

Example 3

CD4+ T cells express Tim-3-Ligand

Figure 2A:
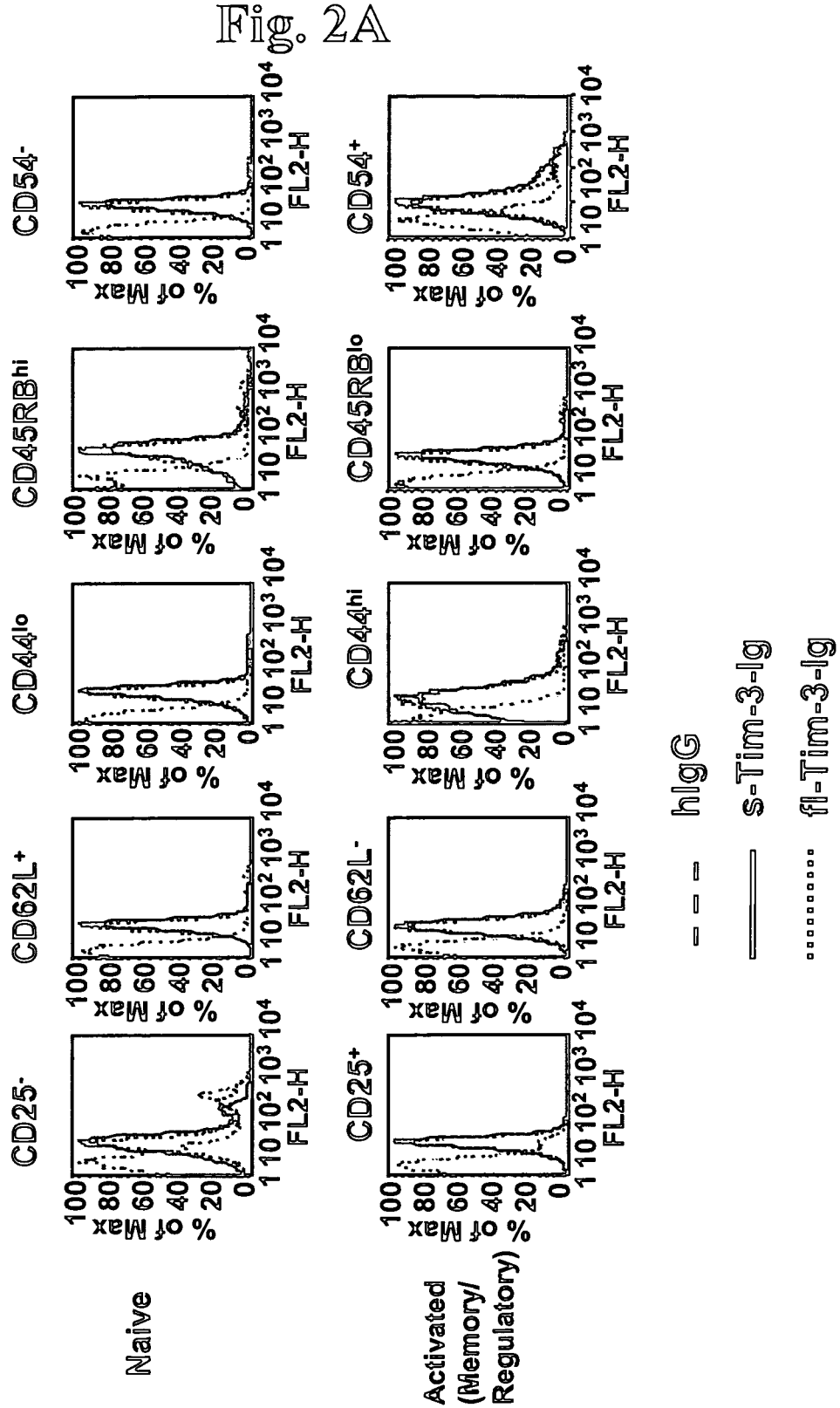
FIG. 2 shows that Tim-3-Ligand is expressed on $CD4^+$ T cells. (a) Whole spleen cells from C57BL/6 mice were $CD4^+$ column purified, stained with and gated for CD4 expression, and co-stained for various cell-surface markers (CD25, CD62L, CD44, CD45RB and CD54). Cells were co-stained for Tim-3-Ig with biotinylated ex- or s-Tim-3-Ig, followed by streptavidin-PE as a secondary reagent for detection. Cells were gated on $CD4^+$, and surface marker positive or negative populations. Legend: (Thin dashed line) hIgG; (Solid thick line), s-Tim-3-Ig; and (Thick dotted line), ex-Tim-3-Ig. (b) Th1 (AE7) and Th2 (LR1F1) clones were stained with biotinylated s-Tim-3-Ig or hIgG, followed by streptavidin-PE. Cells were stained as resting cells (day 0), as activated cells at 4 days post-activation (day 4) and as resting cells at 10 days post-activation (day 10). Legend (Thin dashed line) hIgG; (Solid thick line), s-Tim-3-Ig.

To determine which cells express Tim-3-Ligand, whole spleen cells from naïve, unimmunized SJL/J, NOD, C57BL/6 and BALB/c mice were stained with ex-Tim-3-Ig or s-Tim-3-Ig, and co-stained for various cell surface markers. When analyzed by flow cytometry, CD4+ T cells obtained from each strain were positive for Tim-3-Ligand expression when stained with either s-Tim-3-Ig or ex-Tim-3-Ig fusion proteins. When purified CD4+ T cells were co-stained for a panel of cell surface activation markers, it was found that both naïve ($CD25^-$, $CD62L^+$, $CD44^{lo}$, $CD45RB^{hi}$, $CD54^-$) and activated, memory/regulatory ($CD25^+$, $CD62L^-$, $CD44^{hi}$, $CD45RB^{lo}$, $CD54^+$) populations expressed Tim-3-Ligand as assessed by both ex-Tim-3-Ig and s-Tim-3-Ig staining (FIG. 2A). When CD4+ T cells were purified and sorted for CD25 expression, both $CD4^+25^+$ and $CD4^+25^-$ populations expressed Tim-3-Ligand. However, when sorted cells were activated for 48 h in vitro with increasing concentrations of anti-CD3/anti-CD28 and IL-2, $CD4^+CD25^+$ T cells retained expression of Tim-3-Ligand whereas $CD4^+CD25^-$ cells downregulated. A small fraction of $CD11c^+$ dendritic cells and $CD11b^+$ macrophages from whole spleen were also stained by the Tim-3-Ig fusion proteins, but B cells ($B220^+$, $CD19^+$) from whole spleen did not stain for Tim-3-Ligand with either fusion protein.

Figure 2B:
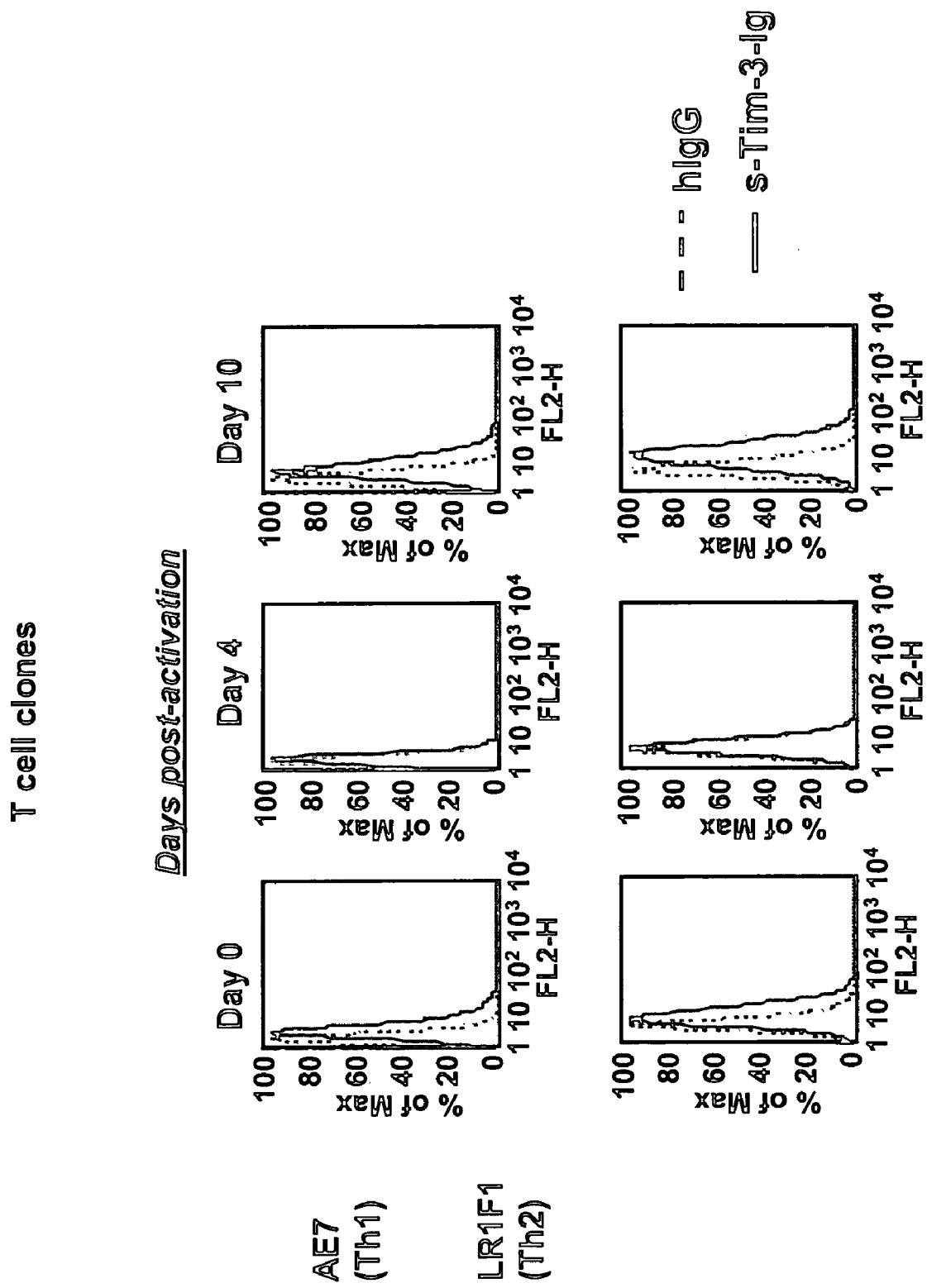

Since CD4+ T cells stained positively with the Tim-3-Ig fusion proteins, a panel of long term Th1 or Th2 clones was tested for the expression of Tim-3-Ligand to determine whether there was selective expression of Tim-3-Ligand on Th1 or Th2 cells. Interestingly, both Th1 and Th2 cells were positive for staining with s-Tim-3-Ig in the resting state (day 0, FIG. 2B), while activation of these cell lines downregulated Tim-3-Ligand expression (day 4, FIG. 2b). Between 7-10 days after activation, the Tim-3-Ligand expression was upregulated on the now quiescent T cell clones (day 10, FIG. 2b). Thus, it appears that Tim-3-Ligand is expressed on both resting Th1 and Th2 cells and that expression is downregulated upon activation. These data are consistent with the data from the second series of experiments which demonstrate that $CD4^+CD25^-$ T cells (which contain effector T cells) downregulate Tim-3-Ligand expression upon activation.

Example 4

In Vivo Administration of Tim-3-Ig Induces Hyperproliferation

Figure 3A:
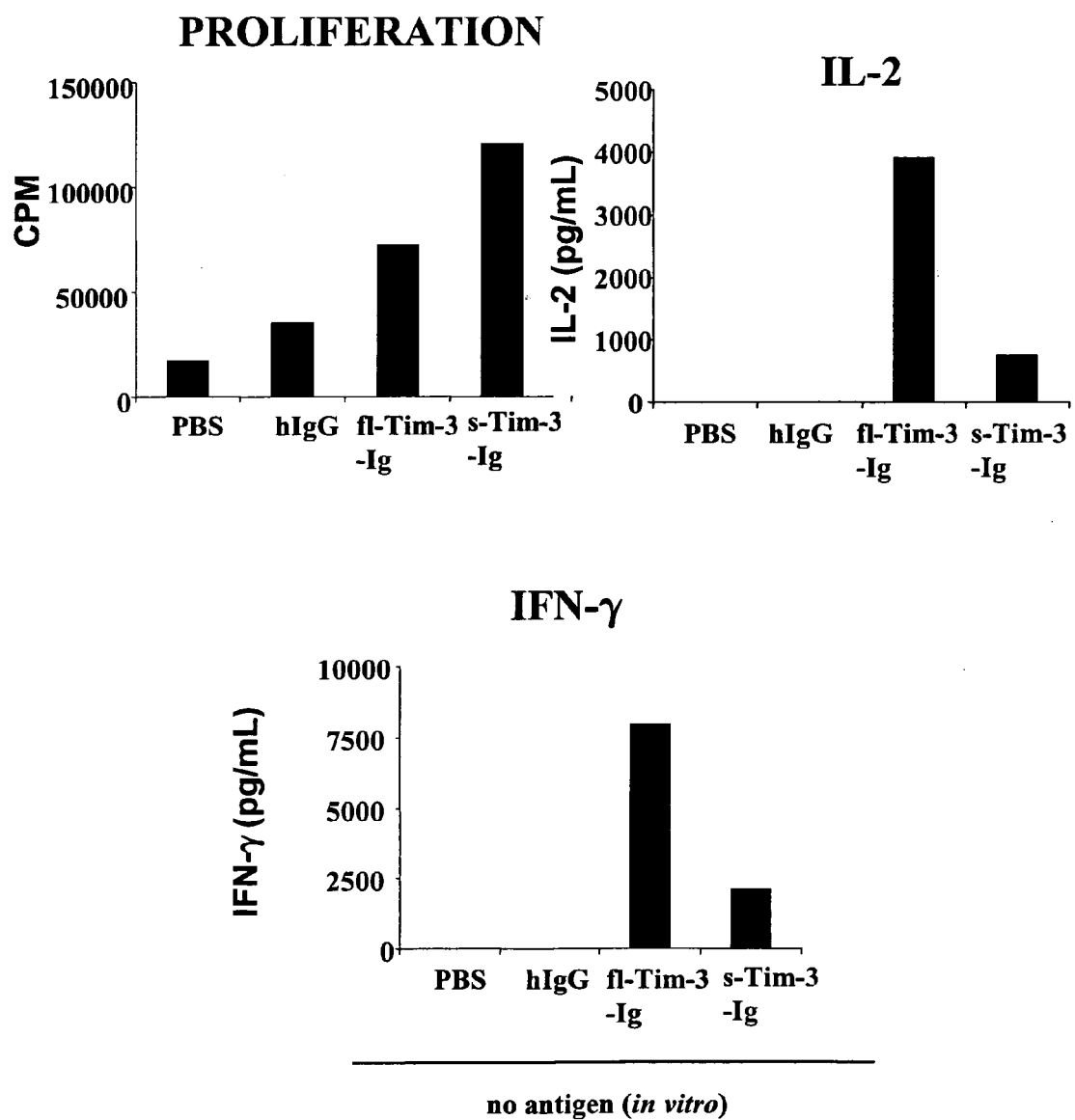
FIG. 3 shows that administration of Tim-3-Ig induced hyperproliferation and spontaneous production of Th1 cytokines. (a) SJL/J mice were immunized with PLP 139-151/CFA and injected intraperitoneally every other day from day 0-8 with 100 μg ex-Tim-3-Ig or s-Tim-3-Ig, or hIgG (100 μg) or PBS (100 μl) as controls. Mice were sacrificed on day 10, and spleens were removed and cultured in vitro for 48 h without peptide restimulation. Proliferation was measured in triplicate wells after 48 h by $^3$H-thymidine incorporation. Supernatants were taken at 48 h and used in cytokine ELISAs; IL-2 and IFN-γ production are shown; no IL-4, IL-10 or TNF-α was detected. Data shown for individual mice; representative of 10 experiments for proliferation and five experiments for cytokines. (b) The spleen cells taken from immunized, fusion-protein treated mice on day 10 were stimulated in vitro with 0-100 μg of PLP 139-151 peptide. Proliferation was measured after 48 h by $^3$H-thymidine incorporation in triplicate wells. Supernatants were taken at 48 h from in vitro cultures of whole spleen cells restimulated with PLP 139-151 peptide, and cytokine ELISAs for IL-2, IL-4, IL-10, TNF-α and IFN-γ were performed. IL-2 and IFN-γ production are shown; no IL-4, IL-10 or TNF-α was detected. Legend: ▲, PBS; ■, hIgG; ●, ex-Tim-3-Ig; and ○, s-Tim-3-Ig-treated. Data shown for individual mice; representative of 10 experiments for proliferation and five experiments for cytokines.
Figure 3B:
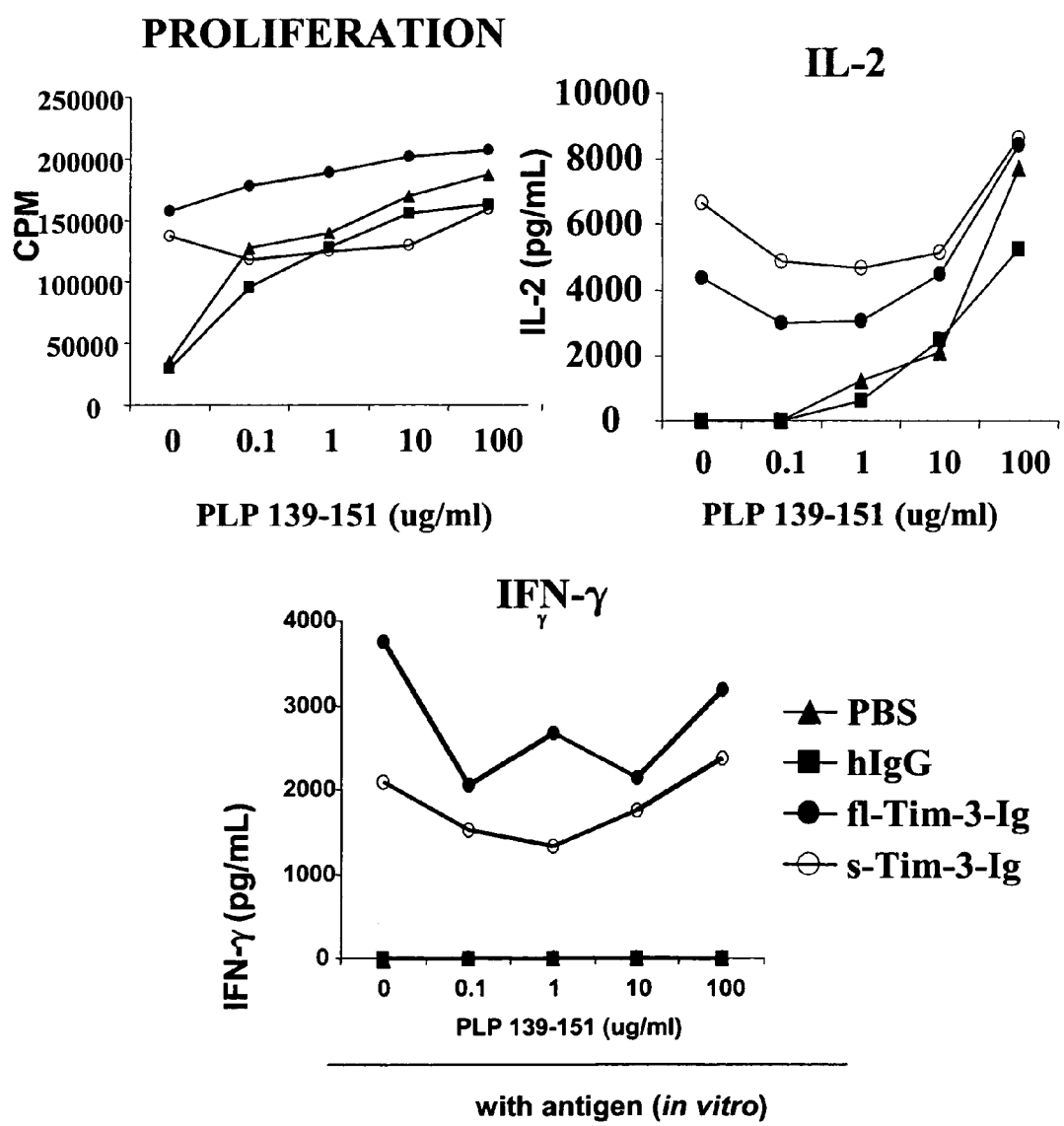

To determine the in vivo role of Tim-3/Tim-3-Ligand interaction during the course of a Th1 immune response, SJL/J mice were immunized with myelin proteolipid protein PLP 139-151 in complete Freund's adjuvant (CFA) and treated with either ex-Tim-3-Ig or s-Tim-3-Ig, and human IgG (hIgG) or PBS as controls. The treated mice were sacrificed on day 10, and spleen cells were restimulated in vitro to determine proliferation and cytokine production. Whole spleen cells from control hIgG- or PBS-treated mice showed a low background (basal) response in the absence of antigenic restimulation (FIG. 3A) and demonstrated a dose-dependent increase in proliferation with the addition of PLP 139-151 peptide (FIG. 3B). Conversely, spleen cells from mice treated with ex-Tim-3-Ig or s-Tim-3-Ig had a very high basal proliferation in the absence of antigenic restimulation, which in some experiments was as high as 120,000 cpm (FIG. 3A). However, no major enhancement in the proliferative response was observed when specific antigen (PLP 139-151) was titrated into cell cultures from ex-Tim-3-Ig- or s-Tim-3-Ig-treated mice (FIG. 3B). Taken together, these data suggest that spleen cells from immunized mice treated with either fusion protein rapidly proliferate in vivo such that they continue to proliferate in vitro without further antigenic stimulation (FIGS. 3A, 3B).

Example 5

In Vivo Administration of Tim-3-Ig Induces Amplified Th1 Cytokine Production

To determine whether the proliferating cells also produce cytokines, supernatants were harvested from in vitro cultures at 48 hours and analyzed by cytokine ELISAs for IL-2, IL-4, IL-10, TNF-α and IFN-γ. Analysis revealed that spleen cells from immunized SJL/J mice treated with ex-Tim-3-Ig or s-Tim-3-Ig produced large quantities of the Th1 cytokines IL-2 and IFN-γ, without antigenic restimulation (FIG. 3A). In contrast, spleen cells from mice treated with control PBS or hIgG did not produce IL-2 or IFN-γ in the absence of antigenic restimulation (FIG. 3A). Spleen cells from mice treated with ex-Tim-3-Ig or s-Tim-3-Ig also secreted high amounts of IL-2 and IFN-γ in vitro following PLP 139-151 peptide restimulation (FIG. 3B). Spleen cells from mice treated with control PBS or hIgG produced little or no IFN-γ, and only produced IL-2 upon PLP 139-151 peptide restimulation (FIG. 3B). Taken together, these data suggest that in vivo treatment with either ex-Tim-3-Ig or s-Tim-3-Ig induced hyperproliferation of Th1 cells and release of Th1 cytokines ex vivo.

Example 6

Figure 4A:
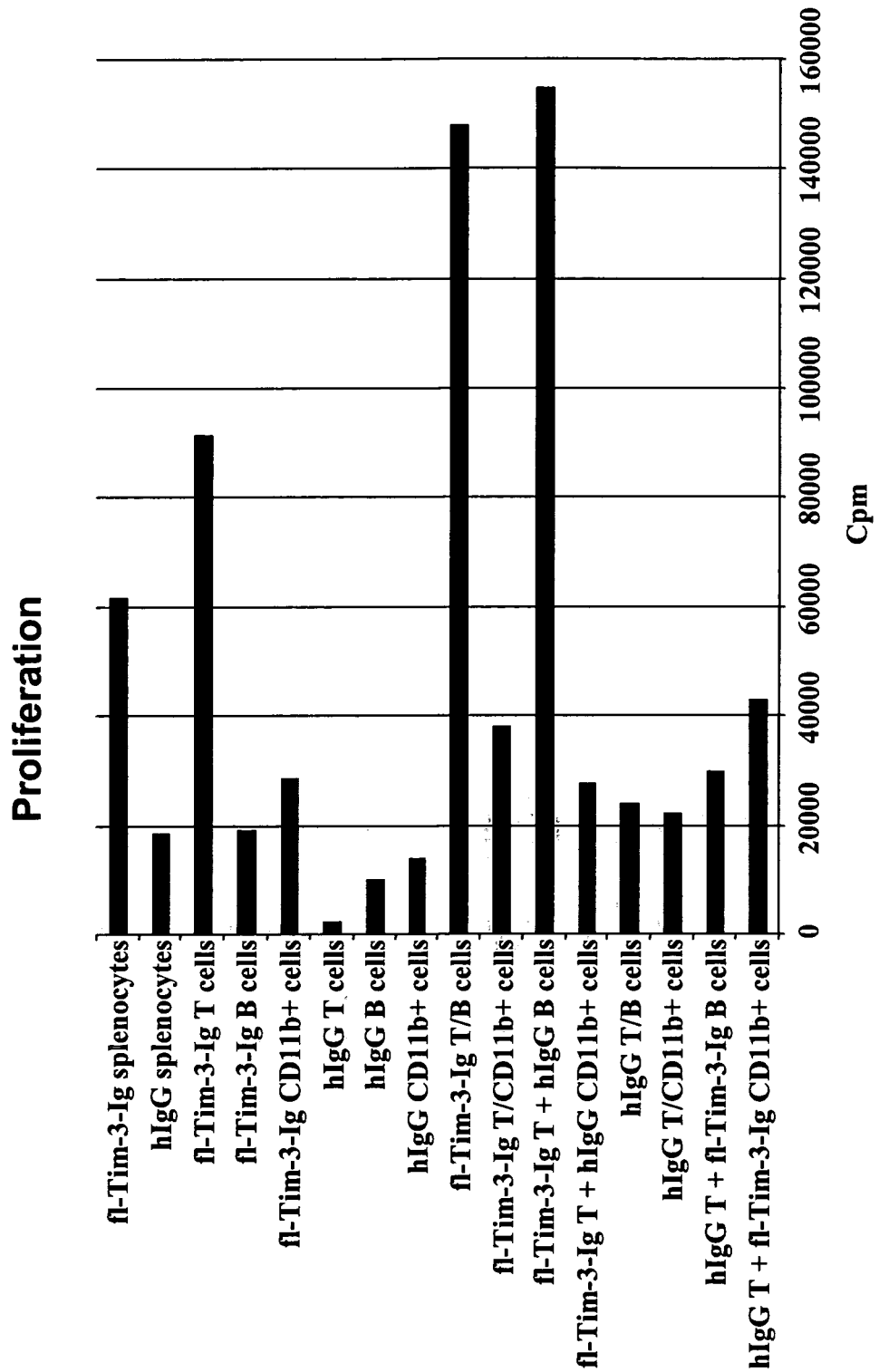
FIG. 4 shows that spontaneous hyperproliferation and cytokine release is mediated by T cells. (a) SJL/J mice were immunized with PLP 139-151/CFA and treated with 100 μg intraperitoneally (every other day from days 0-8) of ex-Tim-3-Ig or hIgG as control, and sacrificed on day 10. T, B and $CD11b^+$ cells were purified from the spleen. Either whole splenocytes ($5\times10^5$) or T cells ($10^5$) were incubated in the presence or absence of either $2\times10^5$ B cells, $2\times10^5$ $CD11b^+$ cells or both, and the proliferative response was measured ($^3$H-thymidine incorporation in triplicate wells). Results are represented as average for four mice combined; representative of three experiments. (b) Supernatants were taken from the in vitro cultures described in (a) at 48 h, and cytokine ELISAs for IL-2, IL-4, IL-10, TNF-α and IFN-γ were performed. IL-2 and IFN-γ production are shown; no IL-4, IL-10 or TNF-α was detected. Results are represented as average for four mice combined. (c) SJL/J mice were immunized with PLP 139-151/CFA and given 100 μg intraperitoneally every other day from day 0-8 of ex-Tim-3-Ig, s-Tim-3-Ig or hIgG as control, and spleens were taken on day 10. Whole spleen cells ($5\times10^5$ to $10^6$ cells) were cultured in vitro with 10 μM BrdU. After 48 h, cells were stained with mAbs to CD3, CD25, CD69 and BrdU. Dot plots (logarithmic scale) represent cell populations and BrdU incorporation. Results are for individual mice; representative of four experiments.

Hyperproliferation and Th1 Cytokine Production is Mediated by T Cells in Tim-3-Ig Treated Mice To determine the phenotype of the cell types that proliferate in immunized, Tim-3-Ig-treated mice, individual cell populations of $CD3^+$ T cells, $CD11b^+$ macrophages and $B220^+$ B cells were purified from the spleens of immunized mice. After purification, cell populations were cultured separately or re-combined in vitro and assessed for their ability to proliferate as detected by $^3[H]$-thymidine incorporation. Of all the cell types, purified $CD3^+$ T cells from mice treated with ex-Tim-3-Ig proliferated vigorously without peptide restimulation, whereas $CD3^+$ T cells from control hIgG-treated mice demonstrated only low background levels of proliferation (FIG. 4A). Individual populations of $B220^+$ B cells or $CD11b^+$ cells from control hIgG-treated mice showed low proliferation (approximately 10,000 cpm; FIG. 4A). While the B cells and $CD11b^+$ cells from ex-Tim-3-Ig-treated mice showed twice as much proliferation (approximately 20,000 cpm; FIG. 4A) as those from the hIgG-treated control mice, this proliferation was minimal in comparison to that of the $CD3^+$ T cells from the ex-Tim-3-Ig-treated mice. This suggested that T cells, and not $B220^+$ B cells or $CD11b^+$ macrophages, harvested from the ex-Tim-3-Ig-treated mice were hyperproliferating. This is in contrast to the observation in anti-TIM-3 antibody treated mice, where the majority of activation and expansion was seen in the $CD11b^+/F4-80^+$ macrophage population, and not in the T or B cell compartments (20). The dependence on lymphocytes for the hyperproliferation phenotype in the Tim-3-Ig-treated mice is further supported by data obtained from administration of Tim-3-Ig to immunized RAG-2$^{-/-}$ mice. When SJL-RAG-2$^{-/-}$ mice were immunized with PLP 139-151 in CFA and treated with ex-Tim-3-Ig or s-Tim-3-Ig, there was no proliferative background or response to antigenic restimulation observed, suggesting that the background response seen in spleen cells taken from immunized, fusion protein-treated mice was dependent on the presence of T and/or B cells. Administration of ex-Tim-3-Ig or s-Tim-3-Ig to unimmunized mice also increased the background proliferative response, but this was not due to a polyclonal response to the human Fc tail present in the fusion proteins since the T cell response could not be recalled with either human Ig or either of the Tim-3-Ig fusion proteins. Furthermore, administration of human Ig in unimmunized mice did not induce a basal proliferative response (FIG. 3A). This suggests that a subtle ongoing immune response in the unimmunized mice can also be uncovered by the administration of Tim-3-Ig.

When CD3$^+$ T cells from hIgG-treated mice were mixed with B220$^+$ B cells or CD11b$^+$ cells from hIgG-treated mice, the proliferation remained low (approximately 20,000 cpm) and was only slightly increased by the addition of B220$^+$ B or CD11b$^+$ cells from ex-Tim-3-Ig-treated mice (approximately 30-40,000 cpm) (FIG. 4A). The greatest proliferation was discerned when CD3$^+$ T cells from ex-Tim-3-Ig-treated mice were cultured with B220$^+$ B cells from either the hIgG- or ex-Tim-3-Ig-treated mice (~150,000 cpm) (FIG. 4A). Interestingly, when CD3$^+$ T cells from ex-Tim-3-Ig-treated mice are mixed with CD11b$^+$ cells from either hIgG- or ex-Tim-3-Ig-treated mice, the spontaneous proliferation seen in CD3$^+$ T cells from Tim-3-Ig-treated mice was markedly decreased (down to 30-38,000 cpm from 90,000 cpm for purified CD3$^+$ T cells alone) (FIG. 4A). Taken together, these data suggest that administration of ex-Tim-3-Ig during an ongoing immune response induced hyperproliferation of CD3$^+$ T cells, with a smaller effect on the proliferation of APCs (B cells and macrophages). B220$^+$ B cells, regardless of their source, enhanced the proliferation of the T cells from ex-Tim-3-Ig-treated mice, whereas CD11b$^+$ macrophages inhibited the spontaneous hyperproliferation of CD3$^+$ T cells from ex-Tim-3-Ig-treated mice.

Figure 4B:
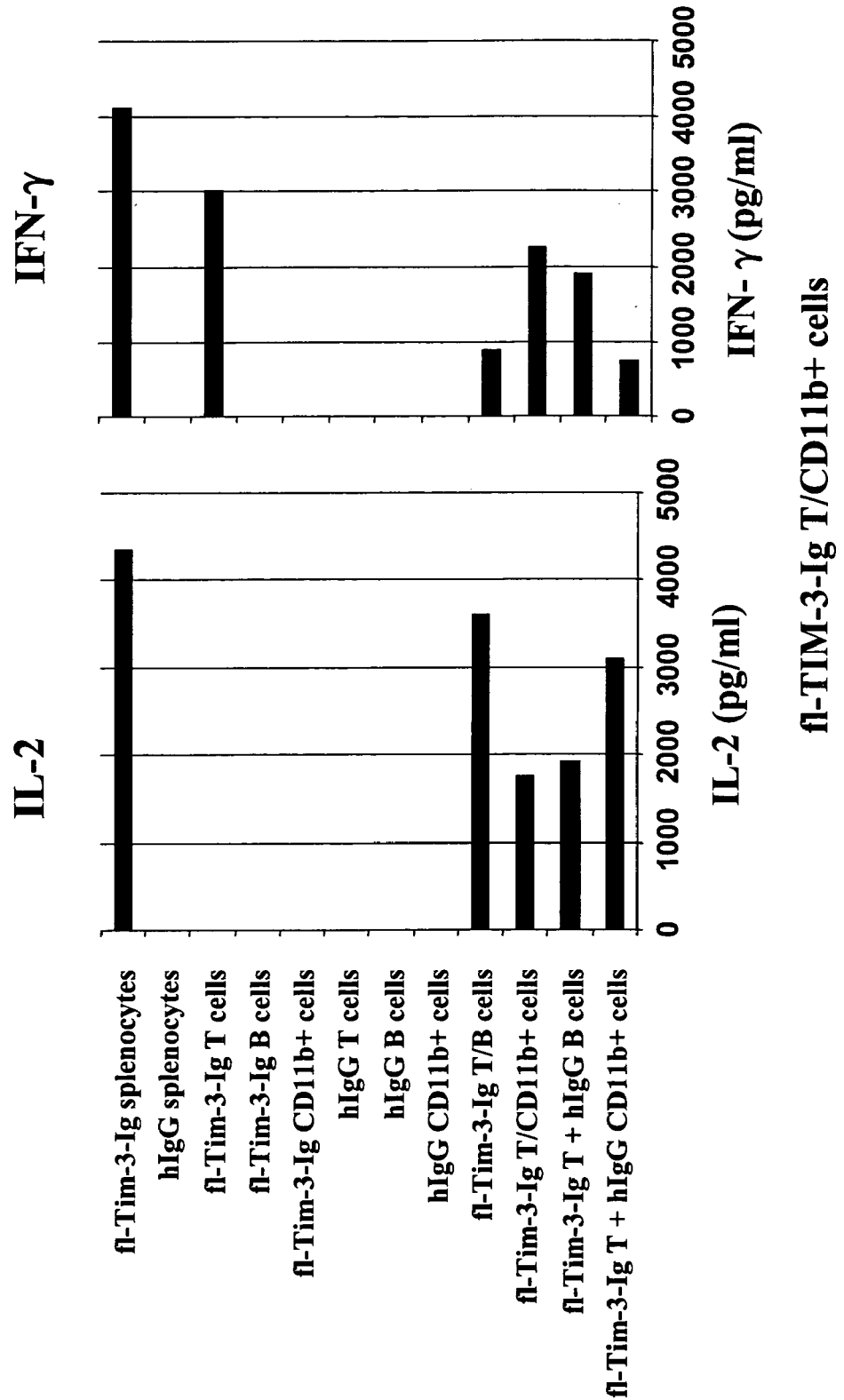

To determine the cytokine secretion patterns of these individual cell populations, supernatants were taken at 48 h and analyzed for IL-2, IL-4, IL-10, TNF-α and IFN-γ production by ELISA. While no individual population of cells from ex-Tim-3-Ig-treated mice was found to produce IL-2, CD3$^+$ T cells from mice treated with ex-Tim-3-Ig were responsible for the majority of the IFN-γ production (FIG. 4B). Addition of B220$^+$ B cells or CD11b$^+$ macrophages (from either ex-Tim-3-Ig- or hIgG-treated mice) resulted in the secretion of IL-2 by CD3$^+$ T cells from ex-Tim-3-Ig-treated mice. Conversely, addition of B220$^+$ B cells or CD11b$^+$ macrophages to the CD3$^+$ T cells from ex-Tim-3-Ig-treated mice resulted in a decrease in IFN-γ production from these CD3$^+$ T cells (FIG. 4B). In short, these data demonstrate that hyperproliferating CD3$^+$ T cells from ex-Tim-3-Ig-treated mice produced large amounts of IFN-γ, but required APCs to produce IL-2.

Figure 4C:
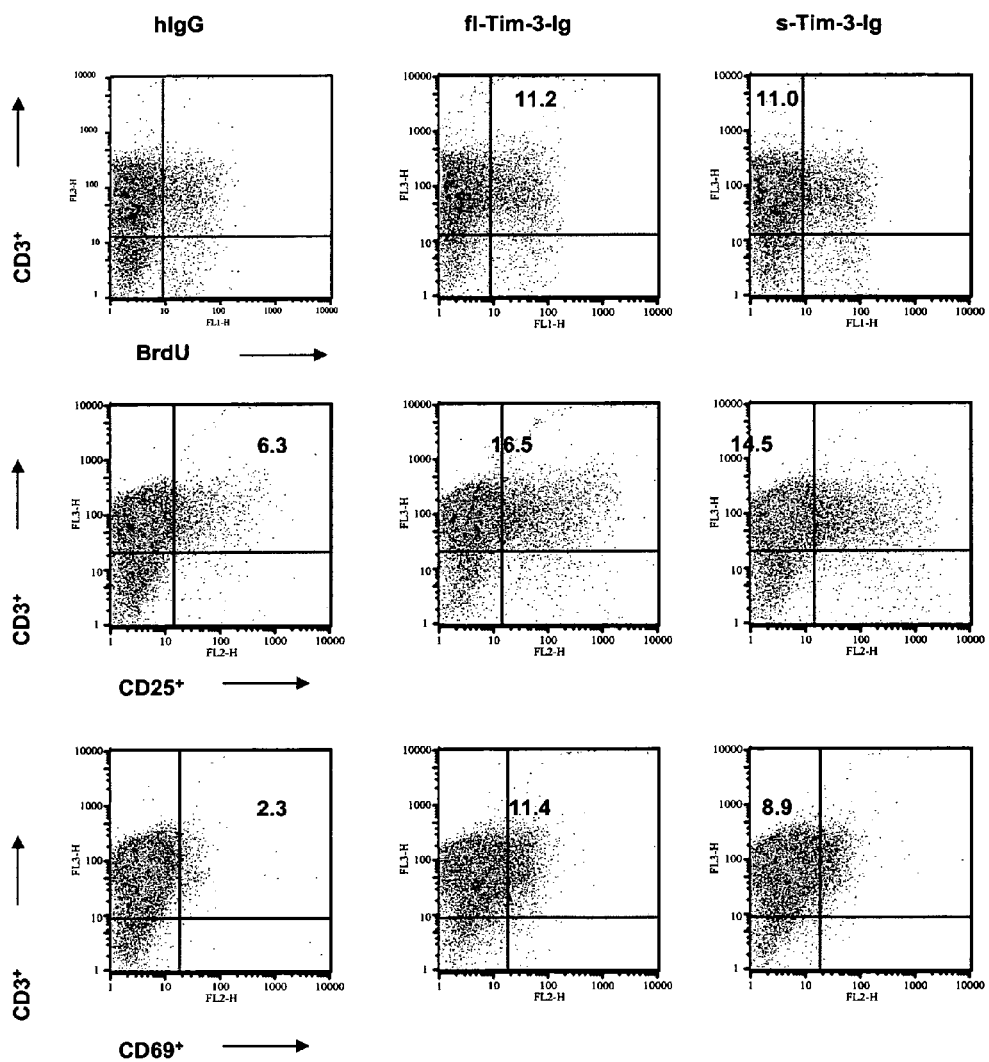

To further characterize the cells that hyperproliferate in response to in vivo treatment with ex-Tim-3-Ig, the phenotype of cells incorporating 5-bromodeoxyuridine (BrdU), a thymidine analog that is incorporated by cycling cells, was determined. The percentage of activated CD3$^+$CD25$^+$ cells was increased 2-3 fold in the Tim-3-Ig-treated groups over the hIgG-treated control group. From this data (FIG. 4C), it was also clear that there was an increased percentage of CD3$^+$ T cells from the Tim-3-Ig-treated mice that incorporated BrdU when compared to hIgG-treated controls. This data was consistent with an increase in the percentage of CD3$^+$CD25$^+$ and CD3$^+$CD69$^+$ cells observed in whole spleen cells from Tim-3-Ig-treated mice as compared to cells from the control hIgG-treated mice. This observation supported the in vitro proliferation and cytokine data (FIG. 4A, 4B), and confirmed that T cells from Tim-3-Ig-treated, immunized mice are highly activated, rapidly proliferating cells (FIG. 4C).

Example 7

Administration of Tim-3-Ig to Mice Abrogates Induction of Tolerance

Since administration of Tim-3-Ig in vivo resulted in hyperactivation of Th1 cells with amplified production of IL-2, Applicants hypothesized that administration of Tim-3-Ig may prevent or abrogate induction of peripheral tolerance. SJL/J mice were tolerized with high dose soluble PLP 139-151 peptide and concurrently immunized with PLP 139-151 emulsified in CFA. This tolerization protocol renders PLP 139-151-specific T cells tolerant to subsequent activation such that cells hypoproliferate and do not produce IL-2(24). To test the effect of ex-Tim-3-Ig on the induction of tolerance, tolerized mice were treated every other day for 8 days with Tim-3-Ig or control PBS or hIgG, and lymph nodes and spleens were taken at day 10 and examined for their in vitro recall response to PLP 139-151 through proliferation and cytokine production.

The induction of tolerance in the draining lymph nodes was examined, in addition to the spleens, since it is in the draining lymph nodes that T cells are induced and first activated. As seen in FIG. 5, lymph node cells from immunized mice tolerized with soluble PLP showed a significant decrease in proliferation to restimulation with PLP 139-151 compared to the control (PBS-tolerized hIgG-treated group). When Tim-3-Ig was co-administered with the tolerogenic dose of PLP 139-151, a significant proliferative response was observed which was comparable to or even greater than that of the control, non-tolerized mice, demonstrating that Tim-3-Ig abrogated or interfered with tolerance induction (FIG. 5). While tolerization with PLP 139-151 resulted in the complete loss of IL-2 and IFN-γ production in the control hIgG-treated group, mice treated with Tim-3-Ig continued to produce Th1 cytokines when restimulated in vitro with cognate antigen (FIG. 5).

The effects of tolerance induction in the spleens of the mice were determined. As shown in FIG. 5A, concurrent in vivo administration of soluble PLP 139-151 in PLP-immunized mice resulted in a dramatic decrease in the proliferative response to PLP 139-151 peptide, confirming the ability of soluble PLP 139-151 to induce T cell tolerance in vivo. Administration of hIgG or PBS together with the soluble PLP 139-151 did not alter tolerance induction (FIG. 6A). However, when ex-Tim-3-Ig was administered together with a tolerogenic dose of PLP 139-151, the proliferation of splenic cells from ex-Tim-3-Ig-treated mice was equivalent to that obtained in splenic cells from non-tolerized control animals (FIG. 6A). Hence, administration of Tim-3-Ig overcomes the induction of or abrogates tolerance, and results in T cell expansion.

Figure 6B:
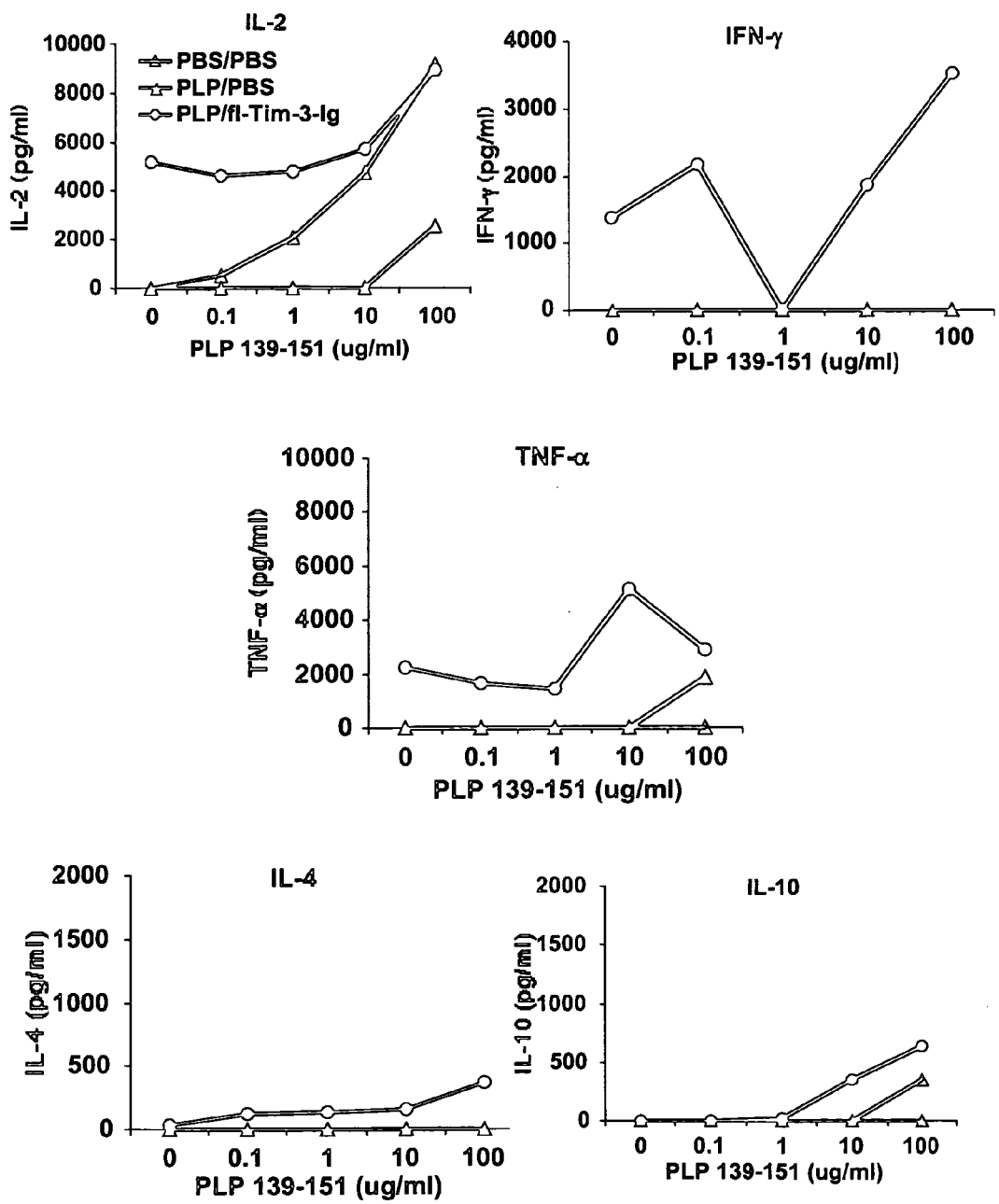
FIG. 6 shows that administration of Tim-3-Ig prevented tolerance induction. (a) SJL/J mice were immunized with PLP 139-151/CFA and concurrently given intraperitoneal injections of 500 μg soluble PLP 139-151 (or PBS as a control vehicle) to induce tolerance. Mice were injected intraperitoneally every other day from day 0-8 with 100 μg ex-Tim-3-Ig, or PBS (100 μl) or hIgG (100 μg) as controls. Mice were sacrificed on day 10, and spleens were taken and cells ($5 \times 10^5$/well) cultured in vitro with increasing concentrations of PLP 139-151 peptide. Proliferation was measured in triplicate wells after 48 h by $^3$H-thymidine incorporation. Mice given control PBS as tolerogen, Δ, PBS; □, hIgG, and ○, ex-Tim-3-Ig treated; mice given PLP as tolerogen, ▲, PBS, ■ hIgG, and ●, ex-Tim-3-Ig treated. Average given for two mice/treatment group. (b) Supernatants were taken from the in vitro cultures described in (a) at 48 h, and cytokine ELISAs for IL-2, IL-4, IL-10, TNF-α and IFN-γ were performed. Symbols as described in (a). Average given for two mice/treatment group.

Since high dose soluble antigen is known to predominantly induce tolerance of Th1 cells and particularly inhibit IL-2 production, Applicants next investigated production of cytokines in the spleens of the tolerized mice. Supernatants were harvested from in vitro cultures at 48 h, and cytokine ELISAs for IL-2, IL-4, IL-10, IFN-γ and TNF-α were performed to determine if spleen cells from tolerized and Tim-3-Ig-treated mice were producing cytokines. As expected, administration of soluble PLP to PLP-immunized mice inhibited IL-2 production (FIG. 6B). Co-administration of ex-Tim-3-Ig resulted in a dramatic increase in IL-2 production, such that IL-2 was produced at lower antigenic concentrations in the ex-Tim-3-Ig treated mice when compared to non-tolerized, PLP-immunized mice (FIG. 6B). Whereas PLP-immunized mice did not show any significant production of IFN-γ or TNF-α, Tim-3-Ig treatment of the tolerized mice resulted in a dramatic production of both IFN-γ and TNF-α from the splenic cultures upon restimulation in vitro (FIG. 6B). Low levels of IL-4 and IL-10 were observed in supernatants from the tolerized, ex-Tim-3-Ig-treated mice only at the highest doses of in vitro restimulation with specific antigen (FIG. 6B).

C. DISCUSSION OF FIRST SERIES OF EXPERIMENTS

The discovery of Tim-3 as a Th1-specific transmembrane protein provided a novel means by which to phenotypically distinguish Th1 from Th2 cells. The functional role of this cell surface protein expressed on fully committed Th1 cells is beginning to be elucidated. Initial studies demonstrated that administration of anti-Tim-3 antibody during the course of an immune response exacerbated the autoimmune disease EAE and resulted in the activation and expansion of macrophages (20). The data presented herein begins to explore the functional in vivo effects of Tim-3/Tim-3-Ligand interaction by use of soluble Tim-3 fusion proteins. Administration of ex-tim-3-Ig or s-Tim-3-Ig fusion proteins in vivo during an ongoing immune response resulted in hyperproliferation of T cells with spontaneous production of Th1 cytokines (IFN-γ and IL-2), even in the absence of antigenic re-stimulation. Furthermore, Tim-3-Ig abrogated or interfered with the induction of tolerance mediated by the administration of high dose soluble antigen.

Flow cytometric analysis of lymphoid cells harvested from naïve mice and stained with Tim-3-Ig revealed that a ligand for Tim-3 is expressed on CD4+ T cells. Furthermore, T cell clones, whether of Th1 or Th2 phenotype, bound Tim-3-Ig. Although a small number of $CD11c^+$ dendritic cells and $CD11b^+$ macrophages also appeared to stain with Tim-3-Ig, $CD4^+$ T cells were the predominant cell type expressing Tim-3-Ligand. This data was superficially surprising since our initial observations regarding Tim-3 showed that treatment of immunized SJL/J mice with anti-Tim-3 antibody increased basal proliferation of whole spleen cells via a cell-to-cell interaction between macrophages and Th1 cells(20). This suggested that the ligand for Tim-3 was potentially expressed on macrophages and that anti-Tim-3 antibody either co-capped Tim-3 on Th1 cells to activate macrophages via its ligand, or blocked a negative signal that resulted in macrophage activation. One possible explanation is that a small but potentially critical population of macrophages that may bear a ligand for Tim-3 were activated in this manner by the antibody administration. An alternate possibility is that the macrophage activation seen upon anti-Tim-3 antibody treatment in vivo may be a secondary consequence of disturbing the interaction of Tim-3 with the Tim-3-Ligand expressed on other T cells(25).

Knowing that Tim-3 is expressed on terminally differentiated Th1 cells and that a potential Tim-3-Ligand is expressed on $CD4^+$ T cells raises the question of how these partners interact in vivo. There are at least two potential mechanisms whereby the Tim-3 fusion proteins might interact with the Tim-3-Ligand in vivo. First, Tim-3-Ig may bind to $CD4^+$ T cells in vivo during the course of immunization and signal through this ligand. This signal may preferentially differentiate naïve $CD4^+$ T cells into Th1 cells or increase the activation state of these $CD4^+$ T cells. Given the Th1 environment created by immunization with PLP 139-151 in CFA, these activated cells may preferentially polarize to the Th1 phenotype, thus accounting for the significantly increased T cell proliferation and production of the Th1 cytokines IFN-γ and IL-2. However, direct cross-linking of Tim-3-Ligand on T cells, with or without CD3-crosslinking by plate-bound antibody, does not induce hyperproliferation of Th1 cells or production of Th1 cytokines. This suggests that activation may not in fact occur through Tim-3-Ig ligation of Tim-3-Ligand, or may uniquely occur in vivo under Th1-polarizing conditions. A second possibility is that Tim-3-Ig may bind the Tim-3-Ligand on ligand-bearing cells (T cells, macrophages and/or dendritic cells), thus blocking its ability to interact with Tim-3 on polarized Th1 cells. If the normal physiological function of the interaction between Tim-3 and Tim-3-Ligand is to downregulate the Th1 response, blocking the ligand by administration of Tim-3-Ig could account for the increased Th1 cell proliferation and Th1 cytokine production observed.

The data presented herein and that of the second experimental series favors the hypothesis that the interaction of Tim-3 with its ligand may be an inhibitory one and that Tim-3-Ig administration blocks this negative interaction, resulting in the expansion of Th1 cells. This possible mechanism is further supported by the data that administration of Tim-3-Ig abrogated induction of peripheral tolerance, suggesting that the physiological interaction between Tim-3 and Tim-3-Ligand may serve to limit expansion of Th1 cells and contribute to induction of tolerance in effector Th1 cells. There are at least two possible mechanisms whereby Tim-3-Ig may abrogate tolerance induction. Tim-3-Ig may hyperactivate effector Th1 cells, and IL-2 thus produced may prevent induction of anergy by high dose soluble antigen. However, another possibility is that Tim-3-Ig may induce proliferation and effector functions in non-tolerized T cells that normally may not proliferate (due to low affinity TCR/MHC-peptide interaction) such that the net result is T cell expansion rather than nonresponsiveness. It is known that high dose tolerance often tolerizes Th1 cells while sparing or expanding Th2 cells(26). As administration of Tim-3-Ig abrogates this tolerance induction in Th1 cells, Th2 cells may remain unaffected, leading to the production of Th2 cytokines IL-4 and IL-10 observed upon restimulation of spleen cells in vitro (FIG. 5B).

Our results suggest that the Tim-3/Tim-3-Ligand pathway may be important for tolerance induction. Interestingly, it has also been shown that CTLA-4 is required for tolerance induction (27). Given the importance of Tim-3 and Tim-3-Ligand in tolerance induction, it is possible that the Tim-3/Tim-3-Ligand pathway may be functioning as a negative regulator of immune responses in a manner similar to CTLA-4, but specifically for effector Th1 cell.

The discovery of a soluble, Ig domain-only form of Tim-3 raised the issue of the role of soluble Tim-3 in the regulation of Th1 responses. This soluble splice variant of Tim-3 is similar to other immunoregulatory/inhibitory receptors that are made as soluble molecules by T cells (e.g. CTLA-4), and these soluble alternatively spliced forms of the receptors have been shown to play an important role in susceptibility and resistance to autoimmune disease (23). It is not, however, clear at this stage when s-Tim-3 is made during Th1 cell differentiation and what its function might be. If, as the present data suggests, the Tim-3/Tim-3-Ligand interaction is an inhibitory one, production of s-Tim-3 may act to block this inhibitory effect, and promote expansion and differentiation of Th1 cells. This could occur if binding of s-Tim-3 to Tim-3-Ligand competes with the inhibitory binding of membrane-bound ex-tim-3 to Tim-3-Ligand. This competition could diminish or prevent the ligation of ex-Tim-3 to Tim-3-Ligand, and subsequently decrease or abrogate downregulation of the Th1 response. Potential regulation of the production of ex-Tim-3 versus s-Tim-3 at the mRNA and protein levels could offer a dynamic means of regulating the immune function of effector Th1 cells.

Since s-Tim-3 contains only the IgV domain but lacks the mucin domain, this data further suggests that the majority of Tim-3's immunoregulatory activity may be mediated by its Ig domain. Preliminary data suggests that s-Tim-3-Ig shows high affinity/avidity binding to $CD4^+$ T cells and also mediates stronger immunoregulatory effects in vivo. It has previously been shown that members of the picornavirus family (such as poliovirus and rhinoviruses) and human immunodeficiency virus (HIV) preferentially bind to the Ig domain of receptors rather than subsequent functional domains(28-31). Furthermore, havcr-1, the receptor for picornavirus family member hepatitis A virus (HAV), has been shown to bind HAV through the N-terminal cysteine (Cys)-rich region of havcr-1 (which is part of the Ig domain of the receptor)(28, 29). Given that havcr-1 is the human homolog of murine Tim-1(19), a member of the Tim gene family, it stands to reason that Tim-3 may interact with its ligand in a similar manner, through its Ig domain.

The potential functional role(s) of the mucin domain that is part of the full-length membrane-anchored form of Tim-3 are uncertain. It has been postulated that the Threonine/Serine/Proline (TSP)-rich mucin-like region of havcr-1 may serve to extend the Cys-rich region above the cell surface to facilitate binding to HAV(28,32). The mucin domain of Tim-3 may function in a similar structural rather than functional binding manner. Another possibility is that the mucin domain of Tim-3 may present carbohydrate moieties that can interact with selectins, and thus facilitate the trafficking of effector Th1 cells. A role such as this in facilitating lymphocyte homing has been postulated for the mucin region of the structurally similar multi-domain receptor MAdCAM-1(33).

Taken together, these data suggest that Tim-3 interaction with its ligand may represent an inhibitory pathway which regulates expansion and function of Th1 cells during normal T cell immune responses. This pathway may also play a crucial role in regulating peripheral tolerance of effector Th1 cells.

D. REFERENCES

1. Mosmann, T., Cherwinski, H., Bond, M., Giedlin, M. & Coffman, R. Two types of murine helper T cell clone. I. Definition according to profiles of lymphokine activities and secreted proteins. J Immunol 136, 2348-2357 (1986).
2. Mosmann, T. & Sad, S. The expanding universe of T-cell subsets: Th1, Th2 and more. Immunol Today 19, 138-146 (1996).
3. Abbas, A., Murphy, K. & Sher, A. Functional diversity of helper T lymphocytes. Nature 383, 787-793 (1996).
4. Sher, A. & Coffman, R. Regulation of immunity to parasites by T cells and T cell-derived cytokines. Annu Rev Immunol. 10, 385-409 (1992).
5. Liblau, R., Singer, S. & McDevitt, H. Th1 and Th2 CD4+ T cells in the pathogenesis of organ-specific autoimmune diseases. Immunol Today 16, 34-38 (1995).
6. Nicholson, L., Greer, J., Sobel, R., Lees, M. & Kuchroo, V. An altered peptide ligand mediates immune deviation and prevents autoimmune encephalomyelitis. Immunity 3, 397-405 (1995).
7. Kuchroo, V. et al. B7-1 and B7-2 costimulatory molecules activate differentially the Th1/Th2 developmental pathways: application to autoimmune disease therapy. Cell 80, 707-718 (1995).
8. Lack, G. et al. Nebulized but not parenteral IFN-gamma decreases IgE production and normalizes airways function in a murine model of allergen sensitization. J Immunol 152, 2546-2554 (1994).
9. Hofstra, C. et al. Prevention of Th2-like cell responses by coadministration of IL-12 and IL-18 is associated with inhibition of antigen-induced airway hyperresponsiveness, eosinophilia, and serum IgE levels. J Immunol 161, 5054-5060 (1998).
10. Syrbe, U., Siveke, J. & Hamann, A. Th1/Th2 subsets: distinct differences in homing and chemokine receptor expression? Springer Semin Immunopathol 21, 263-285 (1999).
11. Loetscher, P. et al. CCR5 is characteristic of Th1 lymphocytes. Nature 391, 344-345 (1998).
12. Bonecchi, R. et al. Differential expression of chemokine receptors and chemotactic responsiveness of type 1 T helper cells (Th1s) and Th2s. J Exp Med 187, 129-134 (1998).
13. Sallusto, F., Lenig, D., Mackay, C. & Lanzavecchia, A. Flexible programs of chemokine receptor expression on human polarized T helper 1 and 2 lymphocytes. J Exp Med 187, 875-883 (1998).
14. Venkataraman, C., Schaefer, G. & Schindler, U. Cutting edge: Chandra, a novel four-transmembrane domain protein differentially expressed in helper type 1 lymphocytes. J Immunol 165, 632-636 (2000).
15. Jourdan, P. et al. IL-4 induces functional cell-surface expression of CXCR4 on human T cells. J Immunol 160, 4153-4157 (1998).
16. Lohning, M. et al. T1/ST2 is preferentially expressed on murine Th2 cells, independent of interleukin 4, interleukin 5, and interleukin 10, and important for Th2 effector function. Proc Natl Acad Sci USA 95, 6930-6935 (1998).
17. McAdam, A. et al. Mouse inducible costimulatory molecule (ICOS) expression is enhanced by CD28 costimulation and regulates differentiation of CD4+ T cells. J Immunol 165, 5035-5040 (2000).
18. Zingoni, A. et al. The chemokine receptor CCR8 is preferentially expressed in Th2 but not Th1 cells. J Immunol 161, 547-551 (1998).
19. McIntire, J. et al. Identification of Tapr (an airway hyperreactivity regulatory locus) and the linked Tim gene family. Nat Immunol 2, 1109-1116 (2001).
20. Monney, L. et al. Th1-specific cell surface protein Tim-3 regulates macrophage activation and severity of an autoimmune disease. Nature 415, 536-541 (2002).
21. Zheng, X. et al. Administration of noncytolytic IL-10/Fc in murine models of lipopolysaccharide-induced septic shock and allogeneic islet transplantation. J Immunol 154, 5590-5600 (1995).
22. Sanchez-Fueyo, A. et al. The Ig superfamily member Tim-3 inhibits Th1-mediated auto- and allo-immune response and promotes immunological tolerance. (submitted).
23. Ueda, H. et al. Association of the T-cell regulatory gene CTLA4 with susceptibility to autoimmune disease. Nature 423, 506-511 (2003).

24. Perez, V. et al. Induction of peripheral T cell tolerance in vivo requires CTLA-4 engagement. Immunity 6, 411-417 (1997).
25. Kuchroo, V., Umetsu, D., DeKruyff, R. & Freeman, G. The TIM gene family: emerging roles in immunity and disease. Nat Rev Immunol 3, 454-462 (2003).
26. Burstein, H. & Abbas, A. In vivo role of interleukin 4 in T cell tolerance induced by aqueous protein antigen. J Exp Med 177, 457-463 (1993).
27. Greenwald, R., Boussiotis, V., Lorsbach, R., Abbas, A. & Sharpe, A. CTLA-4 regulates induction of anergy in vivo. Immunity 14, 145-155 (2001).
28. Thompson, P., Lu, J. & Kaplan, G. The Cys-rich region of hepatitis A virus cellular receptor 1 is required for binding of hepatitis A virus and protective monoclonal antibody 190/4. J Virol 72, 3751-3761 (1998).
29. Silberstein, E., Dveksler, G. & Kaplan, G. Neutralization of hepatitis A virus (HAV) by an immunoadhesin containing the cysteine-rich region of HAV cellular receptor-1. J Virol 75, 717-725 (2001).
30. Xing, L. et al. Distinct cellular receptor interactions in poliovirus and rhinoviruses. EMBO J. 19, 1207-1216 (2000).
31. Kaplan, G. et al. Identification of a surface glycoprotein on African green monkey kidney cells as a receptor for hepatitis A virus. EMBO J 15, 4282-4296 (1996).
32. Jentoft, N. Why are proteins O-glycosylated? Trends Biochem Sci 15, 291-294 (1990).
33. Briskin, M., McEvoy, L. & Butcher, E. MAdCAM-1 has homology to immunoglobulin and mucin-like adhesion receptors and to IgA1. Nature 363, 461-464 (1993).
34. Kovac, Z. & Schwartz, R. The molecular basis of the requirement for antigen processing of pigeon cytochrome c prior to T cell activation. J Immunol 134, 3233-3240 (1985).
35. Matis, L. et al. Clonal analysis of the major histocompatibility complex restriction and the fine specificity of antigen recognition in the T cell proliferative response to cytochrome C. J Immunol 130, 1527-1535 (1983).
36. Nicholson, L., Murtaza, A., Hafler, B., Sette, A. & Kuchroo, V. A T cell receptor antagonist peptide induces T cells that mediate bystander suppression and prevent autoimmune encephalomyelitis induced with multiple myelin antigens. Proc Natl Acad Sci USA 94, 9279-9284 (1997).

Second Series of Experiments

A. INTRODUCTION

Differentiation and clonal expansion of T helper (Th) precursor cells into T effector populations plays an important role in the adaptive immune response and provides protection against intracellular viruses and pathogenic bacteria. However, unrestrained activation of Th effector cells has also been shown to underlie a number of inflammatory disorders. In this context, Th1 effector cells are implicated in the pathogenesis of rheumatoid arthritis, inflammatory bowel disease (IBD), and other autoimmune disorders including type I diabetes and multiple sclerosis(1,2), as well as allograft rejection(3,4). In contrast, Th2 cell activation plays a critical role in the pathogenesis of allergic asthma(5) and has been linked to the acquisition of transplant tolerance(3,4). The extent of T cell activation and mode of differentiation is largely determined by the duration and strength of T cell receptor (TCR) mediated stimulation(6). In addition, a number of costimulatory and accessory molecules, including TNF receptor(7) and immunoglobulin (Ig) superfamily members(8), as well as cytokines such as IL-2, regulate the extent of clonal expansion, deletion, and/or anergy induction(9). However, while Applicants appreciate many of the cellular and molecular mechanisms that regulate the activation of naïve T cells, the molecules that determine the fate of effector T cell subpopulations remain to be elucidated.

The Ig superfamily member TIM-3 (T cell Immunoglobulin domain, Mucin domain) was initially described by Monney et al. (10) as a transmembrane protein preferentially expressed on differentiated Th1 cells. In a model of experimental allergic encephalomyelitis (EAE), a Th1-mediated autoimmune disease, in vivo administration of anti-TIM-3 monoclonal antibody (mAb) led to more severe inflammatory events within the brain and more severe clinical disease. Based on these observations, TIM-3 was proposed as a negative regulator of tissue destructive immune responses in EAE (10). However, it remained uncertain whether these data reflected inhibition of a negative signal provided by TIM-3 or, conversely, whether TIM-3 crosslinking in vivo with the mAb exerted a positive signal to induce T cell activation and disease exacerbation. Based on results reported herein, Applicants conclude that TIM-3 engagement by its putative ligand provides an inhibitory signal to dampen inflammatory responses in vivo. TIM-3 pathway blockade via TIM-3-Ig fusion protein treatment accelerates diabetes onset in the NOD (non obese diabetic) model, and abolishes the capacity of both CTLA4 and combined donor specific transfusion (DST) plus anti-CD154 (CD40L) treatment, potent, costimulatory blockade-based, tolerance-promoting protocols in transplantation(11-13), to induce tolerance to MHC-mismatched allografts. While the precise mechanisms involved remain to be fully elucidated, Applicants propose that TIM-3 regulates the outcome of auto- and allo-immune responses at least in part by modulating the capacity of regulatory T cells to dampen inflammatory responses.

B. METHODOLOGY

Mice

All mice were obtained from The Jackson Laboratories (Bar Harbor, Me.) and maintained under specific pathogen free conditions in conventional animal facilities at Millennium Pharmaceuticals, Inc. (Cambridge, Mass., USA), Beth Israel Deaconess Medical Center (Boston, Mass., USA), or DRFZ (Berlin, Germany) according to the relevant institutional and state guidelines.

Identification and Cloning of Murine TIM-3

A Th1-specific library was generated using the Clontech PCR-Select cDNA Subtraction Kit (Clontech, Palo Alto, Calif.). RNA from activated Th1 clones were used as "tester" and RNA from activated Th2 clones used as "driver." Plasmid DNAs from individual clones were spotted onto nylon filters and hybridization performed with single stranded probes from Th1 and Th2 RNA. One of the clones in the Th1 library consisted of an 857-bp cDNA and was used to obtain the full-length clone using a cDNA library from murine Th1 cells. The human homologue was subsequently identified and sequenced from a human spleen cDNA library. Murine antigen specific Th1 (AE7 and Dorris) and Th2 (D10.G4, DAX, CDC25) clones were stimulated every 10-14 days with peptide, mitomycin C treated APCs, and IL-2 (100 U/ml). Cells were activated with anti-CD3 mAb (2C11, Pharmingen) and RNA isolated. Differential expression of TIM-3 cDNA was subsequently confirmed by Northern Blot from resting and anti-CD3 activated clones.

Generation of TIM-3 mAb and TIM-3 Fusion Proteins

A DNA sequence containing the extracellular domain of TIM-3 was PCR-amplified and cloned into a vector containing the CD5 signal sequence and the human IgG1 constant region. COS cells were transfected and the recombinant protein purified over a protein A column. Wky rats were immunized with purified murine TIM-3 fusion protein (100 μg) in CFA and boosted i.p. and subcutaneously. Splenocytes were fused with SP/2 myeloma cells and the resulting clones screened for binding on TIM-3-transfected CHO cells. One of these clones, 8H7, was selected based on specific binding to TIM-3, but not ICOS transfectants. Anti-TIM-3 8H7 mAb was isotyped as a rat IgG1 using specific antibodies (BD Pharmingen, San Diego, Calif.). ex-Tim-3-Ig and s-TIM-3-Ig were constructed as human IgG1 Fc tail fusion proteins and expressed in NS.1 cells as described in the first experimental series. Biotinylated TIM-3 related fusion proteins or human IgG1 together with fluorochrome-conjugated streptavidin (BD PharMingen) were used for TIM-3L staining experiments.

Islet Transplantation

Islet transplantation was performed as previously described(51). Approximately 700 DBA/2 (H-$2^d$) islets were transplanted under the renal capsule of streptozotocin-induced diabetic C57BL/6 (H-$2^b$). Allograft function was monitored by serial blood glucose measurements. The tolerizing protocol employed consisted in the i.v. administration of $10^7$ DBA/2 splenocytes 28 days before transplantation (day-28), and 250 μg of a hamster mAb anti-mouse CD154 (MR1, IgG2a, ATCC HB11048, American Type Culture Collection, Rockville, Md.) i.p. on days −28, −26, −24. ex-Tim-3-Ig control hIgG1 were administered i.p at a dose of 250 μg on days −28, −26, −24. In selected recipients, 200 μg of rat anti-mouse CD25 mAb (PC61, 5.3, IgG1, ATCC TB222) was also administered i.p. on days −40, −38 and −36. Applicants have previously determined that anti-CD25 mAb administered at such doses eliminates more than 80% of CD4+ CD25+ T cells in both secondary lymphoid organs and peripheral blood. In some experiments tolerance was induced by administering 0.1 μg CTLA4Ig on days 0, 2, 4, 6, 8 after transplantation.

Real-Time PCR Experiments

Total RNA was extracted from islet grafts with trizol and reverse transcription performed using Multiscribed Reverse Transcriptase Enzyme (PE Applied Biosystems, Foster City, Calif.). Real-time PCR was performed with the ABI 7700 sequence detector system (PE Applied Biosystems). To quantify the levels of mRNA, the expression of the target genes was normalized to the housekeeping gene GAPDH, and data were expressed as relative fold difference between cDNA of the study samples and a calibrated sample. TIM-3 primer/probe sequences are as follows: probe, 5'-ACAGCTGCCT-GCCCAGTGCCC-3'; forward primer, 5'-GCCGGTGGAC-CTCAGTTTC-3'; reverse primer, 5'-TGGGAGCCAGCACAGATCA-3'. GAPDH, IFN-γ, IL-4 and IL-10 primer/probe sets were purchased from Applied Biosystems.

Adoptive Cell Transfer into Skin Allograft Recipients

Single cell suspensions of lymph node cells were obtained from naïve C3H/He mice (H-$2^k$), or from C3H/He mice treated with an i.v. injection of $10^7$ DBA/2 splenocytes (28 days before; −28), and either anti-CD154 (250 μg on days −28, −26 and −24) or anti-CD154 plus ex-Tim3-Ig (250 μg each on days −28, −26 and −24). Cells were stained with fluorochrome-conjugated anti-CD25 and anti-CD4 (all from BD PharMingen) and sorted on a MoFlo® High-Performance Cell Sorter (Cytomation; Fort Collins, Colo.). Purity of CD4+ CD25− and CD4+CD25+ preparations was consistently >90%. Varying numbers of CD4+CD25+ T regs and CD4+ CD25− effector T cells were injected into the tail vein of C3H/He Scid mice hosts undergoing allogeneic DBA/2 skin transplantation 24 hours later. In some experiments, 3 doses of 250 μg ex-Tim-3-Ig were administered on days 0, 2 and 4 after skin transplant. Full-thickness DBA/2 tail skin allografts were performed as previously described(52), and graft survival was monitored daily. Rejection was defined as a complete necrosis of the skin grafts. Similar experiments were performed using wild type C57BL/6 mice as donors of T cell populations, and C57BL/6Rag$^{-/-}$ as recipients of DBA/2 skin allografts.

In Vitro Proliferation Assays

To assess the proliferation of CD4+ T cell subpopulations CD4+CD25+ and CD4+CD25− T cells were sorted as previously described and cultured in round-bottom 96-well microtiter plates at a cell density of $5\times10^5$/mL together with 2 μg/mL anti-CD3 mAb, 5 μg/mL anti-CD28 mAb and 100 U/mL of rIL-2 (all from PharMingen). Cells were harvested and stained with biotinylated s-TIM-3-Ig or control human IgG1 followed by streptavidin-CyChrome at 24 and 48 hours and analyzed by flow cytometry.

C. EXAMPLES OF SECOND SERIES OF EXPERIMENTS

Example 11

A TIM-3 Ligand is Expressed on CD4+ T Cells

The structure of TIM-3 is somewhat reminiscent of mucosal addressin cell adhesion molecule-1 (MAdCam-1), which contains two Ig domains and a mucin rich region (10). In order to assess the distribution of putative TIM-3 ligand(s) (TIM-3L), human IgG1-derived Fc fusion proteins incorporating the extracellular domain of murine TIM-3 (full-length or ex-Tim-3-Ig), or a truncated, soluble, Ig domain only (s-TIM-3-Ig)(16) were generated. Both ex-Tim-3-Ig and s-TIM-3-Ig bound to resting CD4+ T cells, but not CD8+, B220+ or CD11b+ cells (FIG. 8C), with s-TIM-3-Ig binding more intensely. Some binding was also noted on splenic CD11c+ dendritic cells (FIG. 7A), but the pattern of staining was far less consistent than that observed for CD4+ T cells. Based on the amplified staining pattern observed with s-TIM-3-Ig, as compared to ex-Tim-3-Ig, the Ig domain of TIM-3 appears to be responsible for interactions with TIM-3L.

Example 12

Figure 7:
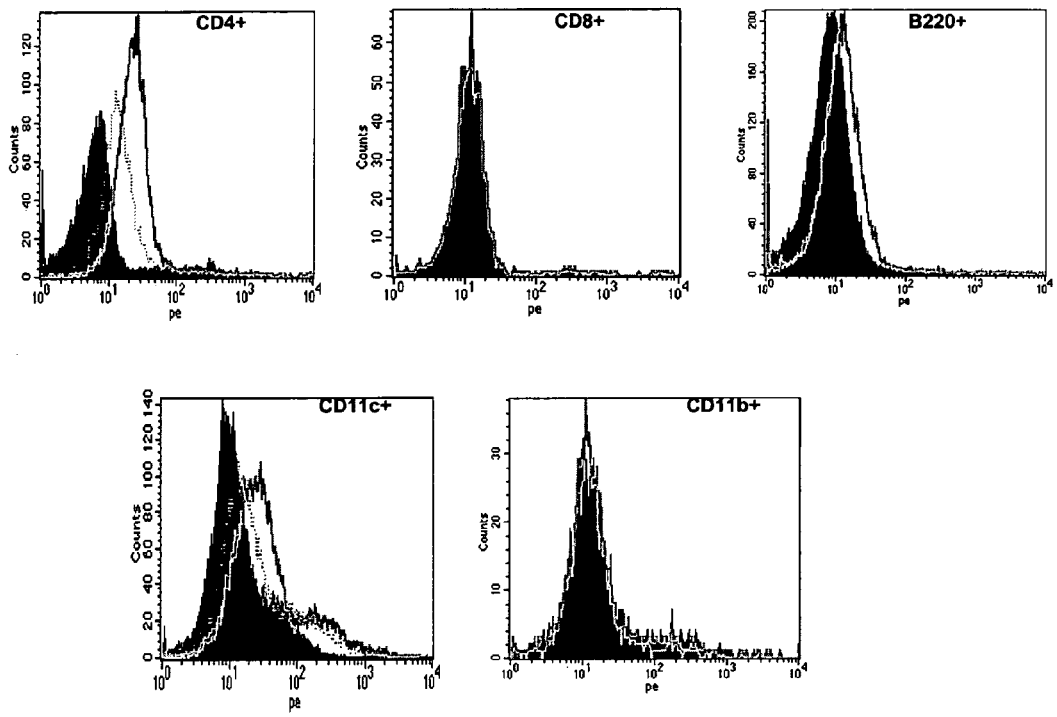
FIG. 7 shows the expression of TIM-3 and TIM-3L. (a) ex-Tim-3-Ig and, more significantly, the truncated s-TIM-3-Ig fusion protein bind to resting CD4+ T cells and a portion of CD11c+ but not CD11b+, B220+ or CD8+ T cells. Isotype control staining is shown in closed histograms; open histograms show binding with ex-TIM-3-Fc (dotted line) and s-TIM-3-Ig (solid line). (b) CD4+CD25−, but not regulatory CD4+ C25+, T cells, downregulate TIM-3L after in vitro stimulation. Both CD4+CD25− and CD4+CD25+ T cells bind s-TIM-3-Ig in resting condition (upper panel). While no changes in the expression of TIM-3L are observed after 24 hours of in vitro stimulation with anti-CD3, anti-CD28 and rIL-2 (middle panel), at 48 hours TIM-3L is only detected on CD4+CD25+ T cells. Isotype control staining is shown in closed histograms; open histograms show binding with s-TIM-3-Ig. Data shown in this figure are representative of 3 independent experiments.
Figure 7:
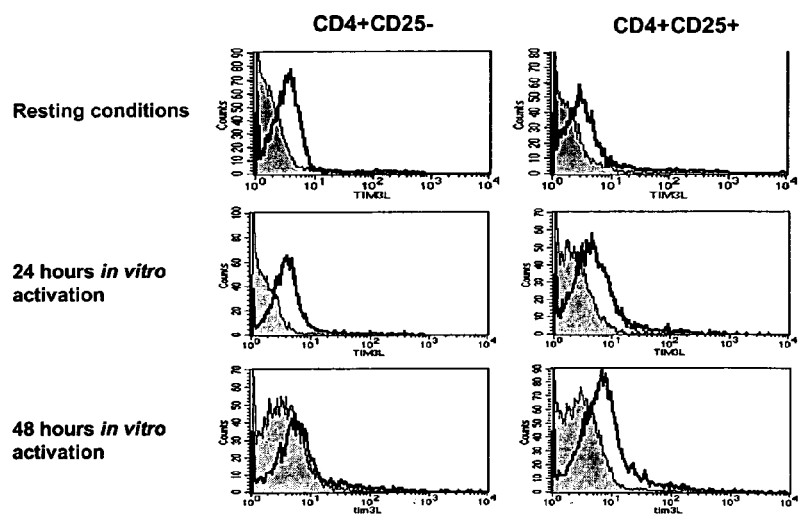

CD4+CD25− T cells, but not CD4+CD25+ regulatory T Cells, Downregulate TIM-3L Expression After Activation In resting conditions, TIM-3 related fusion proteins bind similarly to both effector CD4+CD25− and regulatory CD4+ CD25+ T cell subpopulations (FIG. 7B, upper panel). In order to identify potential mechanisms through which TIM-3 might selectively target the function of either regulatory or effector CD4+ T cells, the kinetics of TIM-3L expression, assessed by the binding of s-TIM-3-Ig, on CD4+CD25− and CD4+ CD25+ T cells after activation in vitro was studied. Stimulation with anti-CD3 and anti-CD28 mAbs did not alter TIM-3L expression throughout the first 24 hours of culture (FIG. 7B, middle panel). In contrast, TIM-3L expression was downregulated upon activated CD4+CD25− T cells at 48 hours of culture, while TIM-3L expression persisted upon CD4+

CD25+ regulatory T cells (FIG. 7B lower panel). Downregulation of TIM-3L expression on CD4+CD25− T cells was also observed upon in vitro activation with Concanavalin A or LPS. The preferential expression of the putative TIM-3L on activated regulatory T cells is mirrored by the expression of TIM-3 on activated Th1 cells. Hence, Applicants have investigated the hypothesis that TIM-3/TIM-3L interactions are crucial to the acquisition and/or maintenance of immunoregulation and tolerance in Th1-mediated immune responses.

Example 16

TIM-3 Pathway Blockade Prevents Acquisition of Tolerance in Allograft Models

While transplantation tolerance can be achieved in both Th1 and Th2 polarized conditions(4,25,26), Th1 to Th2 immunodeviation facilitates the occurrence of tolerance(4, 27). Indeed, the effects of many tolerizing immunosuppressive regimens are associated with immunodeviation into Th2-type allograft response(4). To address the role of Th1-specific TIM-3 cell surface proteins in the acquisition of allograft tolerance, an islet allograft model was utilized in which recipients are treated with the combination of donor specific transfusion (DST) and anti-CD154 (CD40L) mAb to achieve CD40-CD154 costimulatory blockade(11,12,28). In this model, a single dose of DST and anti-CD154 administered 1 month before transplantation ensures the indefinite survival of MHC-mismatched islet allografts. Moreover, treated long-surviving transplant recipients readily accept second grafts from the same donor while rapidly reject third-party strain grafts, indicating that treatment induces donor-specific allograft tolerance(12,28). In contrast, in untreated control recipients an islet-invasive lymphocytic infiltrate can be observed 7 days after transplantation, and most allografts are completely destroyed by day 20 post-transplant (12,28).

Figure 8A:
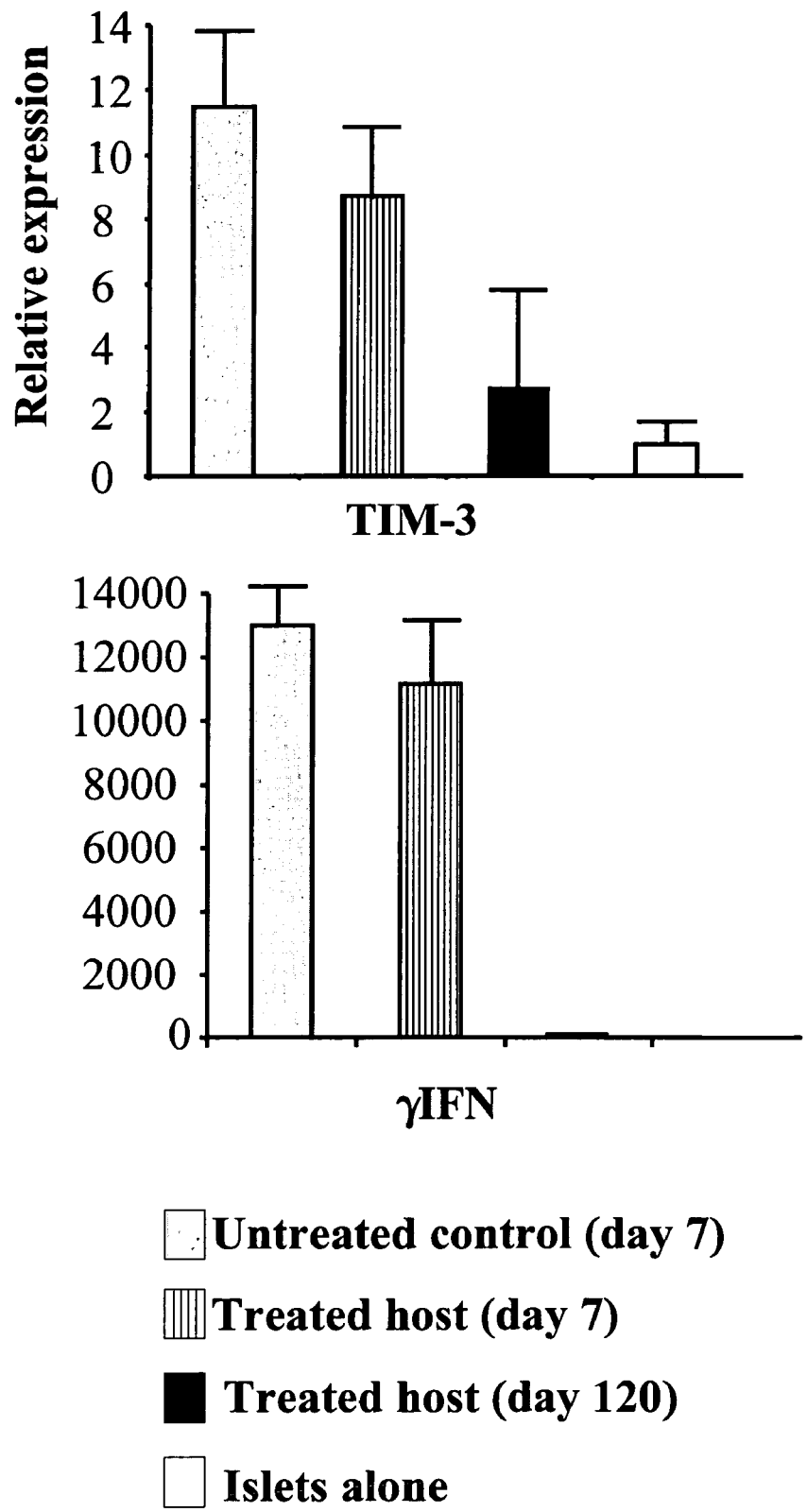
FIG. 8 shows that TIM-3 contributes to the tolerizing effects of DST plus anti-CD154 treatment in an MHC-mismatched islet allograft model. (a) TIM-3 and IFN-γ gene transcripts are upregulated in rejecting but not in long-term surviving islet allografts. Data are expressed as relative fold difference between target samples and a calibrator (isolated islets). Values plotted represent the mean+/−SE obtained from 4 independent experiments. (b) Concurrent administration of ex-Tim-3-Ig together with DST plus anti-CD154 prevents the induction of transplantation tolerance to islet allografts. (c) Administration of ex-Tim-3-Ig significantly decreases the tolerance-promoting capacity of CTLA4Ig.

To determine whether TIM-3 expression is relevant in this model, real-time PCR experiments were performed to compare intragraft gene expression in treated and control recipients. While 7 days after transplantation high intragraft γIFN and TIM-3 gene expression is observed in both treated and control hosts (FIG. 8A), the allograft response in long-surviving tolerant recipients (120 days post-transplant) is characterized by blunted TIM-3 and γIFN intragraft gene expression (FIG. 8A). Intragraft expression of IL-2 is closely associated with that of TIM-3 and γIFN in both treated and untreated hosts at day 7. In contrast, a 2-3 fold increase in the intragraft expression of IL-4 and IL-10 is observed in DST plus anti-CD 154 treated hosts at both day 7 and 120 as compared with rejecting grafts. Thus, treatment is associated with upregulation of Th2-type gene expression, while downregulation of Th1 responses occurs during the maintenance phase (day 120), but not the induction phase (day 7), of transplantation tolerance.

Figure 8B:
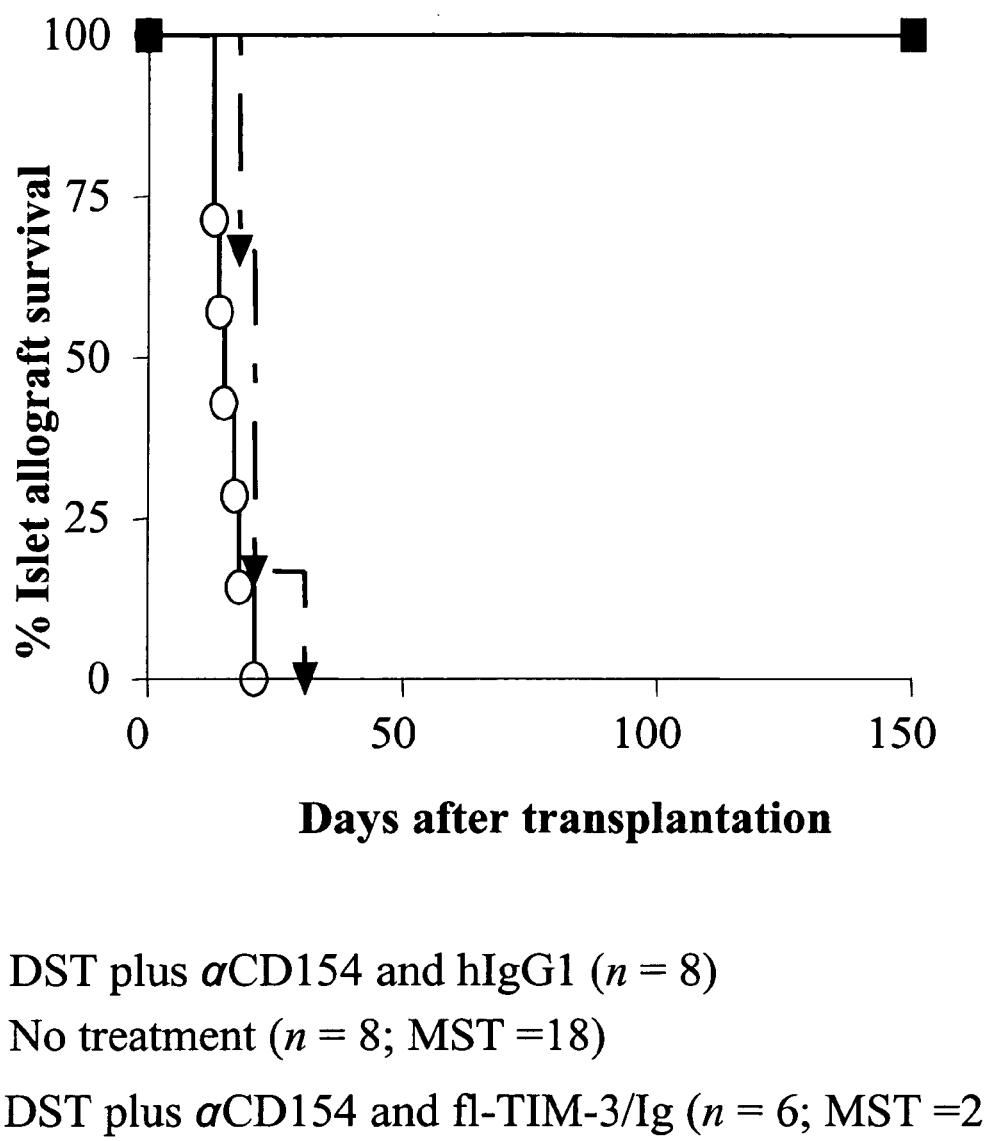

Whether the integrity of the TIM-3 pathway is required for the achievement of transplantation tolerance was next assessed. The administration of ex-Tim-3-Ig together with DST plus anti-CD154 completely prevents the acquisition of islet allograft tolerance and rapidly precipitates rejection (FIG. 8B). In addition, ex-Tim-3-Ig administration also abrogates induction of tolerance mediated by monotherapy with a high dose of anti-CD154.

Figure 8C:
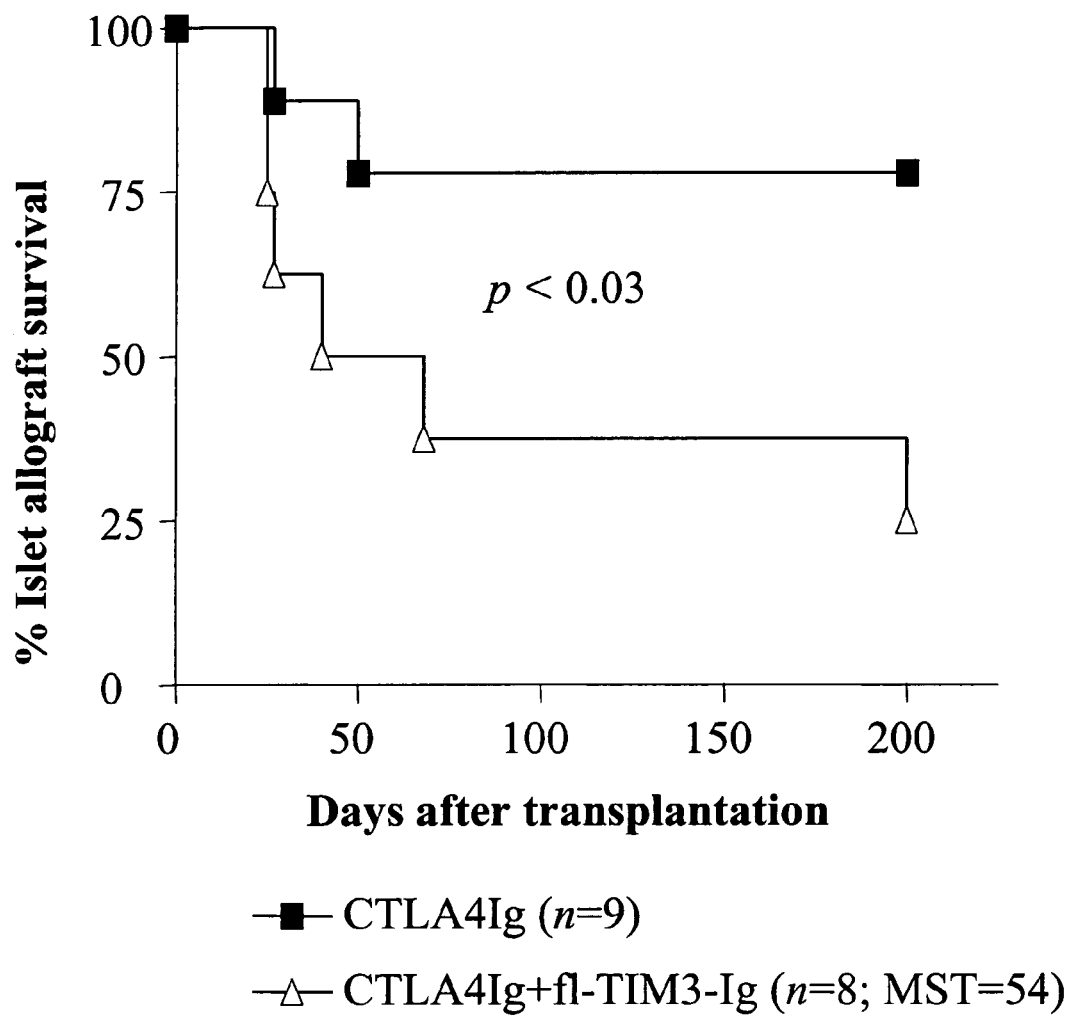

In order to determine whether the TIM-3 pathway is important only in the mechanisms by which tolerance is achieved with anti-CD154+/−DST treatment, the effects of TIM-3 blockade in a transplant model in which tolerance is achieved via CTLA4Ig administration were tested. The mechanisms of action of CTLA4Ig in vivo involve both the inhibition of antigen-reactive T cell proliferation and the induction of immunoregulation and peripheral tolerance (30-32). While CTLA4Ig treatment produced indefinite engraftment of islet allografts in 7 out of 9 treated recipients, co-administration of ex-Tim-3-Ig resulted in the rejection of the majority of the allografts (FIG. 8C). Taken together with the results of the first experimental series, these data clearly indicate that TIM-3 is a critical regulator of immunological tolerance.

Example 16

Figure 9A:
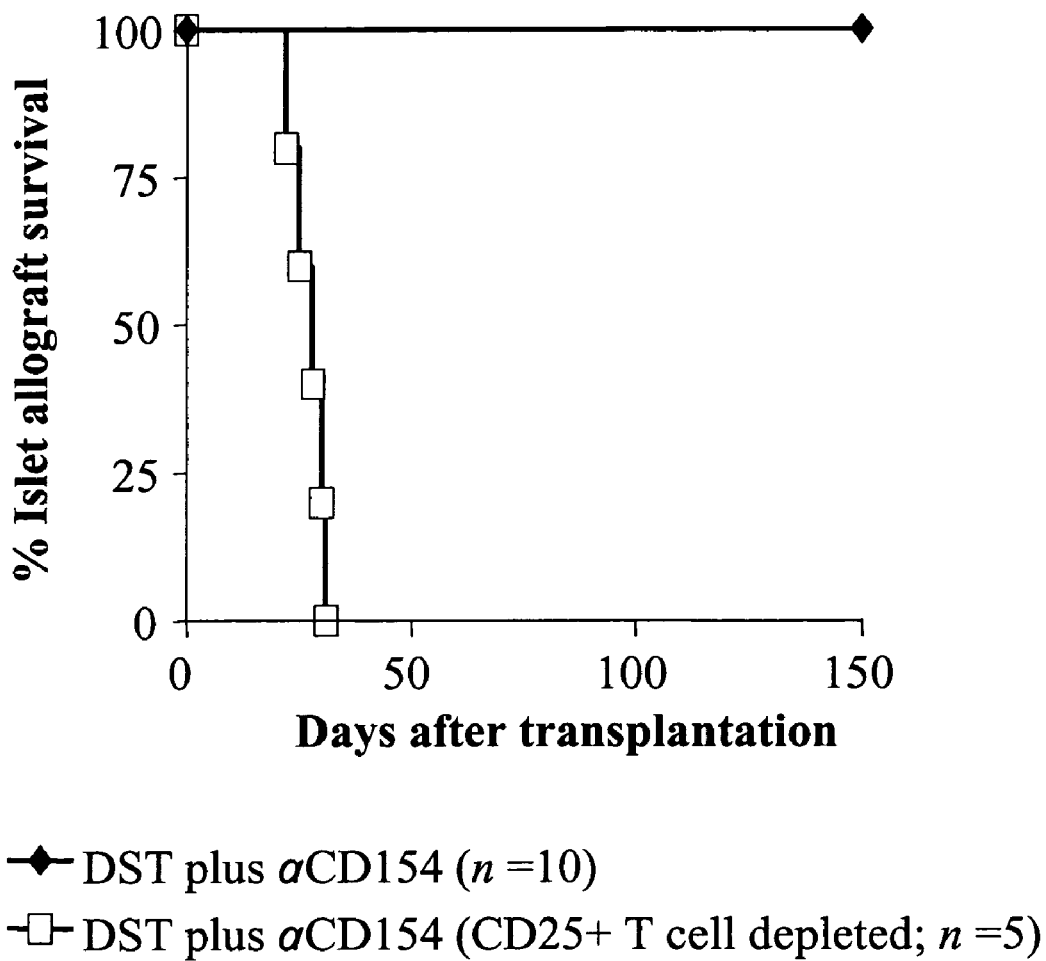
FIG. 9 shows that TIM-3 modulates the alloantigen-specific effects of DST plus anti-CD154 treatment on CD4+CD25+ regulatory T cells. (a) Depletion of CD4+CD25+ T cells before DST plus anti-CD154 administration results in rapid islet allograft rejection. MST=median survival time (days). (b) ex-Tim-3-Ig does not interfere with the capacity of CD4+CD25+ regulatory T cells to suppress CD4+CD25-T cells in an adoptive transfer skin allograft model if administered at the time of transplantation. (c) $1 \times 10^5$ CD4+CD25− T cells from naïve or DST plus anti-CD154 treated mice rapidly induce skin allograft rejection (left hand panel). Both CD4+CD25+ T cells harvested from naïve hosts and CD4+CD25+ T cells obtained from DST plus anti-CD154 treated mice are capable of preventing skin allograft rejection when adoptively transferred at high ratios of regulatory to effector T cells ($4 \times 10^5 : 1 \times 10^5$; middle panel). Only CD4+CD25+ T cells harvested from treated mice exert significant graft-protecting effects when transferred with an equal number of CD4+CD25− T cells ($4 \times 10^5 : 4 \times 10^5$; right hand panel). In the middle and right hand panel CD4+CD25− T cells are derived only from naïve untreated mice. (d) The concurrent administration of ex-Tim-3-Ig together with DST plus anti-CD154 abolishes the enhanced immunosuppressive effects conferred to CD4+CD25+ T cells by DST plus anti-CD154 treatment (the group of naïve CD4+CD25+ T cells is used as baseline for statistical comparisons). MST=median survival time (days).

TIM-3 Blockade Does Not Eliminate the Capacity of naïve CD4+CD25+ Regulatory T Cells to Suppress the Ability of CD4+CD25− T Cells to Reject Allografts Applicants have previously determined that CD4+CD25+ regulatory T cells are critically involved in the maintenance of the tolerant state induced with DST plus anti-CD154 (12). Applicants have now tested whether this regulatory T cell subset is also required for the induction phase of transplant tolerance. Interestingly, the consequences of CD4+CD25+ T cell subset depletion were similar to the effects induced by ex-Tim-3-Ig administration, and rapid rejection of the islet allografts was observed in anti-CD25 mAb treated hosts (FIG. 9A).

Figure 9B:
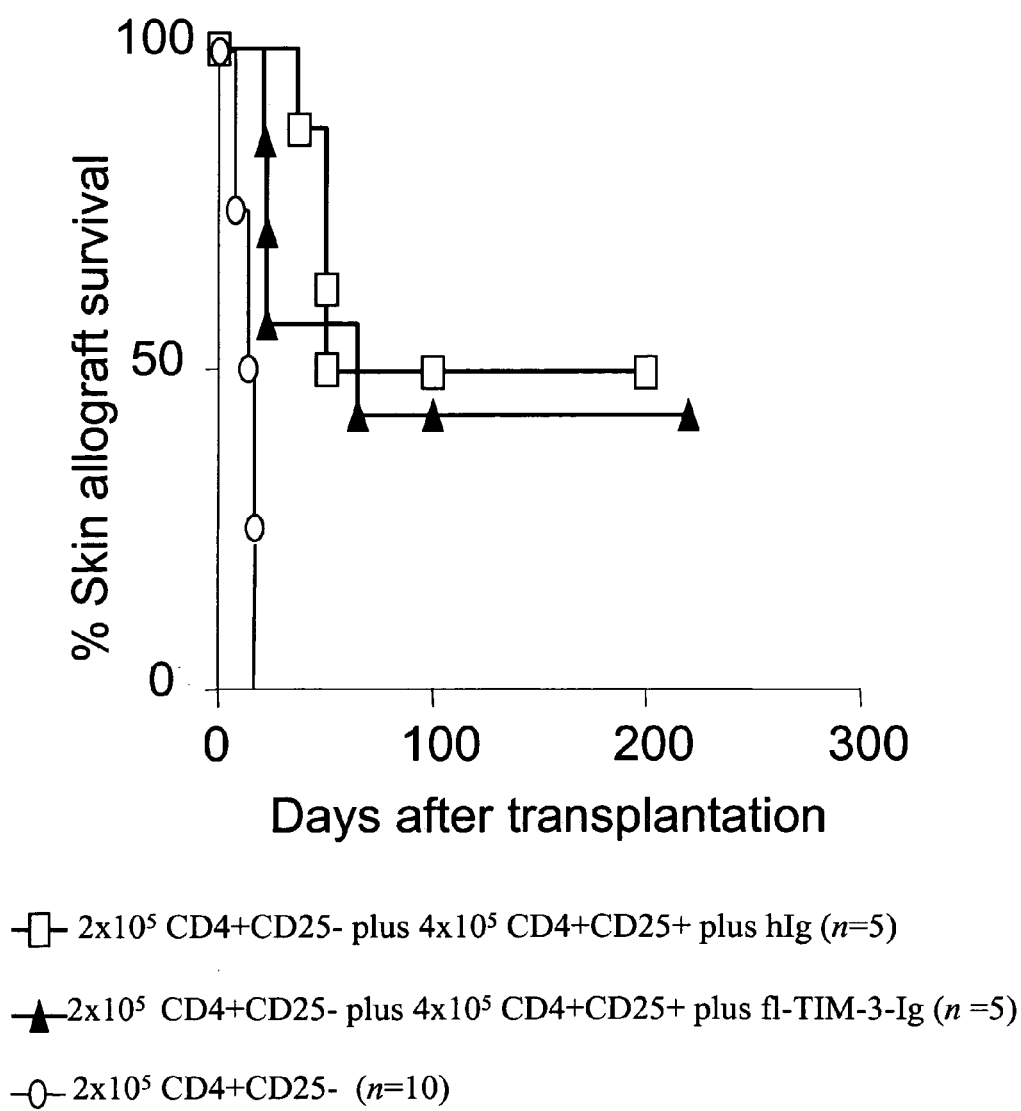

Based on these results, it was hypothesized that engagement of TIM-3 expressed on Th1 effector cells by TIM-3L bearing CD4+CD25+ regulatory T cells present in naïve hosts might be a pre-requisite for their immunosuppressive function. To determine whether regulatory T cells harvested from naïve mice can exert their immunosuppressive function in the absence of TIM-3 engagement, adoptive transfer experiments were conducted assessing the capacity of naïve CD4+CD25+ T cells to prevent allograft rejection mediated by CD4+CD25− T cells in the presence of TIM-3 blockade. In this model, the transfer of as few as $1 \times 10^5$ CD4+CD25− or CD8+ T cells into immunodeficient MHC-mismatched skin allograft recipients results in rapid skin allograft rejection, while transferred naïve CD4+CD25+ T cells do not induce rejection and prevent CD4+CD25− effector T cell populations from destroying the grafts(33,34). Administration of ex-Tim-3-Ig to C3H/He Scid recipients of DBA/2 skin allografts did not inhibit the capacity of transferred naïve CD4+CD25+ T cells to prevent co-transferred CD4+CD25− T cells from mounting allograft rejection (FIG. 9B). Similar results were observed in vitro when naïve CD4+CD25+ T cells were co-cultured with either naïve CD4+CD25− T cells or Th1 polarized CD4+ T cells, and stimulated with soluble anti-CD3 in the presence of ex-Tim-3-Ig. In addition, the transfer of $1 \times 10^5$ CD4+CD25− T cells alone resulted in equally rapid skin graft rejection regardless of whether ex-Tim-3-Ig or a control hIgG were administered.

Taken together these results indicate that CD4+CD25+ regulatory T cells harvested from naïve alloantigen-inexperienced mice can suppress Th1 dependent cytopathic responses in the absence of TIM-3 engagement. Hence, TIM-3 blockade does not abolish the immunoregulatory effector function of alloantigen-inexperienced CD4+CD25+ T cells, nor does it markedly enhance the capacity of CD4+CD25− T cells to reject skin allografts.

Example 17

Figure 9C:
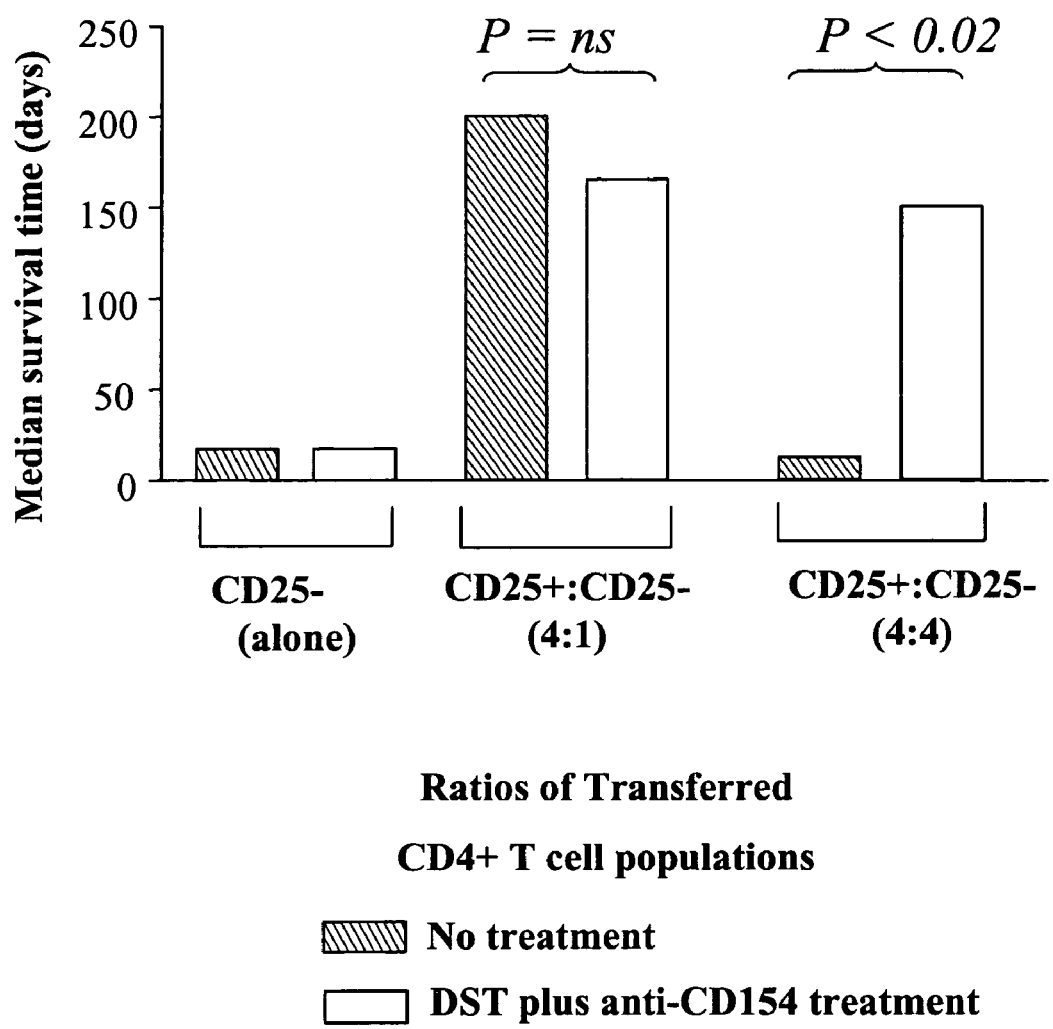

TIM-3 Regulates the Strengthening of the Potency of Alloantigen-Specific CD4+CD25+ Regulatory T Cell Populations Some therapeutic regimens that cause transplant tolerance are known to bolster the potency of alloantigen-specific CD4+CD25+ regulatory T cells(33-35). To determine the impact of DST plus anti-CD154 treatment on the generation of alloantigen-specific CD4+CD25+ T cells, additional adoptive transfer experiments were performed to compare the immunosuppressive capacity of CD4+CD25+ T cells harvested from naïve hosts or from mice treated with DST plus anti-CD 154. CD4+CD25– or CD8+ T cells harvested from treated or untreated naïve mice did not differ in their capacity to promote acute skin allograft rejection (data for CD4+ CD25– T cells are shown in FIG. 9C), indicating that in this model DST plus anti-CD154 treatment does not have a major impact on effector T cell populations. In contrast, CD4+ CD25+ T cells sorted from DST plus anti-CD154 treated hosts exerted a much greater immunosuppressive effect upon naïve CD4+CD25– T cells than CD4+CD25+ T cells harvested from naïve mice. Thus, while naïve CD4+CD25+ T cells could prevent CD4+CD25– T cells from rejecting skin allografts when transferred at a high ratio (4:1) of CD4+ CD25+ to CD4+CD25– (FIG. 9C, middle panel), only CD4+ CD25+ T cells harvested from DST plus anti-CD154 treated hosts were capable of mediating effective immunosuppression at 1:1 ratios of regulatory to effector T cells (FIG. 9C, right hand panel). Remarkably, this enhanced immunosuppressive phenotype noted after DST plus anti-CD 154 treatment was strictly donor-specific, since CD4+CD25+ T cells harvested from hosts tolerized to a different donor strain (C57BL/6) with DST plus anti-CD154 did not mediate greater graft-protective effects than naïve CD4+CD25+ T cells in response to donor DBA/2 skin allografts (median skin allograft survival time 14 and 12 days, n=5 and 7, respectively). Furthermore, both DST and anti-CD154 were required to achieve enhanced immunoregulatory effects, since the provision of alloantigen without CD40-CD 154 costimulation blockade had no detectable effects upon the immunosuppressive function of CD4+CD25+ T cells in vivo.

Figure 9D:
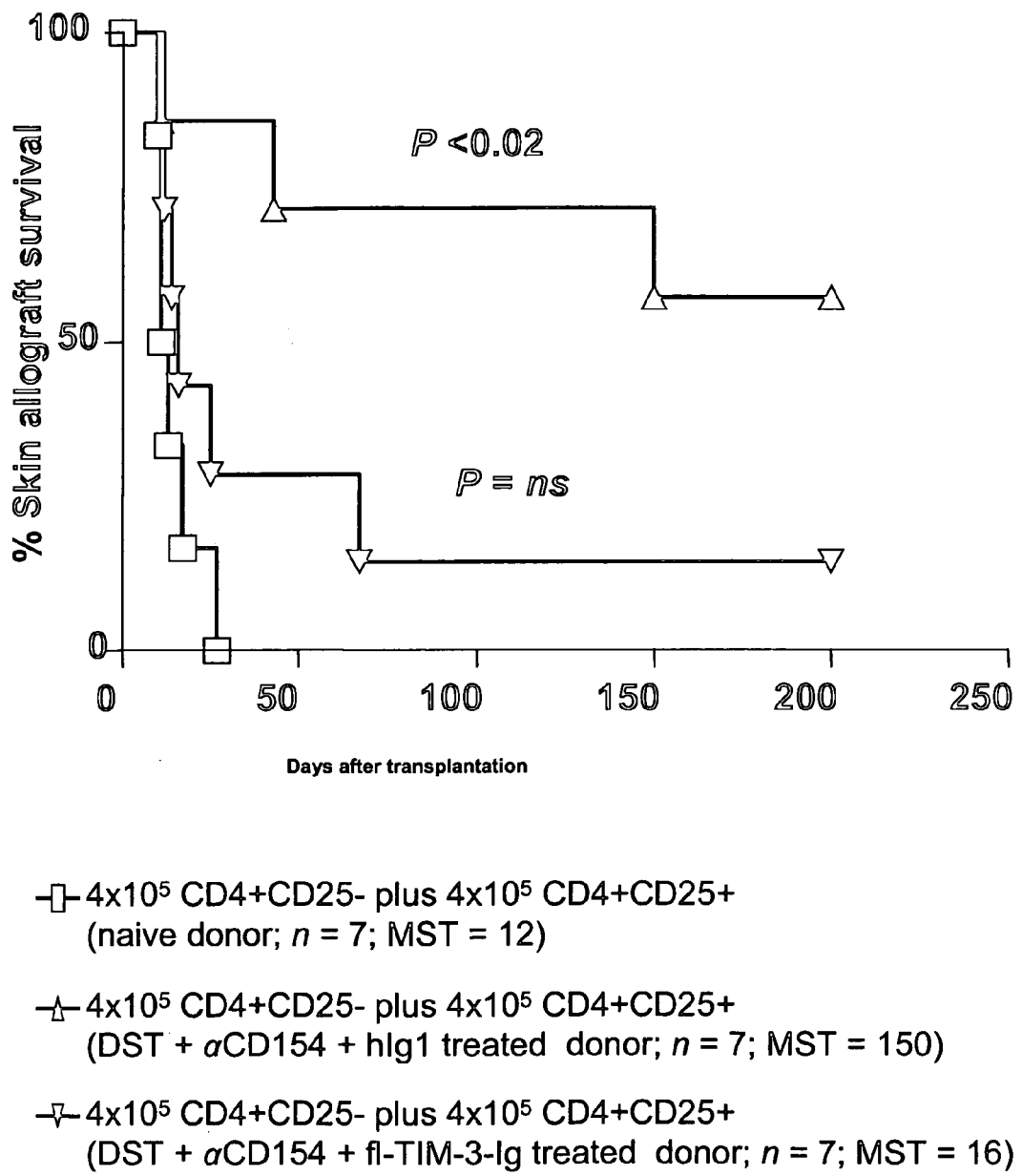

These observations suggest that DST plus anti-CD 154 exerts its tolerizing effect, in large measure, by enhancing the immunosuppressive function of donor-specific CD4+CD25+ regulatory T cells. Applicants then addressed whether TIM-3 pathway was crucial to this therapeutic effect. CD4+CD25+ T cells were harvested from DST plus anti-CD 154 treated mice, and their immunosuppressive function compared in vivo with that of regulatory T cells obtained from hosts treated with DST, anti-CD154 and ex-Tim-3-Ig. The enhanced alloantigen-specific suppressive phenotype conferred by DST plus anti-CD154 treatment was abolished by concurrent administration of ex-Tim-3-Ig (FIG. 9D), since CD4+CD25+ T cells harvested from treated hosts receiving ex-Tim-3-Ig did not exert greater suppressive effects than naïve regulatory cells (FIG. 9D). In these experiments ex-Tim-3-Ig was only administered to CD4+CD25+ T cell donors, and no treatment whatsoever was given to skin transplant recipients, thereby minimizing the likelihood that ex-Tim-3-Ig treatment interfered with interactions between CD4+CD25+ and CD4+CD25– T cells. In fact, in our adoptive transfer model Applicants have observed that the administration of ex-Tim-3-Ig after transplantation does not abrogate the protective effects of previously generated donor-specific CD4+CD25+ T cells. Taken together, our data suggest that: i) the TIM-3 pathway facilitates the acquisition of donor-specific immunoregulatory properties by CD4+ CD25+ T cells during tolerance induction, and ii) TIM-3/ TIM-3L interactions are critical for the generation, but not the immunosuppressive effector function, of donor-specific CD4+CD25+ immunoregulatory T cells.

Example 18

Identification of Galectin-9 as a TIM-3 Ligand

Figure 10A:
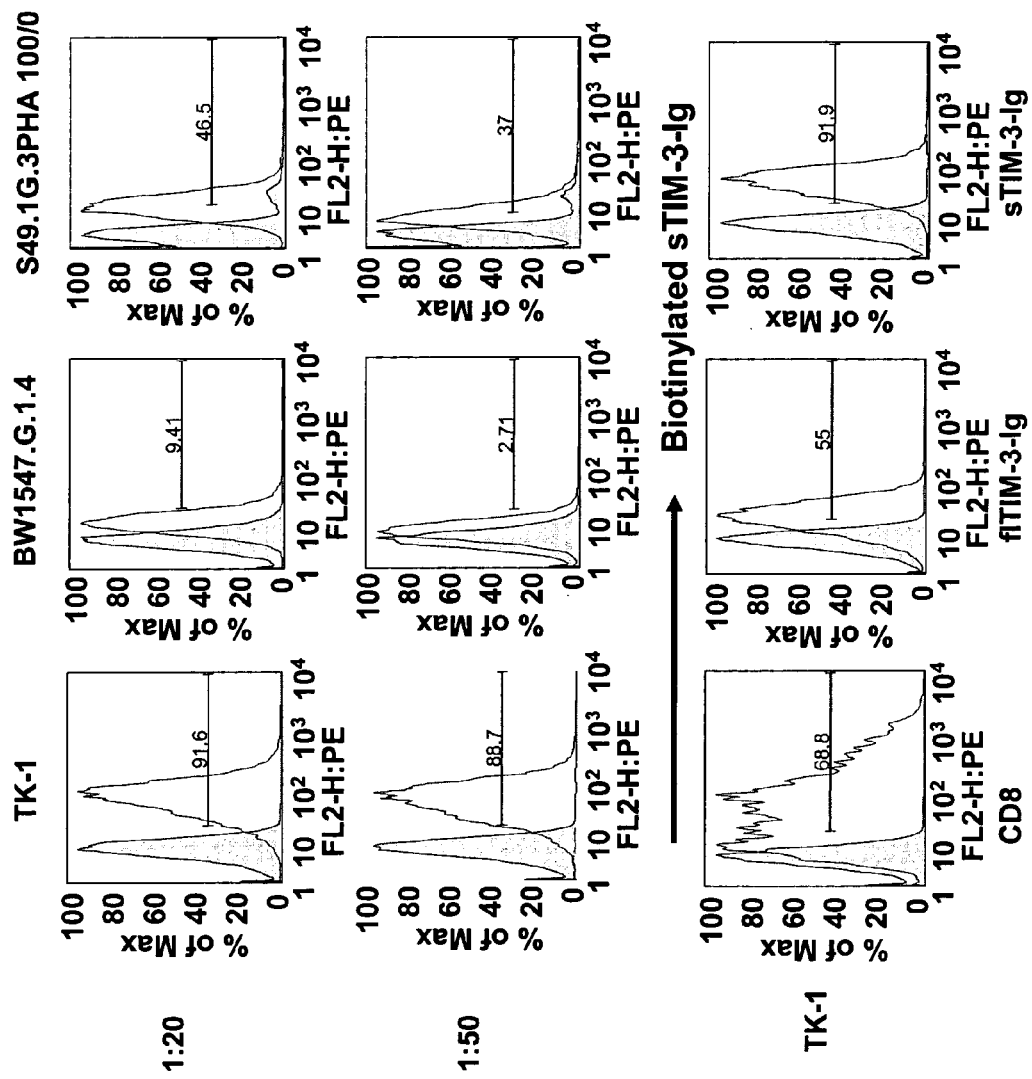
FIG. 10 shows the identification of galectin-9 as a TIM-3 binding protein. (a) TK-1 cells express the highest level of TIM-3 ligand(s). Three T cell lines, TK-1, S49.1G.3PHA 100/0, and BW1547.G.1.4, were stained by biotinylated sTIM-3-Ig (0.4 mg/ml) at 1:20 and 1:50 dilutions, and detected by anti-human IgG-Fc-PE for the TIM-3 ligand expression. All T cell lines are stained positively by TIM-3 fusions FACS analysis, among which up to 90% of TK-1 were positively stained by both flTIM-3-Ig and sTIM-3-Ig. (b) Demonstration of the specific interaction between a 35 kD protein and TIM-3 by pull-down assays. Extracellular membrane associated proteins on live TK-1 cells were biotinylated by NHS-LC-Biotin in PBS pH7.9 buffer at room temperature. Reaction was stopped by DMEM medium after 1 hour incubation. Cell lysate from the biotinylated TK-1 cells was used in pull-down experiment by incubating with 5 μg flTIM-3-Ig, sTIM-3-Ig, TIM-2-Ig, and hIgG respectively plus Protein G-agarose beads at 4° C. Protein samples eluted from beads were treated with or without PNGase F to remove N-linked sugar chains, and applied to SDS-PAGE and Western blot. Only signals from biotinylated membrane associated proteins bound to avidin conjugated peroxidase and were detected by chemiluminescent signal.

To analyze the distribution of expression of the putative TIM-3 ligand(s), cell surface staining by TIM-3-Ig fusion proteins were used to screen TIM-3 ligand expressing cell types. It has been shown that both flTIM-3-Ig and sTIM-3-Ig bind to resting CD4+ T cells and to a small population of splenic CD11c+ dendritic cells and CD11b$^+$ macrophages, but not CD8+ or B220+ cells (Sabatos et al. *Nat Immunol* 4:1102-1110, Sanchez-Fueyo et al. *Nat Immunol* 4:1093-1101) indicating that T1M-3 ligand(s) is predominantly expressed on resting CD4+ T cells. Thus, a number of T cell lines/T cell lymphomas were screened. FACS results demonstrated that three T cell lines tested so far bound sTim-3-Ig, but not human IgG1 control, among which TK-1 (a T cell lymphoma) had the highest binding to sTim-3-Ig (FIG. 10A). Staining by flTIM-3-Ig showed similar results (FIG. 10A).

Figure 10B:
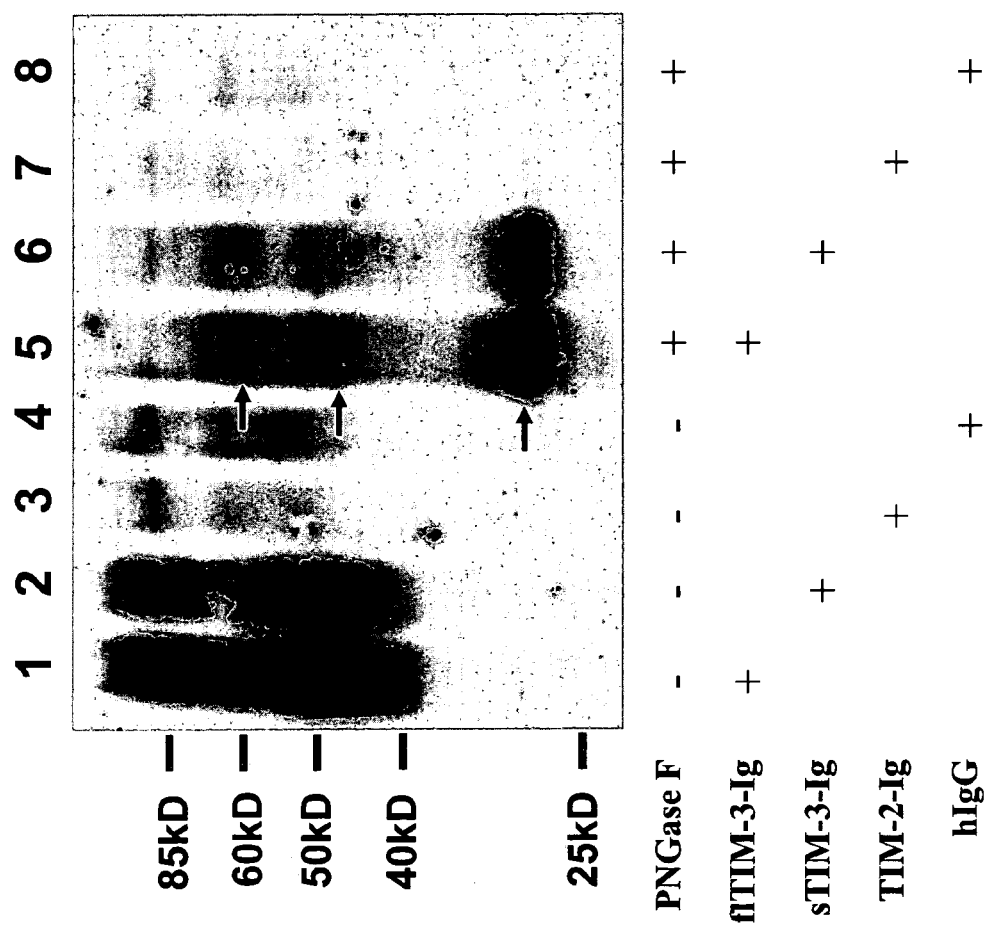

In order to identify specific extracellular membrane associated TIM-3 binding protein, live TK-1 cells were biotin labeled and the whole cell lysates were subjected to the pull-down assay by incubating with TIM-3-Ig fusion proteins. Results from SDS-PAGE-Western blot demonstrated that both flTim-3-Ig and sTim-3-Ig were able to precipitate a protein or protein complex with the molecular weight ranged from 40 to 60 kD (FIG. 1b, lane 1, 2). Compared with the control groups from TIM-2-Ig or hIgG pulled down proteins (FIG. 10b, lane 3, 4), the 40 to 60 kD band is specific for flTIM-3-Ig and sTIM-3-Ig. When N-linked oligosaccharide chains were removed by PNGase F, the molecular weight of the 40 to 60 kD band was reduced to 35 kD. Same experiment using cell lysates from $^{35}$S-Met metabolic labeled TK-1 cells further excluded the possible contamination of this 35 kD band. Mass spectrometry analyses of the 35 kD band extracted from silver stained SDS-PAGE gel identified the protein as galectin-9, a member of the galectin family that is expressed on lymphocytes and other cell types.

Example 19

Specific Interaction Between Galectin-9 and TIM-3

Galectins are a group of β-galactoside binding lectins containing the Carbohydrate Recognition Domain (CRD) to bind sugar moieties on the cell surface; they are major regulators of immune cell homeostasis (Rabinovich et al. *Trends Immunol* 23:313-320; Rabinovich et al. *Biochim Biophys Acta* 1572: 274-284.). Galectins do not have signal peptides for ER-Golgi pathway secretion. Like IL-1, galectins secrete extracellular via alternative pathways. The total RNA from TK-1 cells was prepare for RT-PCR to clone galectin-9 cDNA. Two galectin-9 coding sequences were cloned and were later found as regular galectin-9 cDNA and its long isoform that has 31 amino acids insertion in the hinge region of the two CRD domains of galectin-9 has been reported to be predominantly expressed in intestine epithelia.

Figure 11A:
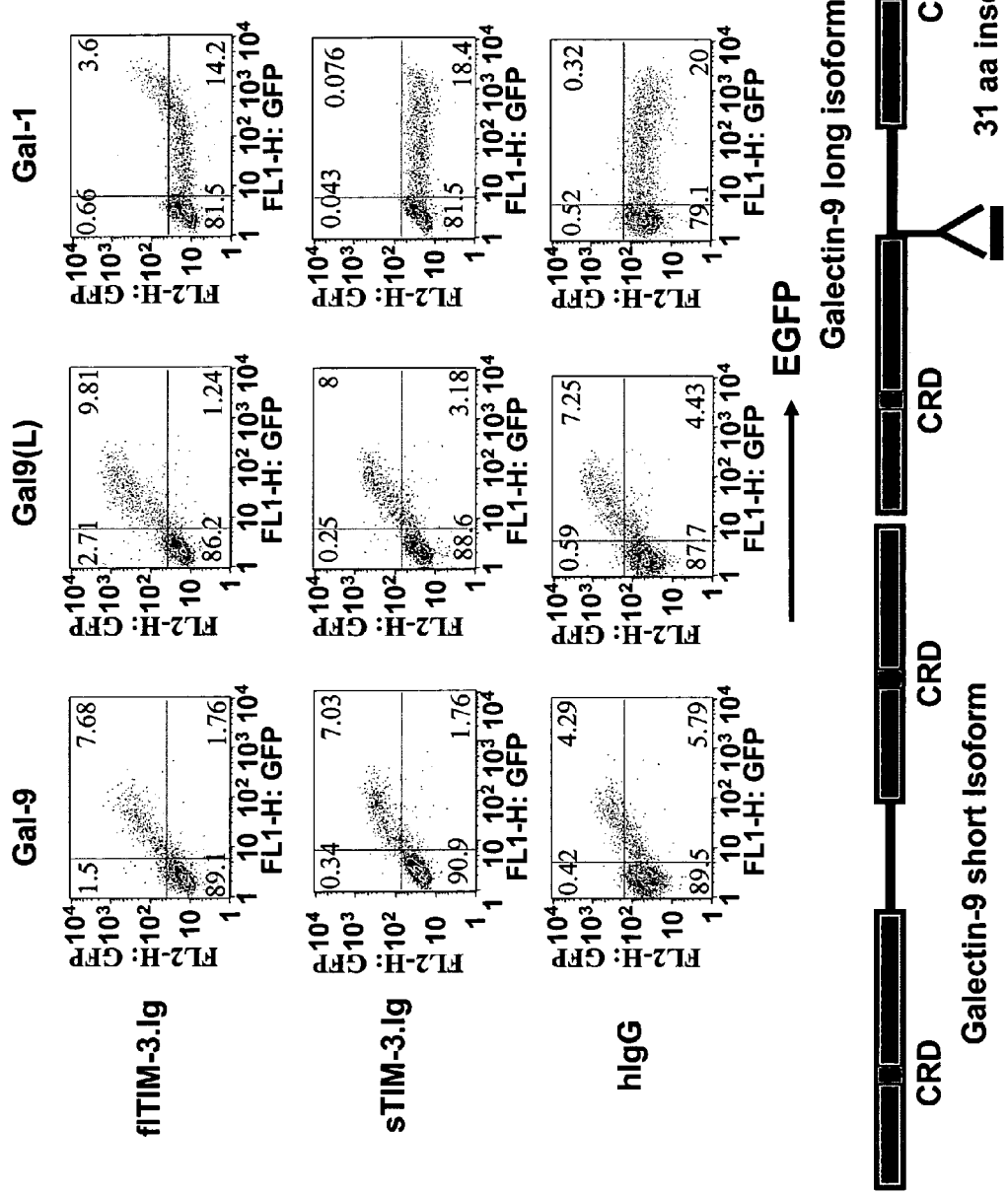
FIG. 11 shows specific interaction between galectin-9 and TIM-3. (a) Both regular and long isoforms for galectin-9 (galectin-9 and galectin-9-L respectively) are able to bind to TIM-3. Protein sequences between two galectin-9 isoforms are identical except a 31 amino acid peptide insert in the hinge region of galectin-9-L. Murine cDNAs for isoforms of galectin-9 from TK-1 cells were subcloned into a eukaryotic bicistronic expression vector pIRES2-EGFP. The plasmids were transiently transfected into CHO cells respectively. Cells were fixed for intracellular staining with flTIM-3-Ig, sTIM-3-Ig, and hIgG and detected by anti-human IgG-Fc-PE 48 hours after transfection. EGFP positive signals in FACS analyses indicated transfected cells. The anti-human IgG-Fc-PE was used to detect the binding from Ig fusions or hIgG. (b) Murine cDNAs for galectin-9, -4, -3, and -1 were subcloned into pIRES2-EGFP. The plasmids and the empty vector that only produces EGFP were transiently transfected into CHO for intracellular staining by s-TIM-3-Ig respectively. The anti-human IgG-Fc-PE was used to detect sTIM-3-Ig binding. (c) Galectin-9 cDNA was subcloned into prokaryotic expression vector pTrcHis 2B. Recombinant galectin-9 (r-galectin-9) was expressed in BL21 E. coli strain and purified through lactose agarose column. Two μg of purified galecin-9 was used to incubate with Ig fusion proteins for pull-down experiment. Elutes from protein G beads were applied to SDS-PAGE and stained by Coomassie blue. Lanes 1 to 3 represent elutes from sTIM-3-Ig, TIM-2-Ig, and TIM-4-Ig and their captured protein respectively. Lanes 4 to 6 stand for Ig fusion protein only. The molecular weight of r-galectin-9 is 38 kD.
Figure 11B:
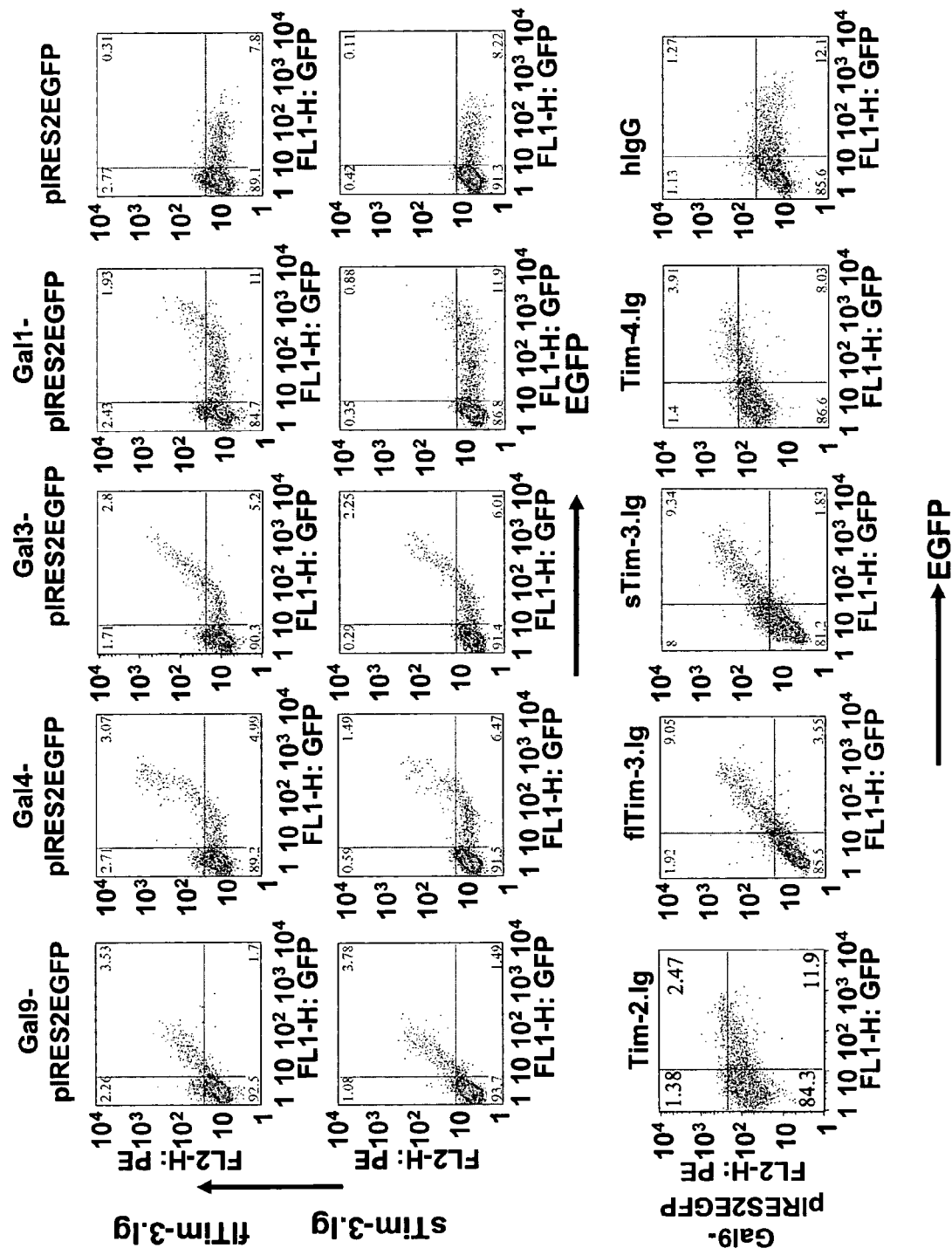

To confirm the interaction between galectin-9 and TIM-3, both galectin-9 isoform cDNAs were subcloned into an expression vector that bicistronically expresses EGFP protein. When galectin-9 expression plasmids were transiently transfected into CHO cells, cells that express EGFP will simultaneously express galectin-9. In transient transfection, expression of galectin-9 was not detected on the cell surface. It is possible that expression of galectin-9 in transiently transfected CHO cells might be separated from the alternative transporting machinery. Therefore the protein product may accumulate in the cytoplasm. It is indeed that intracellular staining revealed the same positive staining pattern by sTIM-3-Ig and flTIM-3-Ig from transfected CHO cells that are EGFP positive, suggesting no differences between regular galectin-9 and its long isoform when interacting with TIM-3 fusions. However neither of them was able to bind to hIgG control (FIG. 11A).

Figure 11C:
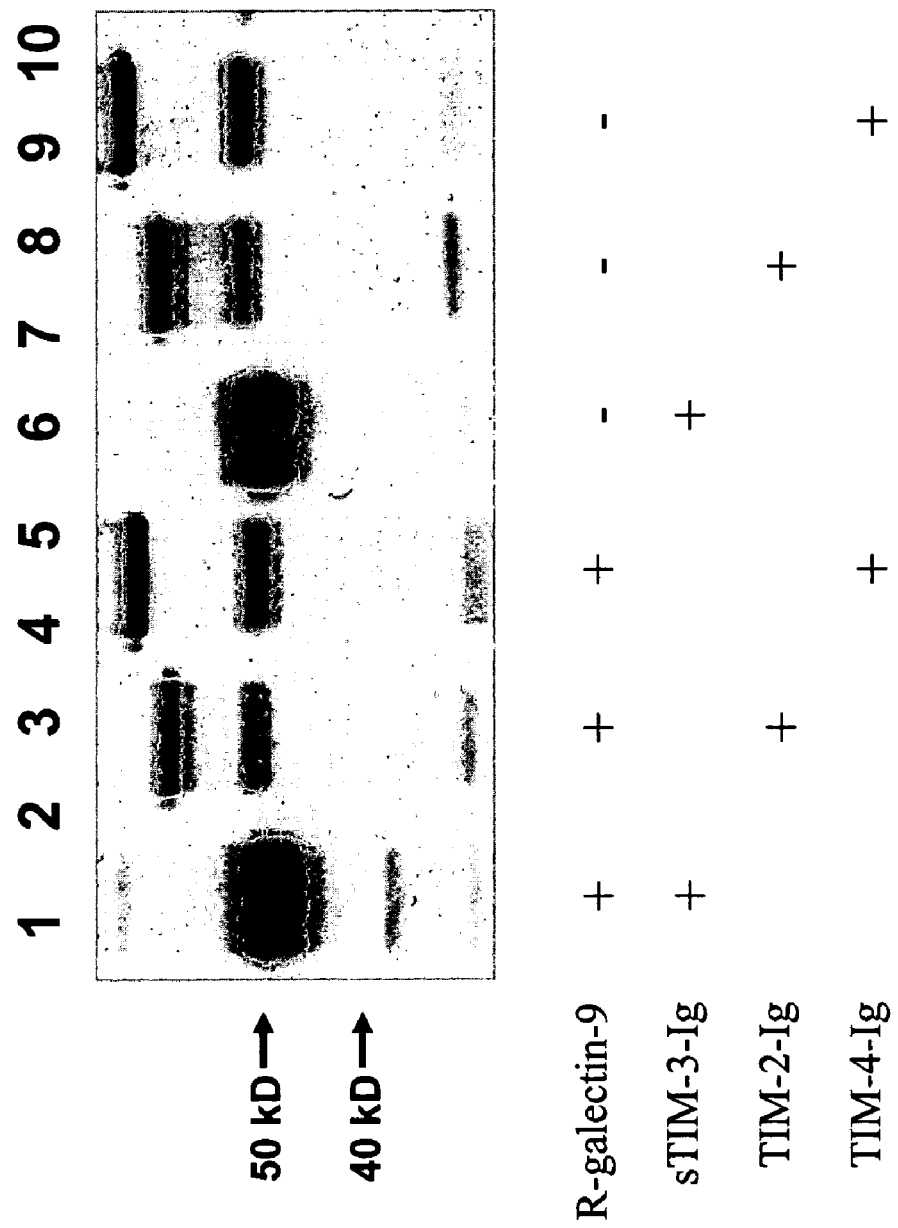

To demonstrate the binding specificity between galectin-9 and TIM-3, galectin-9 transiently transfected CHO cells were subjected to intracellular staining. FlTIM-3-Ig and sTIM-3-Ig are the only fusion proteins that have all positive staining in galectin-9 expressing cells. By contrast, TIM-2-Ig, TIM-4-Ig, and hIgG cannot bind to the same transfected CHO cells, suggesting TIM-3 has the highest affinity to galectin-9 comparing with other TIM family members. As an alternative approach, purified recombinant galectin-9 can be specifically pulled down by sTIM-3-Ig, but not TIM-2 and TIM-4 Ig fusions (FIG. 11C). On the other hand, both flTIM-3-Ig and sTIM-3-Ig only showed positive binding to galectin-9 expressing cells, whereas they did not bind to galectin-1, 3, and 4 unless the cells expressed very high level of these proteins, suggesting certain level of nonspecific interaction between TIM-3 and these galectins (FIG. 11C).

Figure 12A:
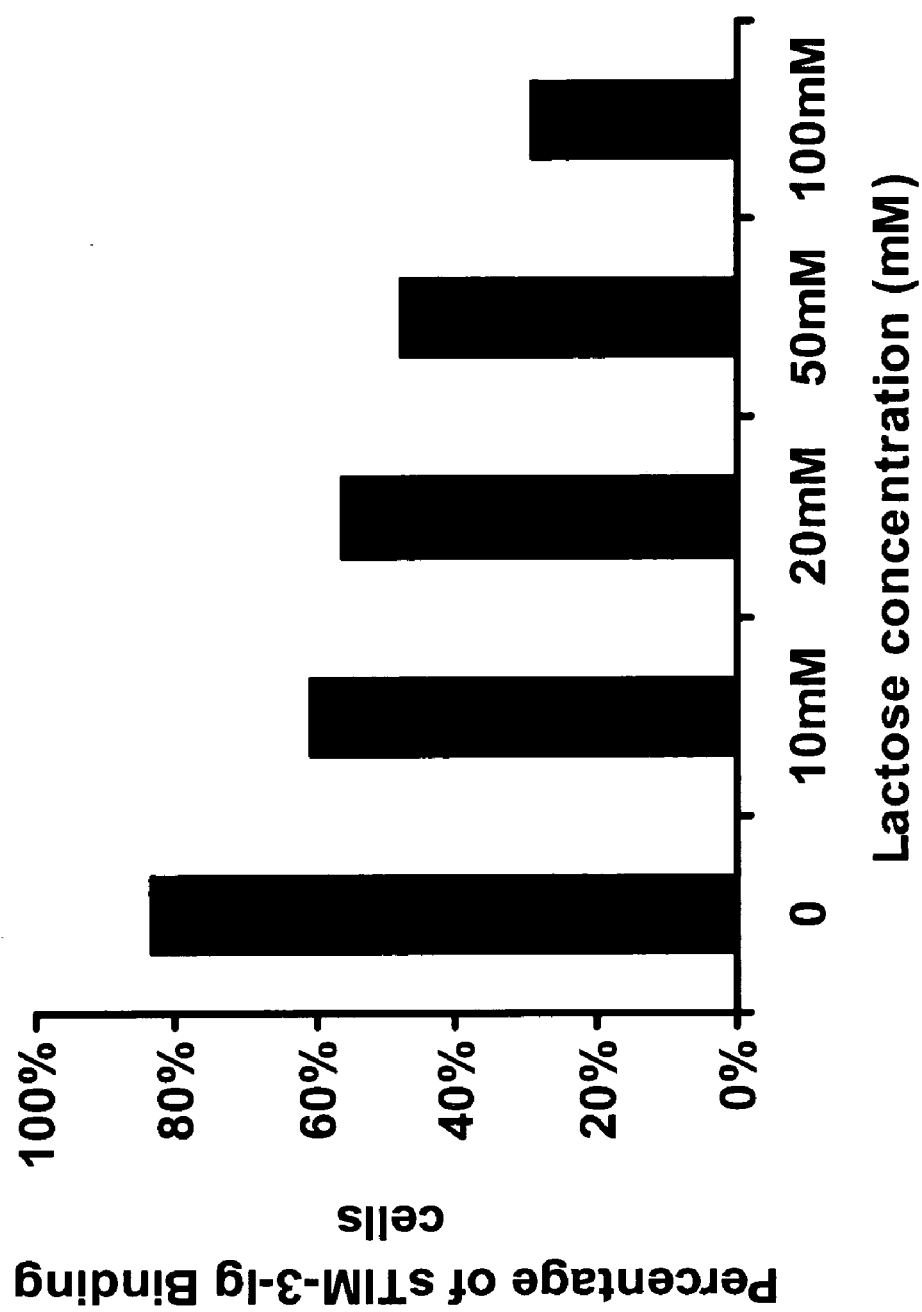
FIG. 12 shows galectin-9 recognizes the β-galactoside bond in oligosaccharide chains of TIM-3. (a) Galectin-9 expression plasmid was transiently transfected into CHO cells and fixed for intracellular staining by sTIM-3-Ig. Incubation buffers with different concentrations from 0 to 100 mM of α-lactose were used in the experiments. Bars in the histograph represent percentage of double positive cell population for EGFP and sTIM-3-Ig staining in presence of different concentration of α-lactose. (b) Two μg of r-galectin-9 was mixed with 4 μg sTIM-3-Ig in presence of different concentration of a-lactose from 0 to 100 mM in a pull-down experiment. Elutes from protein G beads were applied to SDS-PAGE and stained by Coomassie blue. A band at 50 kD represents sTIM-3-Ig, and the one at 38 kD stands for r-galectin-9. (c) CRD domains in galectin-9 are required for interaction with TIM-3. Constructs with mutation of R64A in N-terminal CRD domain, R238A in C-terminal CRD domain, or both were generated and subcloned into expression vector pIRES2-EGFP. CHO cells were transiently transfected by wt and mutant galectin-9 expression plasmids for intracellular staining by sTIM-3-Ig. EGFP and anti-human IgG-Fc-PE double positive standard for interaction between galectin-9 and sTIM-3-Ig.
Figure 12B:
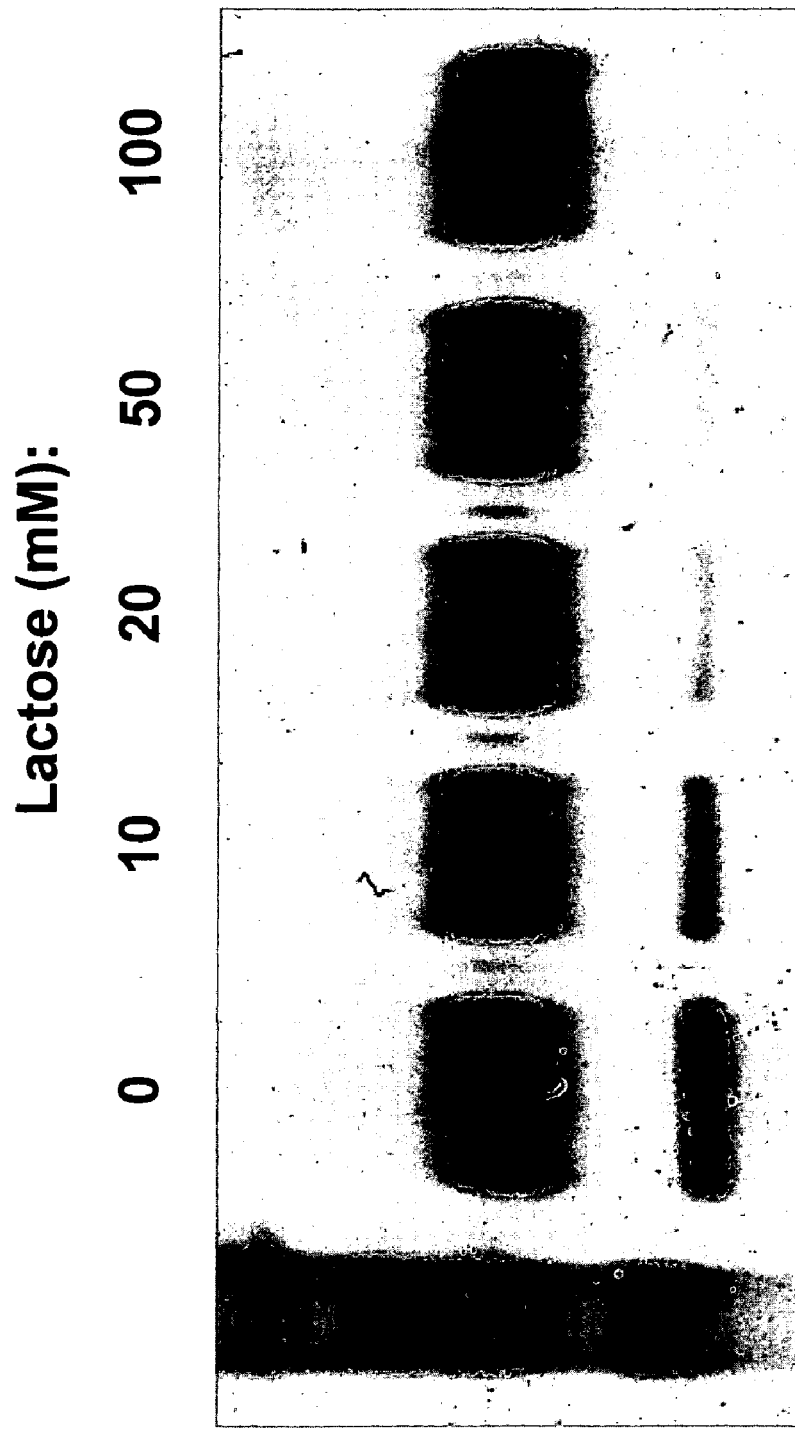
Figure 12C:
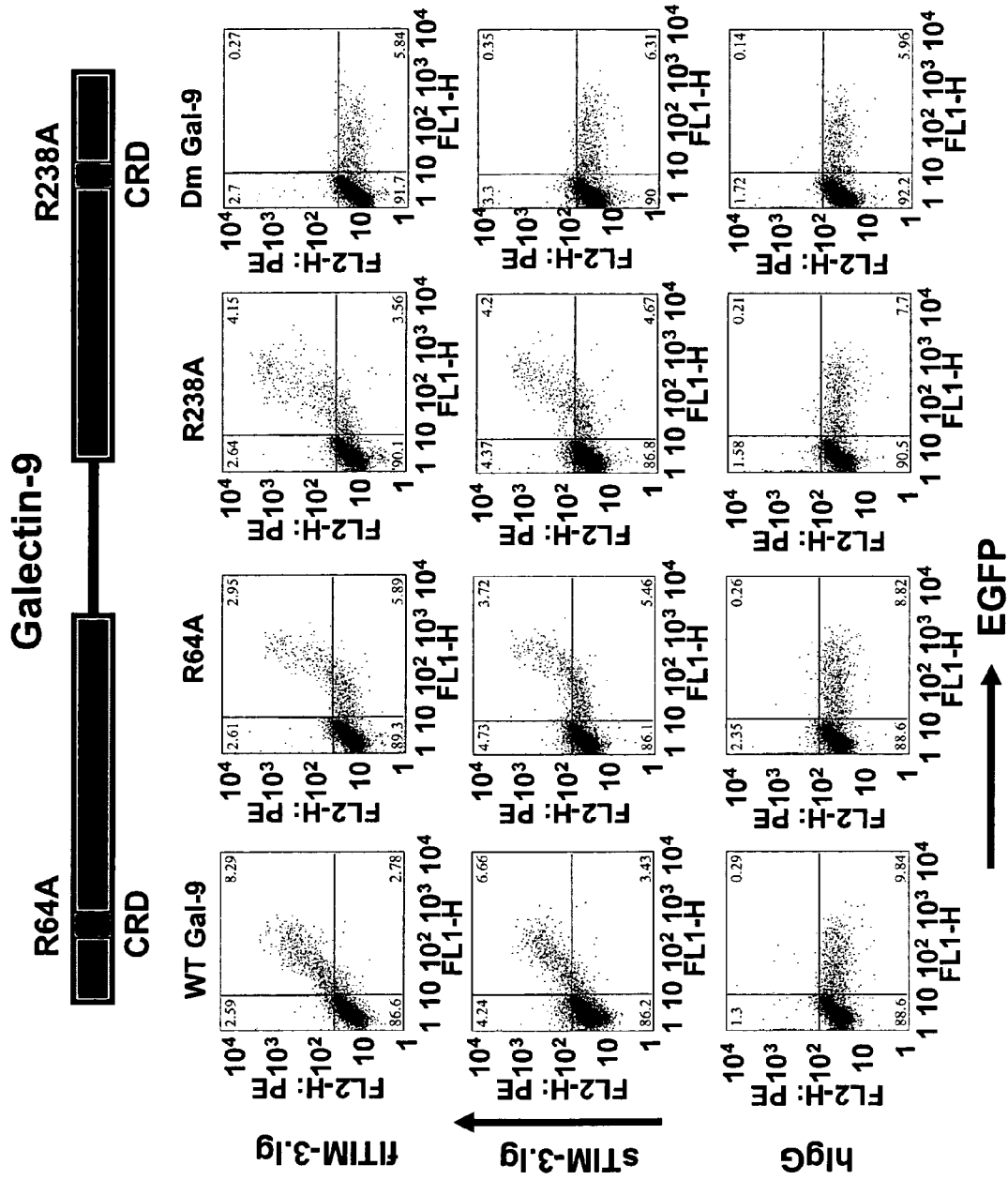

In conclusion, galectin-9 is a protein that specifically binds to the TIM-3 extracellular portion. As both flTIM-3-Ig and sTIM-3-Ig can bind to galectin-9, the Ig V domain on TIM-3 may be responsible for interaction with galectin-9. When lactose was added in the incubation buffer, interaction between galectin-9 and TIM-3 was attenuated in both intracellular staining and pull-down assay in a dose-dependent manner (FIG. 12A). Furthermore, mutant galectin-9 constructs that disrupt either the N-Terminal CRD or the C-terminal CRD partially lose interaction to TIM-3, whereas double mutations in both CRD domains completely abrogated binding to TIM-3 (FIG. 12B). Therefore, the interaction between galectin-9 and TIM-3 is dependent on the CRD domains in of galectin-9.

Example 20

Roles of TIM-3-Galectin-9 in Regulation of Effector Th1 Cells

Figure 13A:
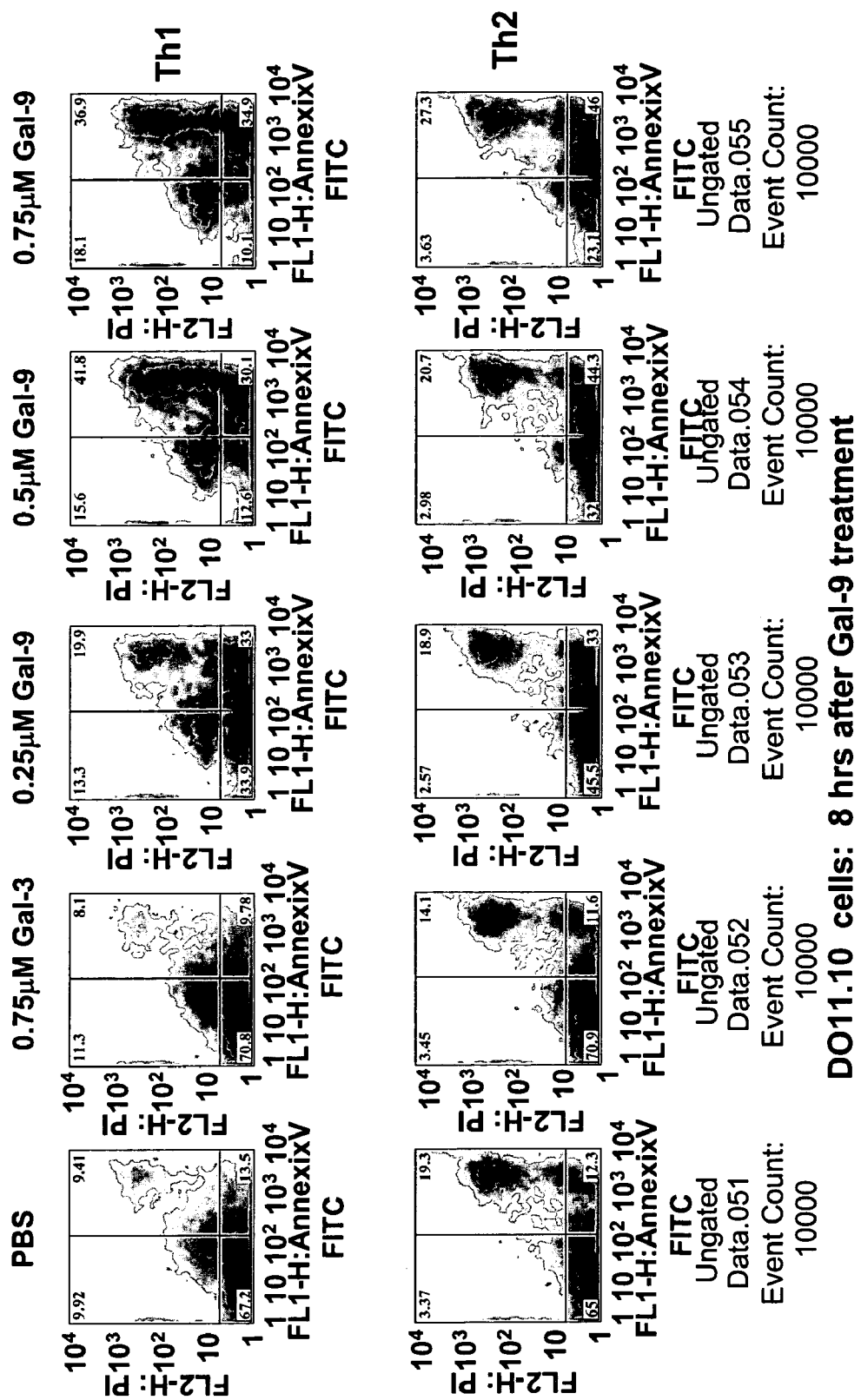
FIG. 13 shows galectin-9 induces apoptosis in activated murine Th1 cells and its apoptotic effect is functionally related to its interaction to TIM-3. (a) Spleen CD4+CD62L+ T cells from DO11.10 transgenic mice were in vitro polarized into Th1 and Th2 cells for at least 3 rounds. The Th1 and Th2 cells 3 day after stimulation by VOA peptide and APCs were treated with PBS, galectin-3, and different doses of galectin-9. After 8 hours, cells were stained with PI and Annexin V-FITC for detecting apoptotic cells. PI positive populations (both PI+Annexin V+ and PI+Annexin V−) are dead cells or late stage apoptotic cells. PI−Annexin V+ population is early stage apoptotic cells; and double negative population is life cells. (b) Th1 and Th2 cells were treated with PBS, 0.75 mM galectin-9, 0.75 mM galectin-9 for 0, 2, 4, 8, and 12 hours. Cells were harvested for nucleosome enrichment assays. The fragmented nucleosomal structures released into cell lysate supernatant are induced by apoptotic procedure, and were detected by antibodies against histone and genomic DNA in the ELISA assay and read at OD 405 nm. As in (a), Th2 cells were resistant to apoptotic effects from galectin-9.
Figure 13B:
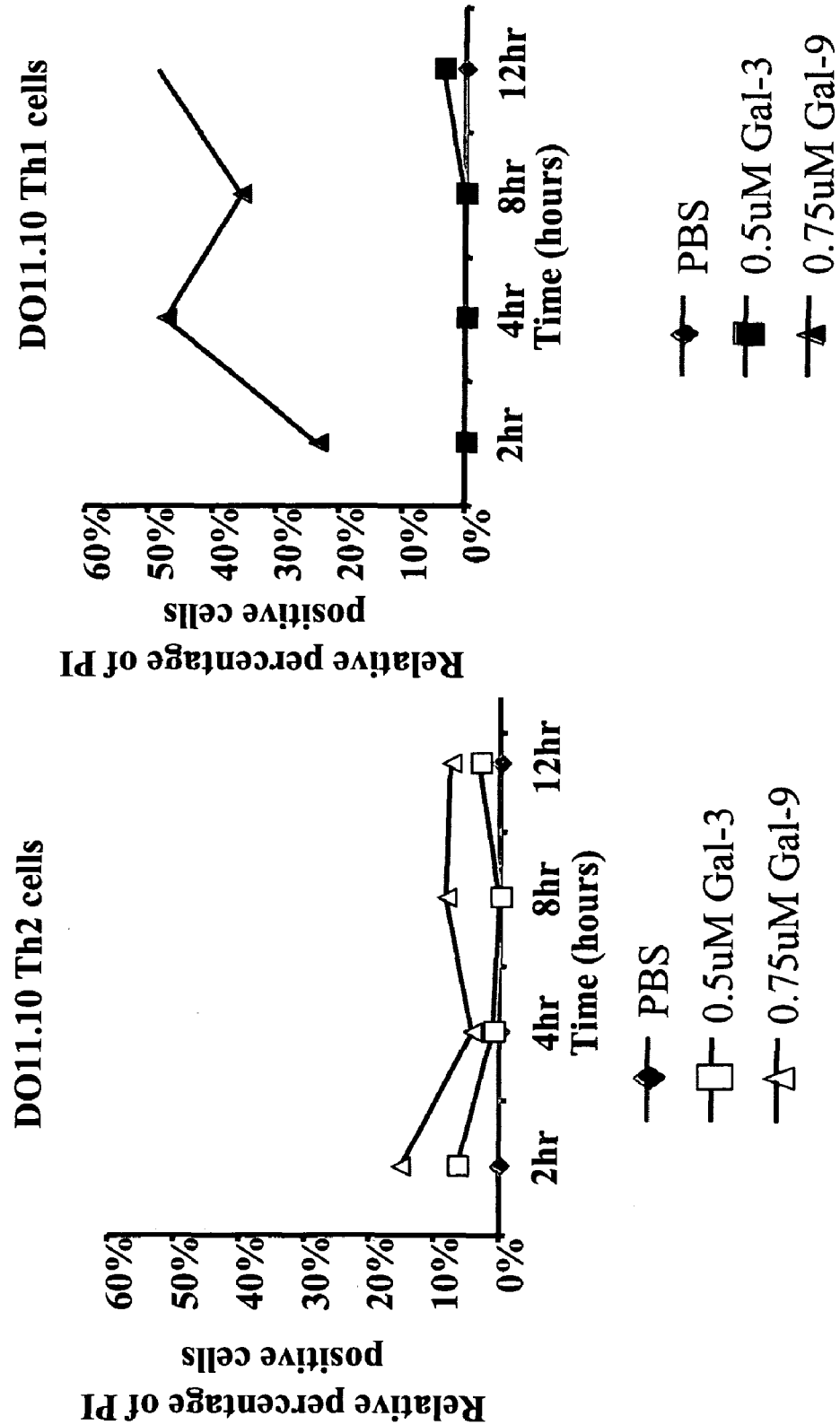

Applicants hypothesized functional roles of a galectin-9-TIM-3 pathway in the regulation of Th1 cell expansion and homeostasis by an apoptotic mechanism. To test the apoptotic effects of galectin-9 in effector T cells, naïve spleen CD4+ T cells from DO11.10 transgenic mice were purified by a CD4 T cell negative selection column and sorted for CD4+CD62L+ cells. Cells were in vitro stimulated with VOA peptide and irradiated APC, and were polarized in vitro for at least 3 rounds into Th1 and Th2 cells. When active Th1 cells were treated with recombinant galectin-9, cell death was induced in the majority of cells. By contrast, activated Th2 cells were resistant to galectin-9-induced cell death (FIG. 13). Further experiments performed on AE7 (Th1 cell line) and D10G4 (Th2 cell line) demonstrated the similar effects of cell death induced by recombinant galectin-9 in vitro.

Example 21

Recombinant Galectin-9 Attenuates Th1 Cell Activation

Figure 14A:
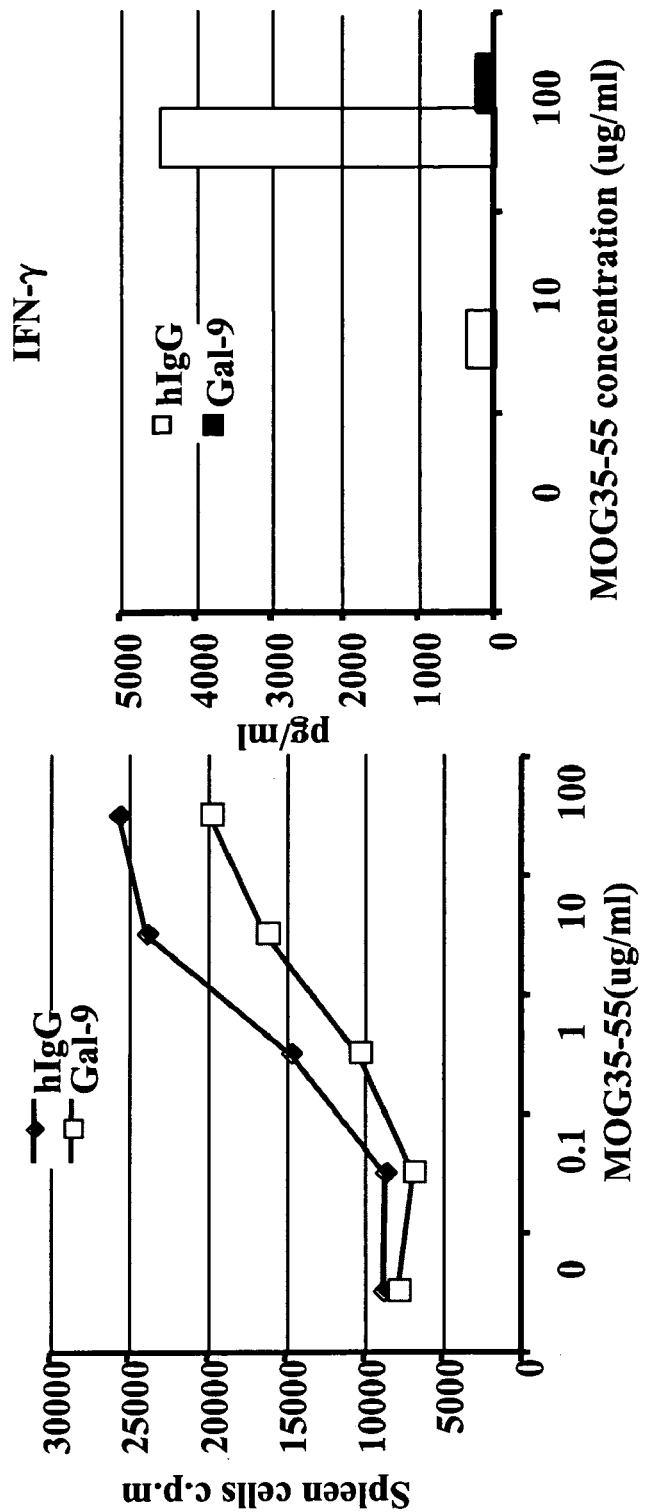
FIG. 14 shows administration of galectin-9 in mice results in reduction of IFN-γ and IL-2 production by downregulating IFN-g and IL-2 producing cells. However it does not affect the whole spleen cell proliferation. C57BL/6J mice were immunized with 100 mg MOG35-55 peptide plus 200 ml CFA. R-galectin-9 was i.p. injected to the mice everyday from day 3 to day 9. Mice were sacrificed and spleen cells were harvested for cell proliferation assay, ELISA, and ELISPOT.
Figure 14B:
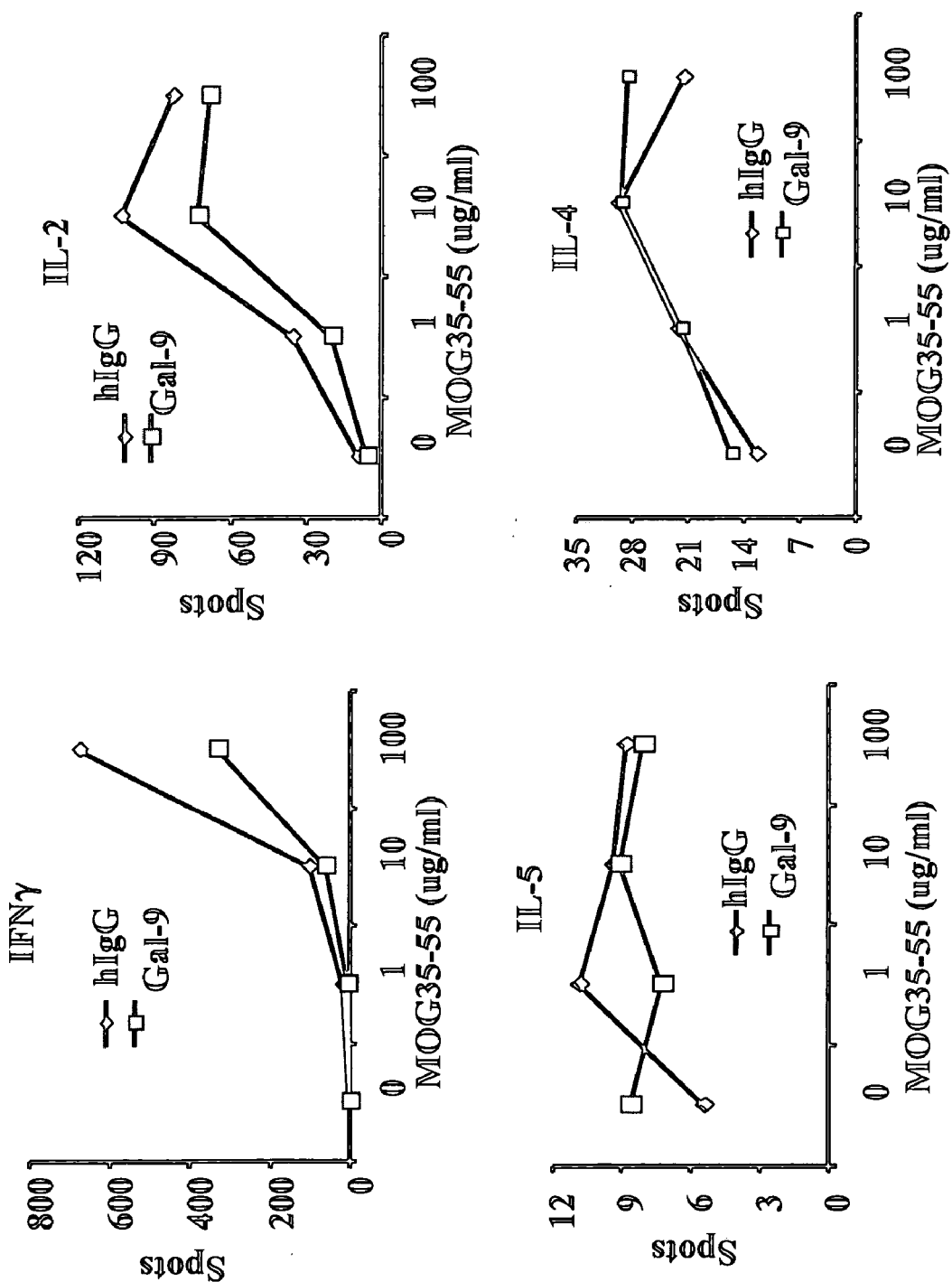

To determine the in vivo effects of the interaction of galectin-9 and TIM-3 during a Th1 immune response, C57BL/6J mice were immunized with MOG 35-55 in complete Freund's adjuvant (CFA). Recombinant galectin-9 (100 μg) was i.p. injected to immunized mice daily from day 3 to 9. Spleen cells were harvested for cell proliferation and cytokine production assays. Comparing with a PBS treated control group, galectin-9 administration did not alter spleen cell proliferation by $^3$H thymidine incorporation, however, ELISA results indicated more than 50 percent reduction in IFN-γ production. ELISPOT further demonstrated that fewer cells from galectin-9 treated spleen produced IFNγ and IL-2. Interestingly, IL-4 and IL-5 production was not changed compared with PBS treated mice (FIG. 14).

Example 22

Therapeutic Effect of Galectin-9-TIM-3 in Treatment of EAE

TIM-3 has been demonstrated to have an important function in regulating Th1 cell responses and peripheral tolerance. Its expression is correlated to pathology of both EAE and human multiple sclerosis (MS). Interestingly, expression of galectin-9 in astrocytes is induced by IL-1β, indicating that this protein may be involved in limiting inflammation in the CNS (Yoshidaet et al. *Neuroreport* 12:3755-3758). As TIM3-TIM-3 ligand(s) interaction may regulate Th1 responses and promote immunological tolerance, it is possible that both these functions are mediated by the interaction of TIM-3-galectin-9. To address this possibility, recombinant galectin-9 will be administered to MOG peptide 35-55/CFA immunized C57BL/6J mice every other day from the day of immunization. The disease will be monitored and brains and spinal cords will be examined histopathologically. As a functional ligand for TIM-3, galectin-9 administration is expected to reduce the severity of EAE, and/or induce tolerance against EAE. As a control, Applicants will also test the Tim-3−/− mice in the C57BL/6J background. It is expected that Tim-3 deficient mice will not be affected by administration of galectin-9.

D. DISCUSSION OF SECOND SERIES OF EXPERIMENTS

The expansion and differentiation of Th precursors into the Th1 or Th2 pathways regulate the outcome of immune responses to bacterial, viral, auto- and allo-antigens. The extent of these T cell responses is influenced by cytokines and a group of accessory molecules that includes TNF receptor(7) and Ig superfamily members(8). TIM-3 is a novel Th1-specific Ig superfamily member recently identified by Monney et al. (10), as a negative regulator of tissue destructive immune responses in EAE. In this model, anti-TIM-3 mAb treatment increased the number and activation level of macrophages, and the severity of tissue injury within the brain. Based on these results, it was proposed that anti-TIM-3 might activate macrophages by enhancing the migration of Th1 cells into the brain or by blocking the interaction between TIM-3 and a putative inhibitory TIM-3L.

Applicants have identified TIM-3 by comparing the gene expression profiles of activated Th1 and Th2 clones, and Applicants now report that TIM-3 plays an important role restraining Th1-mediated responses, both in auto- and allo-immune models, and that these effects appear to be mediated, at least in part, by the modulation of the immunosuppressive function of CD4+CD25+ regulatory T cell populations.

CD4+CD25+ regulatory T cells play a central role in the maintenance of self-tolerance(36-38), as well as in the long-term acceptance of allogeneic transplants(12,34,35).

Although their exact mechanism of action has not been defined as yet, both cell-to-cell contact interactions and soluble factors are implicated in their immunosuppressive function (39,40). Our results indicate that TIM-3 is not the molecular pathway through which these CD4+CD25+ T cells deliver their immunosuppressive effects, since CD4+CD25+ T cells from naïve or tolerant hosts can strongly suppress CD4+CD25– T cells lacking effective expression of TIM-3 both in vivo and in vitro (FIG. 9B). However, a TIM-3/TIM-3L sensitive pathway is responsible for the functional generation of donor-specific CD4+CD25+ regulatory T cells that emerge after the administration of tolerizing treatments such as DST plus anti-CD 154 treatment (FIG. 9D). Hence, both TIM-3 dependent and independent pathways are involved in CD4+CD25+ T cell dependent immunoregulation.

Although the precise cellular and molecular interactions involving TIM-3 and its ligand(s) remain to be fully elucidated, the expression patterns seen for TIM-3 and TIM-3L (FIG. 8A-D) suggest that a direct interaction between TIM-3 positive Th1 effector cells and TIM-3L positive regulatory T cells might constitute a mechanism through which CD4+CD25+ T cells acquire enhanced immunosuppressive function. Alternatively, given that TIM-3L expression is also observed on some dendritic cells, TIM-3 effects on regulatory T cells could be indirectly exerted through the intervention of APCs. This last interpretation would be consistent with observations concerning the role of dendritic cell phenotype in the modulation of CD4+CD25+ T cell mediated immunoregulation(41,42) Finally, the fact that TIM-3 is capable of recruiting src kinases upon ligation, and therefore capable of influencing downstream signaling events, indicates that TIM-3 ligation could also exert a direct inhibitory signal upon Th1 cells themselves. Nevertheless, the absence of a significant increase in the frequency of IL-2- and γIFN-producing effector T cells in the spleens of ex-Tim-3-Ig treated transplant recipients, suggests that in transplantation TIM-3 has a more potent effect upon regulatory than upon effector T cell populations.

Our findings offer a novel insight into the mechanisms through which DST plus anti-CD154 promote tolerance induction in transplantation. The current understanding states that the provision of alloantigen to host T cells in the context of an anti-CD154 induced immunosuppressive environment directly inactivates alloreactive CD4+ and CD8+ T lymphocytes by anergy and/or apoptosis, and subsequently promotes the expansion of regulatory T cells capable of self-perpetuating the tolerant state(11-13,28,43). Applicants now provide evidence indicating that in polyclonal systems, DST plus anti-CD154 acts primarily by increasing the immunosuppressive function of CD4+CD25+ T cells in an alloantigen-specific manner, while the effects of treatment on the capacity of effector T cell populations to reject allografts are much less potent.

The mechanisms through which prior encounter with alloantigen in the absence of CD40-CD 154 costimulation induce these TIM-3-sensitive immunoregulatory networks are speculative. Regulatory T cell clones capable of recognizing allogeneic peptides might undergo selective expansion (44,45) and/or acquire a more efficient immunosuppressive function, thereby strengthening donor-specific immunoregulatory circuits. Indeed, the lack of effect of DST monotherapy in our model suggests that CD154 blockade, known to promote effector T cell apoptosis and anergy(13,43), spares or even enhances the function and survival of regulatory T cells. Alternatively, CD40-CD 154 costimulation blockade might modulate the phenotype of resident APCs, resulting in the recruitment into the immunoregulatory compartment of naïve donor-reactive T cells undergoing activation. Interestingly, lack of CD40 expression on APCs has been reported to promote antigen-specific tolerance(46-49), in some cases through the generation of CD4+ regulatory T cells(49). Hence, based on our findings, Applicants speculate that CD40 and TIM-3 have opposing effects and that their balance serves as a checkpoint in the decision between tolerance and immunity. The importance of TIM-3/TIM-3L pathway facilitating immunological tolerance is not exclusively restricted to the mechanisms through which DST plus anti-CD 154 achieve transplantation tolerance. Indeed, based on own observations that ex-Tim-3-Ig abrogates tolerance induction after CTLA4Ig treatment (FIG. 9D), Applicants can conclude that TIM-3 plays a fundamental role in regulating Th1-mediated immune responses and facilitating the generation of immunological tolerance.

In short, Applicants have described that the Ig superfamily member TIM-3 functions to inhibit aggressive Th1 mediated auto- and allo-immune responses. These effects appear to be mediated, at least in part, by the regulation of the immunosuppressive potency of CD4+CD25+ regulatory T cells. Hence, expression of TIM-3 upon Th1 cells provides a key check point that serves to dampen pro-inflammatory Th1-dependent T cell responses and limit the associated tissue injury.

E. REFERENCES

1. Romagnani, S. Lymphokine production by human T cells in disease states. *Annu Rev Immunol* 12, 227-57 (1994).
2. Kamradt, T. & Mitchison, N. A. Tolerance and autoimmunity. *N Engl J Med* 344, 655-64 (2001).
3. Strom, T. B. et al. The Th1/Th2 paradigm and the allograft response. *Curr Opin Immunol* 8, 688-93 (1996).
4. Li, X. C., Zand, M. S., Li, Y., Zheng, X. X. & Strom, T. B. On histocompatibility barriers, Th1 to Th2 immune deviation, and the nature of the allograft responses. *J Immunol* 161, 2241-7 (1998).
5. Anderson, G. P. & Coyle, A. J. TH2 and 'TH2-like' cells in allergy and asthma: pharmacological perspectives. *Trends Pharmacol Sci* 15, 324-32. (1994).
6. Kundig, T. M. et al. Duration of TCR stimulation determines costimulatory requirement of T cells. *Immunity* 5, 41-52. (1996).
7. Locksley, R. M., Killeen, N. & Lenardo, M. J. The TNF and TNF receptor superfamilies: integrating mammalian biology. *Cell* 104, 487-501. (2001).
8. Salomon, B. & Bluestone, J. A. Complexities of CD28/B7: CTLA-4 costimulatory pathways in autoimmunity and transplantation. *Annu Rev Immunol* 19, 225-52 (2001).
9. Refaeli, Y., Van Parijs, L., London, C. A., Tschopp, J. & Abbas, A. K. Biochemical mechanisms of IL-2-regulated Fas-mediated T cell apoptosis. *Immunity* 8, 615-23. (1998).
10. Monney, L. et al. Th1-specific cell surface protein Tim-3 regulates macrophage activation and severity of an autoimmune disease. *Nature* 415, 536-41. (2002).
11. Parker, D. C. et al. Survival of mouse pancreatic islet allografts in recipients treated with allogeneic small lymphocytes and antibody to CD40 ligand. *Proc Natl Acad Sci USA* 92, 9560-4. (1995).
12. Sanchez-Fueyo, A., Weber, M., Domenig, C., Strom, T. B. & Zheng, X. X. Tracking the immunoregulatory mechanisms active during allograft tolerance. *J Immunol* 168, 2274-81. (2002).

13. Quezada, S. A. et al. Mechanisms of donor specific transfusion tolerance: pre-emptive induction of clonal T cell exhaustion via indirect presentation. *Blood* (2003).
14. Coyle, A. J. et al. The CD28-related molecule ICOS is required for effective T cell-dependent immune responses. *Immunity* 13, 95-105 (2000).
15. Wells, A. D., Gudmundsdottir, H. & Turka, L. A. Following the fate of individual T cells throughout activation and clonal expansion. Signals from T cell receptor and CD28 differentially regulate the induction and duration of a proliferative response. *J Clin Invest* 100, 3173-83. (1997).
16. Sabatos, C. A. et al. Tim-3/Tim-3-Ligand interaction regulates Th1 responses and induction of peripheral tolerance. Submitted.
17. Delovitch, T. L. & Singh, B. The nonobese diabetic mouse as a model of autoimmune diabetes: immune dysregulation gets the NOD. *Immunity* 7, 727-38. (1997).
18. Christianson, S. W., Shultz, L. D. & Leiter, E. H. Adoptive transfer of diabetes into immunodeficient NOD-scid/scid mice. Relative contributions of CD4+ and CD8+ T-cells from diabetic versus prediabetic NOD.NON-Thy-1a donors. *Diabetes* 42, 44-55. (1993).
19. Rudd, C. E. et al. Two-step TCR zeta/CD3-CD4 and CD28 signaling in T cells: SH2/SH3 domains, protein-tyrosine and lipid kinases. *Immunol Today* 15, 225-34 (1994).
20. Prasad, K. V. et al. T-cell antigen CD28 interacts with the lipid kinase phosphatidylinositol 3-kinase by a cytoplasmic Tyr(P)-Met-Xaa-Met motif. *Proc Natl Acad Sci USA* 91, 2834-8 (1994).
21. Schneider, H., Cai, Y. C., Prasad, K. V., Shoelson, S. E. & Rudd, C. E. T cell antigen CD28 binds to the GRB-2/SOS complex, regulators of p21ras. *Eur J Immunol* 25, 1044-50 (1995).
22. Rudd, C. E. Upstream-downstream: CD28 cosignaling pathways and T cell function. *Immunity* 4, 527-34 (1996).
23. McIntire, J. J. et al. Identification of Tapr (an airway hyperreactivity regulatory locus) and the linked Tim gene family. *Nat Immunol* 2, 1109-16 (2001).
24. Kuchroo, V. K., Umetsu, D. T., DeKruyff, R. H. & Freeman, G. J. The TIM gene family: emerging roles in immunity and disease. *Nat Rev Immunol* 3, 454-62 (2003).
25. Li, X. C. et al. IL-2 and IL-4 double knockout mice reject islet allografts: a role for novel T cell growth factors in allograft rejection. *J Immunol* 161, 890-6 (1998).
26. Kishimoto, K. et al. The role of CD154-CD40 versus CD28-B7 costimulatory pathways in regulating allogeneic Th1 and Th2 responses in vivo. *J Clin Invest* 106, 63-72. (2000).
27. Sho, M. et al. Physiological Mechanisms of Regulating Alloimmunity: Cytokines, CTLA-4, CD25(+) Cells, and the Alloreactive T Cell Clone Size. *J Immunol* 169, 3744-51. (2002).
28. Zheng, X. X. et al. CTLA4 signals are required to optimally induce allograft tolerance with combined donor-specific transfusion and anti-CD154 monoclonal antibody treatment. *J Immunol* 162, 4983-90. (1999).
29. DeKruyff, R. H., Fang, Y. & Umetsu, D. T. IL-4 synthesis by in vivo primed keyhole limpet hemocyanin specific CD4+ T cells. I. Influence of antigen concentration and antigen presenting cell type. *J Immunol* 149, 3468-3476 (1992).
30. Judge, T. A. et al. The in vivo mechanism of action of CTLA4Ig. *J Immunol* 156, 2294-9 (1996).
31. Waaga, A. M. et al. Regulatory functions of self-restricted MHC class II allopeptide-specific Th2 clones in vivo. *J Clin Invest* 107, 909-16 (2001).
32. Lee, R. S. et al. CTLA4Ig-induced linked regulation of allogeneic T cell responses. *J Immunol* 166, 1572-82 (2001).
33. Maurik Av, A., Herber, M., Wood, K. J. & Jones, N. D. Cutting Edge: CD4(+)CD25(+) Alloantigen-Specific Immunoregulatory Cells That Can Prevent CD8(+) T Cell-Mediated Graft Rejection: Implications for Anti-CD154 Immunotherapy. *J Immunol* 169, 5401-4. (2002).
34. Kingsley, C. I., Karim, M., Bushell, A. R. & Wood, K. J. CD25+CD4+ regulatory T cells prevent graft rejection: CTLA-4- and IL-10-dependent immunoregulation of allo-responses. *J Immunol* 168, 1080-6. (2002).
35. Graca, L. et al. Both CD4(+)CD25(+) and CD4(+)CD25(−) regulatory cells mediate dominant transplantation tolerance. *J Immunol* 168, 5558-65. (2002).
36. Sakaguchi, S. & Sakaguchi, N. Thymus and autoimmunity: capacity of the normal thymus to produce pathogenic self-reactive T cells and conditions required for their induction of autoimmune disease. *J Exp Med* 172, 537-45. (1990).
37. Sakaguchi, S., Sakaguchi, N., Asano, M., Itoh, M. & Toda, M. Immunologic self-tolerance maintained by activated T cells expressing IL-2 receptor alpha-chains (CD25). Breakdown of a single mechanism of self-tolerance causes various autoimmune diseases. *J Immunol* 155, 1151-64. (1995).
38. Salomon, B. et al. B7/CD28 costimulation is essential for the homeostasis of the CD4+CD25+ immunoregulatory T cells that control autoimmune diabetes. *Immunity* 12, 431-40. (2000).
39. Wood, K. J. & Sakaguchi, S. Regulatory Lymphocytes: Regulatory T cells in transplantation tolerance. *Nat Rev Immunol* 3, 199-210 (2003).
40. Shevach, E. M. CD4+CD25+ suppressor T cells: more questions than answers. *Nat Rev Immunol* 2, 389-400 (2002).
41. Caramalho, I. et al. Regulatory T Cells Selectively Express Toll-like Receptors and Are Activated by Lipopolysaccharide. *J Exp Med* 197, 403-11 (2003).
42. Pasare, C. & Medzhitov, R. Toll Pathway-Dependent Blockade of CD4+CD25+ T Cell-Mediated Suppression by Dendritic Cells. *Science* 299, 1033-6 (2003).
43. Iwakoshi, N. N. et al. Treatment of allograft recipients with donor-specific transfusion and anti-CD 154 antibody leads to deletion of alloreactive CD8+ T cells and prolonged graft survival in a CTLA4-dependent manner. *J Immunol* 164, 512-21. (2000).
44. Yamazaki, S. et al. Direct Expansion of Functional CD25+ CD4+ Regulatory T Cells by Antigen-processing Dendritic Cells. *J Exp Med* 198, 235-47 (2003).
45. Walker, L. S., Chodos, A., Eggena, M., Dooms, H. & Abbas, A. K. Antigen-dependent Proliferation of CD4+ CD25+ regulatory T Cells In Vivo. *J Exp Med* 198, 249-58 (2003).
46. Buhlmann, J. E. et al. In the absence of a CD40 signal, B cells are tolerogenic. *Immunity* 2, 645-53 (1995).
47. Foy, T. M., Aruffo, A., Bajorath, J., Buhlmann, J. E. & Noelle, R. J. Immune regulation by CD40 and its ligand GP39. *Annu Rev Immunol* 14, 591-617 (1996).
48. Hollander, G. A. et al. Induction of alloantigen-specific tolerance by B cells from CD40-deficient mice. *Proc Natl Acad Sci USA* 93, 4994-8 (1996).
49. Martin, E., O'Sullivan, B., Low, P. & Thomas, R. Antigen-specific suppression of a primed immune response by dendritic cells mediated by regulatory T cells secreting interleukin-10. *Immunity* 18, 155-67 (2003).

50. Yoon, J. W. et al. Control of autoimmune diabetes in NOD mice by GAD expression or suppression in beta cells. *Science* 284, 1183-7 (1999).
51. Steiger, J., Nickerson, P. W., Steurer, W., Moscovitch-Lopatin, M. & Strom, T. B. IL-2 knockout recipient mice reject islet cell allografts. *J Immunol* 155, 489-98 (1995).
52. Li, Y. et al. Blocking both signal 1 and signal 2 of T-cell activation prevents apoptosis of alloreactive T cells and induction of peripheral allograft tolerance. *Nat Med* 5, 1298-302 (1999).

EQUIVALENTS

Those skilled in the art will recognize, or be able to ascertain using no more than routine experimentation, many equivalents to the specific embodiments of the invention described herein. Such equivalents are intended to be encompassed by the claims. Various publications are cited throughout this application. The contents of these publications are hereby incorporated by reference into this application

We claim:

1. A method of decreasing Th1-mediated immune response in a subject in need thereof, comprising administering to a subject in need thereof a galectin-9 polypeptide comprising the amino acid sequence of SEQ ID NO:10 or SEQ ID NO:19, that binds T cell immunoglobulin and mucin domain containing molecule-3 (tim-3) and increases tim-3 activity, wherein said increase in tim-3 activity results in a decrease in the induction of at least one Th1 cytokine, to decrease Th1-mediated immune responses in the subject.

2. The method of claim 1, wherein the subject is afflicted with an autoimmune disease.

3. The method of claim 2, wherein the autoimmune disease is multiple sclerosis, type-I diabetes, Hashinoto's thyroiditis, Crohn's disease, rheumatoid arthritis, systemic lupus erythematosus, gastritis, autoimmune hepatitis, hemolytic anemia, autoimmune hemophilia, autoimmune lymphoproliferative syndrome (ALPS), autoimmune uveoretinitis, glomerulonephritis, Guillain-Barré syndrome, psoriasis, or myasthenia gravis.

4. The method of claim 1, wherein the galectin-9 polypeptide comprising the amino acid sequence of SEQ ID NO:10 or SEQ ID NO:19 or galectin-9 conservative substitution variant polypeptide comprises at least one of the two carbohydrate recognition domains (CRD) of galectin-9.

5. The method of claim 1, wherein the galectin-9 polypeptide comprising the amino acid sequence of SEQ ID NO:10 or SEQ ID NO:19 comprises two CRD domains of galectin-9.

6. A method of increasing transplantation tolerance in a subject in need thereof, comprising administering to a subject in need thereof a galectin-9 polypeptide comprising the amino acid sequence of SEQ ID NO:10 or SEQ ID NO:19 that binds T cell immunoglobulin and mucin domain containing molecule-3 (tim-3) and increases tim-3 activity, wherein said increase in tim-3 activity results in a decrease in the induction of at least one Th1 cytokine, to decrease Th1-mediated immune responses in the subject.

7. The method of claim 6, wherein the subject is afflicted with an host versus graft disease (HVGD).

8. The method of claim 6, wherein the subject is an organ transplant recipient.

* * * * *